US011180609B2

(12) United States Patent
Farmer

(10) Patent No.: US 11,180,609 B2
(45) Date of Patent: Nov. 23, 2021

(54) SUSTAINABLE POLYMER COMPOSITIONS AND METHODS

(71) Applicant: Saudi Aramco Technologies Company, Dhahran (SA)

(72) Inventor: Jay J. Farmer, Houston, TX (US)

(73) Assignee: Saudi Aramco Technologies Company, Dhahran (SA)

(*) Notice: Subject to any disclaimer, the term of this patent is extended or adjusted under 35 U.S.C. 154(b) by 187 days.

(21) Appl. No.: 16/528,801

(22) Filed: Aug. 1, 2019

(65) Prior Publication Data

US 2020/0062900 A1 Feb. 27, 2020

Related U.S. Application Data

(60) Provisional application No. 62/713,849, filed on Aug. 2, 2018.

(51) Int. Cl.
*C08G 64/34* (2006.01)
*C08G 63/64* (2006.01)
*C08G 63/82* (2006.01)
*C08G 64/02* (2006.01)
*C08G 64/18* (2006.01)

(52) U.S. Cl.
CPC .......... *C08G 64/34* (2013.01); *C08G 63/64* (2013.01); *C08G 63/826* (2013.01); *C08G 64/0208* (2013.01); *C08G 64/0291* (2013.01); *C08G 64/183* (2013.01)

(58) Field of Classification Search
USPC ................................. 528/196, 198, 308, 357
See application file for complete search history.

(56) References Cited

U.S. PATENT DOCUMENTS

| | | |
|---|---|---|
| 3,248,415 A | 4/1966 | Stevens et al. |
| 3,585,168 A | 6/1971 | Inoue et al. |
| 3,900,424 A | 8/1975 | Inoue et al. |
| 3,953,383 A | 4/1976 | Inoue et al. |
| 3,984,333 A | 10/1976 | van de Kraats et al. |
| 4,480,696 A | 11/1984 | Almond et al. |
| 4,500,704 A | 2/1985 | Kruper, Jr. et al. |
| 4,665,136 A | 5/1987 | Santangelo et al. |
| 4,686,276 A | 8/1987 | Myers |
| 4,826,953 A | 5/1989 | Kuyper et al. |
| 4,910,256 A | 3/1990 | Prier |
| 4,921,635 A | 5/1990 | Enick |
| 5,566,470 A | 10/1996 | Morrison |
| 5,637,739 A | 6/1997 | Jacobsen et al. |
| 5,663,393 A | 9/1997 | Jacobsen et al. |
| 5,665,890 A | 9/1997 | Jacobsen et al. |
| 5,880,293 A | 3/1999 | Godvigovna et al. |
| 5,929,232 A | 7/1999 | Jacobsen et al. |
| 6,130,340 A | 10/2000 | Jacobsen et al. |
| 6,133,402 A | 10/2000 | Coates et al. |
| 6,262,127 B1 | 7/2001 | Acemoglu et al. |
| 6,309,997 B1 | 10/2001 | Fujita et al. |
| 6,515,145 B2 | 2/2003 | Machac, Jr. et al. |
| 6,617,467 B1 | 9/2003 | Muller et al. |
| 6,639,087 B2 | 10/2003 | Larrow et al. |
| 6,677,268 B2 | 1/2004 | Hillebrand et al. |
| 6,686,438 B1 | 2/2004 | Beckman et al. |
| 6,713,599 B1 | 3/2004 | Hinz et al. |
| 6,781,006 B2 | 8/2004 | Larrow et al. |
| 6,844,448 B2 | 1/2005 | Jacobsen et al. |
| 6,852,865 B2 | 2/2005 | Coates et al. |
| 6,870,004 B1 | 3/2005 | Nguyen et al. |
| 6,875,718 B2 | 4/2005 | Fujita et al. |
| 6,884,750 B2 | 4/2005 | Kim et al. |
| 6,903,043 B2 | 6/2005 | Kim et al. |
| 7,145,022 B2 | 12/2006 | Luinstra et al. |
| 7,148,174 B2 | 12/2006 | Schulte et al. |
| 7,244,805 B2 | 7/2007 | Park et al. |
| 7,268,204 B2 | 9/2007 | Hinz et al. |
| 7,300,903 B2 | 11/2007 | Fujita et al. |
| 7,304,172 B2 | 12/2007 | Coates et al. |
| 7,399,822 B2 | 7/2008 | Coates et al. |
| 7,674,873 B2 | 3/2010 | Coates et al. |
| 7,723,256 B2 | 5/2010 | Coates et al. |
| 7,858,729 B2 | 12/2010 | Allen |
| 7,977,501 B2 | 7/2011 | Haider et al. |
| 8,163,867 B2 | 4/2012 | Lee et al. |
| 8,207,365 B2 | 6/2012 | Zheng et al. |
| 8,232,267 B2 | 7/2012 | Groves |
| 8,247,520 B2 | 8/2012 | Allen et al. |
| 8,252,955 B2 | 8/2012 | Gao et al. |
| 8,278,239 B2 | 10/2012 | Coates et al. |

(Continued)

FOREIGN PATENT DOCUMENTS

| | | |
|---|---|---|
| CA | 1312398 C | 1/1993 |
| CA | 2083878 A1 | 6/1993 |

(Continued)

OTHER PUBLICATIONS

U.S. Appl. No. 16/580,705, filed Sep. 24, 2019, Allen et al..
U.S. Appl. No. 16/683,820, filed Nov. 14, 2019, Waddington.
Ahn Tae-wan, Munundang, Polymer Chemistry, First Edition, 5.4: 175-176 (issued Jun. 30, 2010). No English Translation Available.
Bertozzi, C.R. and Bednarski, M.D., The Synthesis of Heterobifunctional Linkers for the Conjugation of Ligands to Molecular Probes, Journal of Organic Chemistry, 56(13):4326-4329 (1991).
Byrne, C.M. et al., Alternating Copolymerization of Limonene Oxide and Carbon Dioxide, Journal of the American Chemical Society, 126(37): 11404-11405 (2004).
Chen, L., Activation and copolymerization of CO2 by macromolecule-metal complexes, Die Makromolekulare Chemie, Macromolecular Symposia, 59: 75-82 (1992).

(Continued)

*Primary Examiner* — Terressa Boykin
(74) *Attorney, Agent, or Firm* — Choate, Hall & Stewart LLP; John P. Rearick; Nicholas J. Pace

(57) ABSTRACT

In one aspect, the present invention encompasses compositions of sustainable polycarbonate polymers, methods of producing such polymers, and methods for evaluating whether certain constituents of a polymer chain are derived from biomass or a fossil carbon source.

22 Claims, No Drawings

(56) References Cited

U.S. PATENT DOCUMENTS

| | | |
|---|---|---|
| 8,461,290 B2 | 6/2013 | Carpentier et al. |
| 8,470,956 B2 | 6/2013 | Allen et al. |
| 8,507,733 B2 | 8/2013 | Ok et al. |
| 8,580,911 B2 | 11/2013 | Allen et al. |
| 8,598,309 B2 | 12/2013 | Jeong et al. |
| 8,604,155 B2 | 12/2013 | Allen et al. |
| 8,633,123 B2 | 1/2014 | Allen et al. |
| 8,642,721 B2 | 2/2014 | Ok et al. |
| 8,785,591 B2 | 7/2014 | Allen et al. |
| 8,791,274 B2 | 7/2014 | Ok et al. |
| 8,921,508 B2 | 12/2014 | Allen et al. |
| 8,946,109 B2 | 2/2015 | Allen et al. |
| 8,951,930 B2 | 2/2015 | Allen et al. |
| 8,952,104 B2 | 2/2015 | Allen |
| 8,956,989 B2 | 2/2015 | Allen et al. |
| 9,029,498 B2 | 5/2015 | Allen et al. |
| 9,102,800 B2 | 8/2015 | Allen et al. |
| 9,284,406 B2 | 3/2016 | Farmer |
| 9,327,280 B2 | 5/2016 | Lee et al. |
| 9,359,473 B2 | 6/2016 | Nagao et al. |
| 9,376,531 B2 | 6/2016 | Allen et al. |
| 9,388,277 B2 | 7/2016 | Farmer |
| 9,394,326 B2 | 7/2016 | Farmer |
| 9,399,701 B2 | 7/2016 | Allen et al. |
| 9,422,397 B2 | 8/2016 | Allen et al. |
| 9,453,100 B2 | 9/2016 | Allen et al. |
| 9,505,878 B2 | 11/2016 | Allen et al. |
| 9,512,259 B2 | 12/2016 | Allen et al. |
| 9,512,269 B2 | 12/2016 | Allen et al. |
| 9,809,678 B2 | 11/2017 | Allen et al. |
| 9,834,710 B2 | 12/2017 | Allen et al. |
| 9,850,345 B2 | 12/2017 | Farmer |
| 9,884,937 B2 | 2/2018 | Allen et al. |
| 9,994,760 B2 | 6/2018 | Allen et al. |
| 10,047,188 B2 | 8/2018 | Allen et al. |
| 10,138,369 B2 | 11/2018 | Allen et al. |
| 10,214,614 B2 | 2/2019 | Coates et al. |
| 10,301,426 B2 | 5/2019 | Allen et al. |
| 10,351,654 B2 | 7/2019 | Allen et al. |
| 10,392,556 B2 | 8/2019 | Allen et al. |
| 10,428,173 B2 | 10/2019 | Allen et al. |
| 10,836,859 B2 | 11/2020 | Allen et al. |
| 10,982,036 B2 | 4/2021 | Allen et al. |
| 11,021,564 B2 | 6/2021 | Allen et al. |
| 2005/0215438 A1 | 9/2005 | Prud'homme et al. |
| 2006/0223973 A1 | 10/2006 | Hinz et al. |
| 2006/0293501 A1 | 12/2006 | Coates et al. |
| 2008/0021154 A1 | 1/2008 | Haider et al. |
| 2008/0051554 A1 | 2/2008 | Coates et al. |
| 2008/0243049 A1 | 10/2008 | Hardy |
| 2010/0048935 A1 | 2/2010 | Mijolovic et al. |
| 2010/0121026 A1 | 5/2010 | Lee et al. |
| 2010/0256329 A1 | 10/2010 | Nozaki et al. |
| 2010/0323201 A1 | 12/2010 | Son et al. |
| 2011/0152497 A1 | 6/2011 | Allen et al. |
| 2011/0207909 A1 | 8/2011 | Jeong et al. |
| 2011/0230580 A1 | 9/2011 | Allen et al. |
| 2011/0245424 A1 | 10/2011 | Jeong et al. |
| 2011/0251355 A1 | 10/2011 | Jeong et al. |
| 2012/0156410 A1 | 6/2012 | Allen |
| 2013/0022771 A1 | 1/2013 | Malet et al. |
| 2013/0066044 A1 | 3/2013 | Allen et al. |
| 2013/0144031 A1 | 6/2013 | Allen et al. |
| 2013/0144032 A1 | 6/2013 | Allen et al. |
| 2013/0144033 A1 | 6/2013 | Allen et al. |
| 2013/0244864 A1 | 9/2013 | Allen et al. |
| 2013/0337204 A1 | 12/2013 | Michel et al. |
| 2014/0031453 A1 | 1/2014 | Allen et al. |
| 2014/0046008 A1 | 2/2014 | Allen et al. |
| 2014/0249279 A1 | 9/2014 | Williams et al. |
| 2015/0166734 A1 | 6/2015 | Allen et al. |
| 2015/0299386 A1 | 10/2015 | Allen et al. |
| 2015/0307660 A1 | 10/2015 | Allen et al. |
| 2016/0115288 A1 | 4/2016 | Waddington |
| 2016/0264728 A1 | 9/2016 | Allen et al. |
| 2017/0002136 A1* | 1/2017 | Sookraj ............... C08G 63/183 |
| 2017/0183447 A1 | 6/2017 | Allen et al. |
| 2018/0022869 A1 | 1/2018 | Allen et al. |
| 2019/0100648 A1 | 4/2019 | Allen et al. |
| 2019/0322802 A1 | 10/2019 | Eagan et al. |
| 2020/0095375 A1 | 3/2020 | Allen et al. |
| 2020/0095494 A1 | 3/2020 | Allen et al. |
| 2020/0325296 A1 | 10/2020 | Waddington |
| 2021/0171708 A1 | 6/2021 | Allen et al. |

FOREIGN PATENT DOCUMENTS

| | | |
|---|---|---|
| CN | 101020747 A | 8/2007 |
| CN | 101412809 A | 4/2009 |
| CN | 102066459 A | 5/2011 |
| CN | 102585192 A | 7/2012 |
| EP | 0222453 A2 | 5/1987 |
| EP | 0403313 A2 | 12/1990 |
| EP | 2112187 A1 | 10/2009 |
| EP | 2258745 A1 | 12/2010 |
| EP | 2146977 B1 | 11/2012 |
| EP | 2257559 B1 | 10/2014 |
| JP | H02-258828 A | 10/1990 |
| JP | 2575199 B2 | 1/1997 |
| JP | 2691014 B2 | 12/1997 |
| JP | 2005-511753 A | 4/2005 |
| JP | 2006002063 A | 1/2006 |
| JP | 2008-081518 | 4/2008 |
| JP | 2008-280399 A | 11/2008 |
| JP | 2008-546785 A | 12/2008 |
| JP | 2009-215529 A | 9/2009 |
| JP | 2010-202711 A | 9/2010 |
| KR | 2005-0113651 A | 12/2005 |
| KR | 10-2008-0016198 A | 2/2008 |
| KR | 10-0853358 B1 | 8/2008 |
| WO | WO-91/14694 A1 | 10/1991 |
| WO | WO-98/04538 A1 | 2/1998 |
| WO | WO-99/00444 A1 | 1/1999 |
| WO | WO-00/35998 A2 | 6/2000 |
| WO | WO-03/050154 A2 | 6/2003 |
| WO | WO-2004/087788 A1 | 10/2004 |
| WO | WO-2008/136591 A1 | 11/2008 |
| WO | WO-2008/150033 A1 | 12/2008 |
| WO | WO-2009/130182 A1 | 10/2009 |
| WO | WO-2009/137540 A1 | 11/2009 |
| WO | WO-2009/148889 A2 | 12/2009 |
| WO | WO-2010/013948 A2 | 2/2010 |
| WO | WO-2010/022388 A2 | 2/2010 |
| WO | WO-2010/028362 A1 | 3/2010 |
| WO | WO-2010/060038 A1 | 5/2010 |
| WO | WO-2010/062703 A1 | 6/2010 |
| WO | WO-2010/134425 A1 | 11/2010 |
| WO | WO-2010/147237 A1 | 12/2010 |
| WO | WO-2011/004730 A1 | 1/2011 |
| WO | WO-2011/005664 A2 | 1/2011 |
| WO | WO-2011/163133 A1 | 12/2011 |
| WO | WO-2012/027725 A1 | 3/2012 |
| WO | WO-2012/071505 A1 | 5/2012 |
| WO | WO-2012/094619 A1 | 7/2012 |
| WO | WO-2012/154849 A1 | 11/2012 |
| WO | WO-2013/016331 A2 | 1/2013 |
| WO | WO-2013/096602 A1 | 6/2013 |
| WO | WO-2013/138161 A1 | 9/2013 |
| WO | WO-2013/158621 A1 | 10/2013 |
| WO | WO-2013/163442 A1 | 10/2013 |
| WO | WO-2013/177546 A2 | 11/2013 |
| WO | WO-2014/074706 A1 | 5/2014 |
| WO | WO-2014/186397 A1 | 11/2014 |
| WO | WO-2015/154001 A1 | 10/2015 |
| WO | WO-2019/204553 A1 | 10/2019 |
| WO | WO-2020/028606 A1 | 2/2020 |

OTHER PUBLICATIONS

Cheng, M et al., Catalytic Reactions Involving C1 Feedstocks: New High-Activity Zn(II)—Based Catalysts for the Alternating Copolymerization of Carbon Dioxide and Epoxides, J. Am. Chem. Soc., 120: 11018-11019 (1998).

(56) References Cited

OTHER PUBLICATIONS

Cheng, M et al., Catalytic Reactions Involving C1 Feedstocks: New High-Activity Zn(II)—Based Catalysts for the Alternating Copolymerization of Carbon Dioxide and Epoxides, J. Am. Chem. Soc., 120: 11018-11019 (1998). Supporting Information, 10 pages.
Cheng, M. et al., Single-Site a-Diiminate Zinc Catalysts for the Alternating Copolymerization of CO2 and Epoxides: Catalyst Synthesis and Unprecedented Polymerization Activity, J. Am. Chem. Soc., 123: 8738-8749 (2001).
Coates et al., Cobalt-Based Complexes for the Copolymerization of Propylene Oxide and CO2 : Active and Selective Catalysts for Polycarbonate Synthesis, Angew. Chem. Int. Ed., 42: 5484-5487 (2003).
Coates et al., Electronic and Steric Effects on Catalysts for CO2/Epoxide Polymerization: Subtle Modifications Resulting in Superior Activities, Angew. Chem. Int. Ed., 41: 2599-2602 (2002).
Coates, G.W. and Moore, D.R., Discrete Metal-Based Catalysts for the Copolymerization of CO2 and Epoxides: Discovery, Reactivity, Optimization, and Mechanism, Angewandte Chemie International Edition, 43: 6618-6639 (2004).
Cohen et al. Alternating Copolymerization of Propylene Oxide and Carbon Dioxide with Highly Efficient and Selective (Salen)Co(III) Catalysts: Effect of Ligand and Cocatalyst Variation, J. Polymer Sci.: Part A, 44: 5182-5191 (2006).
Cohen, C.T. et al., Cobalt Catalysts for the Alternating Copolymerization of Propylene Oxide and Carbon Dioxide: Combining High Activity and Selectivity, J. Am. Chem. Soc., 127: 10869-10878 (2005).
Cui, S. et al., Recent advances of "soft" bio-polycarbonate plastics from carbon dioxide and renewable bio-feedstocks via straightforward and innovative routes, Journal of CO2 Utilization, 34: 40-52 (2019).
Darensbourg, D.J. et al., Mechanistic aspects of the copolymerization reaction of carbon dioxide and epoxides, using a chiral salen chromium chloride catalyst, Journal of the American Chemical Society, 124: 6335-6342 (2002).
Darensbourg, D.J., Making plastics from carbon dioxide: salen metal complexes as catalysts for the production of polycarbonates from epoxides and CO2, Chemical Reviews, 107(6): 2388-410 (2007).
Gao et al., Copolimerization of Carbon Dioxide and Propylene Oxide with Zinc Glutarate as Catalyst in the Presence of Compounds Containing Active Hydrogen, Journal of Applied Polymer Science, 104: 15-20 (2006).
Gorecki, P. and Kuran, W., Diethylzinc-trihydric phenol catalysts for copolymerization of carbon dioxide and propylene oxide: Activity in Copolymerization and Copolymer destruction processes, Journal of Polymer Science, Part C, 23: 299-304 (1985).
Inoue, S., Immortal Polymerization: The Outset, Development, and Application, Journal of Polymer Science: Part A: Polymer Chemistry, 38: 2861-2871 (2000).
International Search Report for PCT/US2009/056220, 3 pages (dated Nov. 20, 2009).
International Search Report for PCT/US2009/062871,4 pages (dated Jan. 22, 2010).
International Search Report for PCT/US2019/044573, 5 pages (dated Oct. 23, 2019).
Ionescu, M., Chemistry and Technology of Polyols for Polyurethanes, Rapra Technology Limited, 605 pages (2005).
Jacobsen et al., Electronic Tuning of Asymmetric Catalysts, J. Am. Chem. Soc., 113: 6703-6704 (1991).
Jacobsen et al., Enantioselective Epoxidation of Unfunctionalized Olefins Catalyzed by (Salen) manganese Complexes, J. Am. Chem. Soc., 112, 2801-2803 (1990).
Jacobsen et al., Highly Enantioselective Epoxidation Catalysts Derived from 1,2 Diaminocyclohexane, J. Am. Chem. Soc., 113:7063-7064 (1991).
Kim Sung-Chul et al., Polymer Engineering I, Heejungdang, 18-20 (1994). Best Available Copy. No English Translation Available.

Kuran, W. et al., Alternating copolymerization of carbon dioxide and propylene oxide in the presence of organometallic catalysts, Die Makromolekulare Chemie, 177:11-20 (1976).
Lee et al., A Highly Active and Recyclable Catalytic System for CO2/Propylene Oxide Copolymerizations, Angew. Chem., 120: 7416-7419 (2008).
Lee et al., Connection of polymer chains using diepoxide in CO2/propylene oxide copolymerizations, Polym. Chem., 2:950-956 (2011).
Lee, Preparation of flame-retarding poly(propylene carbonate), Green Chem., 13: 3469-3475 (2011).
Lu et al., Asymmetric Catalysis with CO2: Direct Syntheis of Optically Active Propylene Carbonate from Racemic Epoxides, J. Am. Chem. Soc., 126: 3732-3733 (2004).
Lu et al., Cobalt catalysts for the coupling of CO2 and epoxides to provide polycarbonates and cyclic arbonates, Chem. Soc. Rev., 41:1462-1484 (2012).
Lu et al., Design of Highly Active Binary Catalyst Systems for CO/Epoxide Copolymerization: Polymer Selectivity, Enantioselectivity, and Stereochemistry Control, J. Am. Chem. Soc., 128: 1664-1674 (2006).
Lu et al., Highly Active, Binary Catalyst Systems for the Alternating Copolymerization of CO2 and Epoxides under Mild Conditions, Angew. Chem. Int. Ed., 43: 3574-3577 (2004).
Lu et al., Mechanistic Aspects of the Copolymerization of CO2 with Epoxides Using a Thermally Stable Single-Site Cobalt(III) Catalyst, J. Am. Chem. Soc., 131: 11509-11518 (2009).
Marbach, J. Zinc glutarate-mediated copolymerization of CO2 and PO—parameter studies using design of experiments, Catal. Sci. Technol., 7: 2897-2905 (2017).
Nakajima et al., Asymmetric Oxidation of Sulfides to Sulfoxides by Organic Hydroperoxides with Optically Active Schiff Base-Oxovanadium (IV) Catalysts, Chemistry Letters, 1483-1486 (1986).
Nakano, K. et al., Selective Formation of Polycarbonate over Cyclic Carbonate: Copolymerization of Epoxides with Carbon Dioxide Catalyzed by a Cobalt (III) Complex with a Piperidinium End-Capping Arm, Angew. Chem. Int. Ed., 45: 7274-7277 (2006).
Nakano, K. et al., Supporting Information, 12 pages (2006). Selective Formation of Polycarbonate over Cyclic Carbonate: Copolymerization of Epoxides with Carbon Dioxide Catalyzed by a Cobalt (III) Complex with a Piperidinium End-Capping Arm, Angew. Chem. Int. Ed., 45: 7274-7277 (2006).
Noordover, B.A.J., Biobased step-growth polymers: chemistry, functionality and applicability, Eindhoven University of Technology, 219 pages (Published Jan. 1, 2008). [Download date Apr. 20, 2018].
Odian, G., Principles of Polymerization, Second Edition, Korean Student Edition, Yeonhap Publishing Company, 1-12 (issued Jul. 20, 1986).
Qin, Z. et al., Cobalt-based complexes for the copolymerization of propylene oxide and CO2: active and selective catalysts for; polycarbonate synthesis, Angewandte Chemie International Edition English, 42(44):5484-7 (2003).;.
Rieger et al., Recent advances in CO2/epoxide copolymerization—New strategies and cooperative mechanisms, Coordination Chemistry Reviews 255:1460-1479 (2011).
Smith, C. P et al., Thermoplastic Polyurethane Elastomers Made from High Molecular Weight POLY-L® Polyols, Journal of Elastomers and Plastics, 24: 306-322 (1992).
Sugimoto et al., Manufacture of alkylene oxide-carbon dioxide copolymers, Database CA [Online] Chemical Abstracts Service, Database accession No. 2008:444531, Abstract (Dec. 31, 2008).
Sugimoto, H et al., Alternating Copolymerization of Carbon Dioxide and Epoxide Catalyzed by an Aluminum Schiff Base—Ammonium Salt System, Journal of Polymer Science: Part A: Polymer Chemistry, 43: 4172-4186 (2005).
Sujith et al., A Highly Active and Recyclable Catalytic System for CO2/Propylene Oxide Copolymerization, Angew. Chem. Int. Ed., 47: 7306-7309 (2008).
Sujith et al., A Highly Active and Recyclable Catalytic System for CO2/Propylene Oxide Copolymerization, Angew. Chem. Int. Ed., 47: 7306-7309 (2008). Supporting Information.

(56) References Cited

OTHER PUBLICATIONS

Van Meerendonk, W.J. et al., Unexpected Side Reactions and Chain Transfer for Zinc-Catalyzed Copolymerization of Cyclohexene Oxide and Carbon Dioxide, Macromolecules, 38: 7306-7313 (2005).
Williams et al., Catalysts for CO2/epoxide Polymerisation, Chem Commun., 47:141-163 (2011).
Yang et al., Rate of Regulated Copolymerization Involving CO2, Journal of Natural Gas Chemistry, 7(2): 149-156 (1998).
Zhang, X.H. et al., Highly active double metal cyanide complexes: Effect of central metal and ligand on reaction of epoxide/CO2, Chinese Chemical Letters, 18: 887-890 (2007).
Zhang, Y-Y. et al., Synthesis of fully alternating polycarbonate with low T g from carbon dioxide and bio-based fatty acid, 4(68): 36183-36188 (2014).
U.S. Appl. No. 17/195,740, filed Mar. 9, 2021, Allen et al.

\* cited by examiner

SUSTAINABLE POLYMER COMPOSITIONS AND METHODS

CROSS-REFERENCE TO RELATED APPLICATIONS

This application claims priority to U.S. Provisional Patent Application No. 62/713,849, filed Aug. 2, 2018, the entire of which is hereby incorporated by reference.

FIELD OF THE INVENTION

This invention pertains to the field of sustainable polymers, methods of producing such polymers, and methods for evaluating whether certain constituents of a polymer chain are derived from biomass or a fossil carbon source. Such compositions and methods may be used for measuring and improving the sustainability profile of polymers.

BACKGROUND OF THE INVENTION

Polycarbonate polymers may be produced through epoxide-$CO_2$ copolymerization. Such polycarbonates are used across a broad range of applications, for example epoxide $CO_2$-derived polyols are used to produce polyurethane foams, coatings, and adhesives. There is a strong demand from consumers and manufacturing companies for polymer compositions, and particularly polycarbonate compositions, with improved sustainability profiles.

SUMMARY OF THE INVENTION

In one aspect, the present invention provides polymer compositions that are derived from both biomass and a fossil carbon source. In some embodiments, the polymer compositions have desirable sustainability profiles, since they comprise both biobased carbon and sequester fossil-derived carbon that would otherwise be released to the atmosphere. In some embodiments, the invention encompasses polycarbonate compositions whose manufacture sequesters $CO_2$ produced from a fossil carbon source while simultaneously utilizing biobased feedstocks as constituents of the polymer chain. Chemistry used to make such polymer chains results in the biobased carbon atoms and the fossil-derived carbon atoms being incorporated at predictable locations in the polymer chains, as shown in Scheme 1.

In some embodiments, because the two polymer precursors are derived from different sources, polymer chains made according to Scheme 1 have a unique composition with respect to the isotopic fingerprint of the carbon atoms within the polymer chains. For example, in certain embodiments, the present invention provides polymer compositions, where the radiocarbon content of the fossil carbon atoms comprising the carbonate linkages is lower than the radiocarbon content of the biobased carbon atoms comprising the optionally substituted two-carbon unit between the carbonate linkages in the polymer chains.

In another aspect, the present invention provides methods of producing such polymer compositions with improved sustainability profiles. In some embodiments, such methods comprise the steps of treating biomass to produce biobased ethanol; converting the biobased ethanol to a biobased epoxide; and copolymerizing carbon dioxide sequestered from a fossil carbon source with the biobased epoxide to produce a polymer composition.

In another aspect, the present invention provides methods of determining the provenance of particular carbon atoms within the polymer compositions described above and herein. In some embodiments, the present invention provides methods comprising treating a polymer composition to liberate a cyclic carbonate; treating the cyclic carbonate to liberate $CO_2$ and an epoxide; optionally separating the $CO_2$ from the epoxide; and measuring the radiocarbon content of the $CO_2$ and the epoxide. In certain embodiments, a method comprises, as shown in Scheme 2: treating polymer chains of formula 1 to decompose them to a cyclic carbonate of formula 2 (for example, by heating the polymer composition or treating it with strong base); treating the cyclic carbonate of formula 2 under conditions to decompose it to $CO_2$ and a small molecule such as an epoxide of formula 3 (for example, by treating it according to the methods disclosed in U.S. Pat. No. 4,069,234); optionally separating the $CO_2$ and epoxide; and analyzing each to determine its radiocarbon content (for example, by utilizing a method such as those described in ASTM D6866-16).

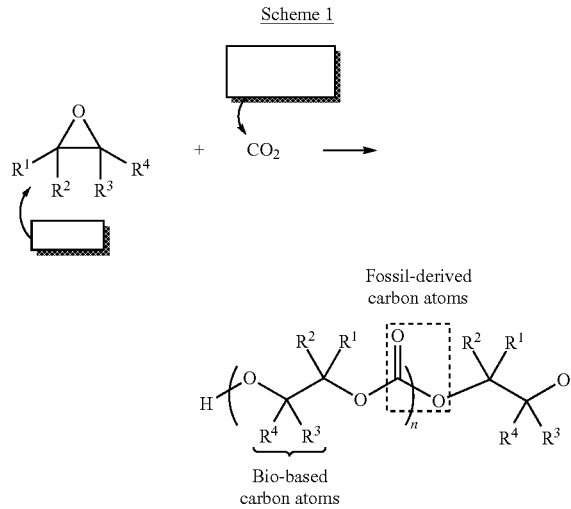

where $R^1$, $R^2$, $R^1$, $R^4$, and n are as described herein.

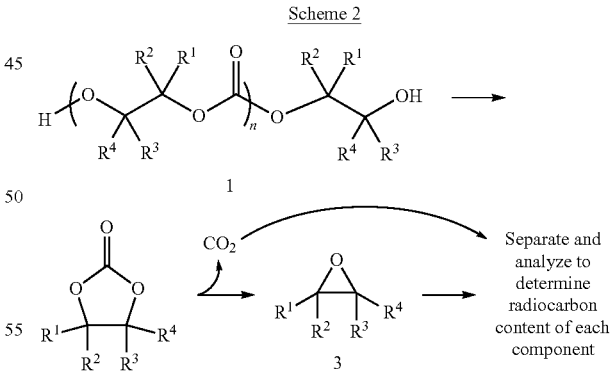

where $R^1$, $R^2$, $R^3$, $R^4$, and n are as described herein.

Definitions

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*. 3$^{rd}$ Edition. Cambridge University Press, Cambridge, 1987; the entire contents of each of which are incorporated herein by reference.

Certain molecules (e.g., polymers, epoxides, etc.) of the present invention can comprise one or more asymmetric centers, and thus can exist in various stereoisomeric forms, e.g., enantiomers and/or diastereomers. Thus, inventive molecules and compositions thereof may be in the form of an individual enantiomer, diastereomer or geometric isomer, or may be in the form of a mixture of stereoisomers. In certain embodiments, the molecules of the invention are enantiopure molecules. In certain embodiments, mixtures of enantiomers or diastereomers are provided.

Certain molecules described herein may have one or more double bonds that can exist as either the Z or E isomer, unless otherwise indicated. The invention additionally encompasses the molecules as individual isomers substantially free of other isomers and alternatively, as mixtures of various isomers, e.g., racemic mixtures of enantiomers. In addition to the above-mentioned molecules per se, this invention also encompasses compositions comprising one or more molecules.

As used herein, the term "isomers" includes any and all geometric isomers and stereoisomers. For example, "isomers" include cis- and trans-isomers, E- and Z-isomers, R- and S-enantiomers, diastereomers. (D)-isomers, (L)-isomers, racemic mixtures thereof, and other mixtures thereof, as falling within the scope of the invention. For instance, a stereoisomer may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the molecule is made up of a significantly greater proportion of one enantiomer. In certain embodiments the molecule is made up of at least about 90% by weight of a preferred enantiomer. In other embodiments the molecule is made up of at least about 95%, 98%, or 99% by weight of a preferred enantiomer. Preferred enantiomers may be isolated from racemic mixtures by any method known to those skilled in the art, including chiral high-pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977), Eliel, E. L. *Stereochemistry of Carbon Compounds* (McGraw-Hill, NY. 1962); Wilen, S. H. *Tables of Resolving Agents and Optical Resolutions* p. 268 (E. L. Eliel, Ed., Univ. of Notre Dame Press, Notre Dame, Ind. 1972).

The term "epoxide", as used herein, refers to a substituted or unsubstituted oxirane. Such substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "polymer", as used herein, refers to a molecule of high relative molecular mass, the structure of which comprises the multiple repetitions of units derived, actually or conceptually, from molecules of low relative molecular mass. In certain embodiments, a polymer is comprised of substantially alternating units derived from $CO_2$ and an epoxide (e.g., poly(ethylene carbonate)). In certain embodiments, a polymer of the present invention is a copolymer, terpolymer, heteropolymer, block copolymer, or tapered heteropolymer incorporating two or more different epoxide monomers. With respect to the structural depiction of such higher polymers, the convention of showing enchainment of different monomer units separated by a slash may be used as depicted herein, e.g.,

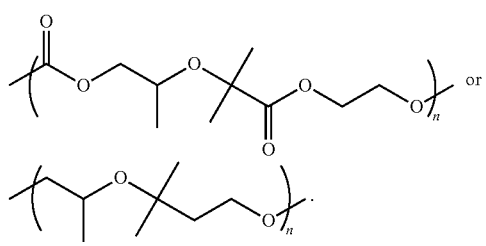

These structures are to be interpreted to encompass copolymers incorporating any ratio of the different monomer units depicted unless otherwise specified. This depiction is also meant to represent random, tapered, block copolymers, and combinations of any two or more of these and all of these are implied unless otherwise specified.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-40 carbon atoms. In certain embodiments, aliphatic groups contain 1-20 carbon atoms. In certain embodiments, aliphatic groups contain 3-20 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in some embodiments aliphatic groups contain 1-3 carbon atoms, and in some embodiments aliphatic groups contain 1 or 2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, or phosphorus. In certain embodiments, one to six carbon atoms are independently replaced by one or more of oxygen, sulfur, nitrogen, or phosphorus. Heteroaliphatic groups may be substituted or unsubstituted, branched or unbranched, cyclic or acyclic, and include saturated, unsaturated or partially unsaturated groups.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In certain embodiments, the term "3- to 7-membered carbocycle" refers to a 3- to 7-membered saturated or partially unsaturated monocyclic carbocyclic ring. In certain embodiments, the term "3- to 8-membered carbocycle" refers to a 3- to 8-membered saturated or partially unsaturated monocyclic carbocyclic ring. In certain embodiments, the terms "3- to 14-membered carbocycle" and "$C_{3-14}$ carbocycle" refer to a 3- to 8-membered saturated or partially unsaturated monocyclic carbocyclic ring, or a 7- to 14-membered saturated or partially unsaturated polycyclic carbocyclic ring.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in some embodiments alkyl groups contain 1-3 carbon atoms, and in some embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in some embodiments alkenyl groups contain 2-3 carbon atoms, and in some embodiments alkenyl groups contain 2 carbon atoms. Alkenyl groups include, for example, ethenyl, propenyl, butenyl, 1-methyl-2-buten-1-yl, and the like.

The term "alkynyl." as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in some embodiments alkynyl groups contain 2-3 carbon atoms, and in some embodiments alkynyl groups contain 2 carbon atoms. Representative alkynyl groups include, but are not limited to, ethynyl, 2-propynyl (propargyl), 1-propynyl, and the like.

The term "alkoxy", as used herein refers to an alkyl group, as previously defined, attached to the parent molecule through an oxygen atom. Examples of alkoxy, include but are not limited to, methoxy, ethoxy, propoxy, isopropoxy, n-butoxy, tert-butoxy, neopentoxy, and n-hexoxy.

The term "acyl", as used herein, refers to a carbonyl-containing functionality, e.g., —C(=O)R', wherein R' is hydrogen or an optionally substituted aliphatic, heteroaliphatic, heterocyclic, aryl, heteroaryl group, or is a substituted (e.g., with hydrogen or aliphatic, heteroaliphatic, aryl, or heteroaryl moieties) oxygen or nitrogen containing functionality (e.g., forming a carboxylic acid, ester, or amide functionality). The term "acyloxy", as used here, refers to an acyl group attached to the parent molecule through an oxygen atom.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like. In certain embodiments, the terms "6- to 10-membered aryl" and "$C_{6-10}$ aryl" refer to a phenyl or an 8- to 10-membered polycyclic aryl ring.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3- b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. In certain embodiments, the term "5- to 10-membered heteroaryl" refers to a 5- to 6-membered heteroaryl ring having 1 to 3 heteroatoms independently selected from nitrogen, oxygen, or sulfur, or an 8- to 10-membered bicyclic heteroaryl ring having 1 to 4 heteroatoms independently selected from nitrogen, oxygen, or sulfur. In certain embodiments, the term "5- to 12-membered heteroaryl" refers to a 5- to 6-membered heteroaryl ring having 1 to 3 heteroatoms independently selected from nitrogen, oxygen, or sulfur, or an 8- to 12-membered bicyclic heteroaryl ring having 1 to 4 heteroatoms independently selected from nitrogen, oxygen, or sulfur.

As used herein, the terms "heterocycle", "heterocyclyl", "heterocyclic radical", and "heterocyclic ring" are used interchangeably and refer to a stable 5- to 7-membered monocyclic or 7-14-membered polycyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). In some embodiments, the term "3- to 7-membered heterocyclic" refers to a 3- to 7-membered saturated or partially unsaturated monocyclic heterocyclic ring having 1 to 2 heteroatoms independently selected from nitrogen, oxygen, or sulfur. In some embodiments, the term "3- to 12-membered heterocyclic" refers to a 3- to 8-membered saturated or partially unsaturated monocyclic heterocyclic ring having 1 to 2 heteroatoms independently selected from nitrogen, oxygen, or sulfur, or a 7- to 12-membered saturated or partially unsaturated polycyclic heterocyclic ring having 1-3 heteroatoms independently selected from nitrogen, oxygen, or sulfur.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, molecules of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible molecules. The term "stable", as used herein, refers to molecules that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-4}Ph$ which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)N(R^\circ)_2$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR^\circ$—, $SC(S)SR^\circ$; —$(CH_2)_{0-4}SC(O)R^\circ$; —$(CH_2)_{0-4}C(O)NR^\circ_2$; —$C(S)NR^\circ$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-8}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or polycyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(haloR$^\bullet$), —$(CH_2)_2OH$, —$(CH_2)_{0-2}OR^\bullet$, —$(CH_2)_{0-2}CH(OR^\bullet)_2$; —O(haloR$^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-4}C(O)N(R^\bullet)_2$; —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)C(O)OR$^\bullet$, or —$SSR^\bullet$ wherein each $R^\bullet$ is unsubstituted or where preceded by "halo" is substituted only with one or more halogens, and is independently selected from $C_{1-4}$ aliphatic, —CH$_2$Ph, —O(CH$_2$)$_{0-1}$Ph. or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen. $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the "term head-to-tail" or "HT", refers to the regiochemistry of adjacent repeating units in a polymer chain. For example, in the context of poly(propylene carbonate) (PPC), the term head-to-tail based on the three regiochemical possibilities depicted below:

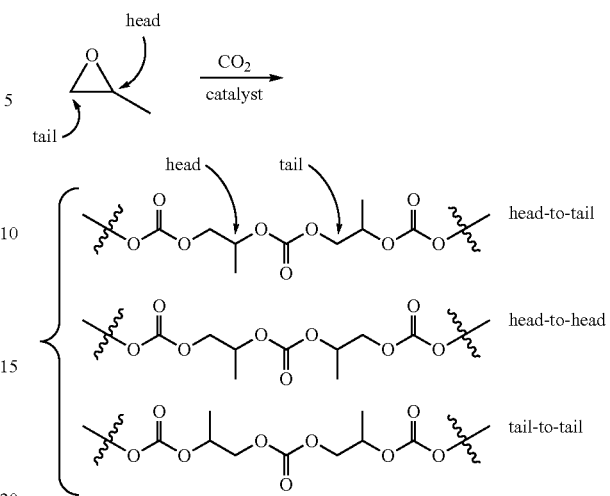

The term head-to-tail ratio (H:T) refers to the proportion of head-to-tail linkages to the sum of all other regiochemical possibilities. With respect to the depiction of polymer structures, while a specific regiochemical orientation of monomer units may be shown in the representations of polymer structures herein, this is not intended to limit the polymer structures to the regiochemical arrangement shown but is to be interpreted to encompass all regiochemical arrangements including that depicted, the opposite regiochemistry, random mixtures, isotactic materials, syndiotactic materials, racemic materials, and/or enantioenriched materials and combinations of any of these unless otherwise specified. Methods of ascertaining the regiochemistry of polymers including those described herein are well established in the art, for example by $^1$H or $^{13}$C NMR spectroscopy as described in Chisholm, et al. *J. Am. Chem. Soc.* 2004 (126), 11030-11039; Lu et al. *Angew. Chem. Int. Ed.* 2004 (43), 3574-3577; Chisholm, *Macromolecules* 2002 (35), 6494-6504; Wei, et al. *Macromolecules* 2013 (46), 3693-3697; and Taherimehr, *J. of Appl. Polym. Sci.* 2014, 41141.

As used herein the term "alkoxylated" means that one or more functional groups on a molecule (usually the functional group is an alcohol, amine, or carboxylic acid, but is not strictly limited to these) has appended to it a hydroxy-terminated alkyl chain. Alkoxylated molecules may comprise a single alkyl group or they may be oligomeric moieties such as hydroxyl-terminated polyethers. Alkoxylated materials can be derived from the parent molecules by treatment of the functional groups with epoxides.

As used herein, the term "isocyanate index" means the excess of isocyanate over the theoretical amount for (1:1) reaction with all active protons in a polyurethane composition, expressed in percentage terms (i.e., 1:1=100). Thus, isocyanate index=100×(Actual amount of isocyanate used)/(Theoretical amount of isocyanate required).

As used herein, the term "radiocarbon" or "radiocarbon content" refers to a radioactive isotope of carbon, $^{14}$C. When nitrogen in the atmosphere is struck by an ultraviolet light produced neutron, it loses a proton and forms carbon that has a molecular weight of 14, which is radioactive. This $^{14}$C is immediately oxidized into carbon dioxide, and represents a small, but measurable fraction of atmospheric carbon. Atmospheric carbon dioxide is cycled by green plants to make organic molecules during photosynthesis. The cycle is completed when the green plants or other forms of life metabolize the organic molecules producing carbon dioxide which is then able to return back to the atmosphere. Virtually all forms of life on Earth depend on this green plant production of organic molecules to produce the chemical energy that facilitates growth and reproduction. Therefore, the $^{14}C$ that exists in the atmosphere becomes part of all life forms and their biological products. In contrast, fossil fuel-based carbon does not have the signature radiocarbon ratio of atmospheric carbon dioxide. See PCT Publication No. WO 2009/155086, incorporated herein by reference.

As used herein, the term "fossil carbon" or "fossil-derived carbon" refers to carbon that contains essentially no radiocarbon because its age is very much greater than the 5,730 year half-life of $^{14}C$.

As used herein, the term "biomass" refers to materials containing organic carbon of renewable origin, like agricultural, plant, animal, fungi, microorganisms, marine, or forestry materials.

As used herein, the term "biobased" refers to atoms or molecules obtained from biomass, e.g., obtained from materials containing organic carbon of renewable origin like agricultural, plant, animal, fungi, microorganisms, marine, or forestry materials.

The "biobased carbon content" or "biobased content" of a material is measured using a method disclosed in ASTM D6866-16, which allows the determination of the biobased carbon content of materials using radiocarbon analysis by accelerator mass spectrometry along with Isotope Ratio Mass Spectrometry (described as "Method B" in ASTM D6866-16) or liquid scintillation counting (described as "Method C" in ASTM D6866-16). In general, the analysis is performed by deriving a ratio of the amount of radiocarbon ($^{14}C$) in an unknown sample to that of a modern reference standard, a NIST (National Institute of Standards and Technology) standard with a known radiocarbon content equivalent approximately to the year AD 1950. This ratio is reported as a percentage and referred to as "percent modern carbon" (i.e., "pMC"). Zero pMC represents the entire lack of measureable $^{14}C$ atoms in a molecule above the background signals thus indicating the molecule comprises exclusively fossil carbon. One hundred pMC indicates a molecule comprising entirely biobased carbon. A pMC value between 0 and 100 indicates a molecule comprising both fossil carbon and biobased carbon, and the pMC value obtained correlates directly to the amount of biobased carbon present in the sample.

The pMC can be greater than 100 due to the continuing, but diminishing effects from injection of $^{14}C$ into the atmosphere with atmospheric nuclear testing programs. The modern reference standard used in radiocarbon dating is a NIST standard with a known radiocarbon content equivalent approximately to the year AD 1950. The year AD 1950 was chosen because it represented a time prior to thermonuclear weapons testing which introduced large amounts of excess radiocarbon into the atmosphere with each explosion (termed "bomb carbon"). The AD 1950 reference represents 100 pMC. "Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. Because all sample $^{14}C$ activities are referenced to the pre-bomb NIST traceable standard, all pMC values must be adjusted by an atmospheric correction factor (REF) to obtain the true biobased content of the sample. The correction factor is based on the excess $^{14}C$ activity in the atmosphere at the time of testing. A REF value of 102 pMC was determined for 2015 based on the measurements of $CO_2$ in air in a rural area in the Netherlands (Lutjewad, Groningen). The first version of this standard (ASTM D6866-04) in 2004 referenced a value of 107.5 pMC and the ASTM 6866-10 version (2010) cited 105 pMC. These data points equate to a decline of 0.5 pMC per year. Therefore, on January 2 of each year, the values in Table 1 are used as REF through 2019, reflecting the same 0.5 pMC decrease per year.

TABLE 1

Percent Modern Carbon (pMC) Reference

| Year | REF (pMC) |
|------|-----------|
| 2015 | 102.0 |
| 2016 | 101.5 |
| 2017 | 101.0 |
| 2018 | 100.5 |
| 2019 | 100.0 |
| 2020 | to be determined |

Calculation of true % biobased carbon content is made by dividing pMC by REF and multiplying by 100. Results are reported as % biobased carbon.

Assessment of the materials described herein according to the present embodiments is performed in accordance with ASTM D6866 revision 16 (i.e., ASTM D6866-16), the entirety of which is incorporated herein by reference. In some embodiments, the assessments are performed according to the procedures of Method B of ASTM-D6866-16. The mean values encompass an absolute range of 6% (plus and minus 3% on either side of the biobased content value) to account for variations in end-component radiocarbon signatures. It is presumed that all materials are present day or fossil in origin and that the desired result is the amount of biobased carbon "present" in the material, not the amount of biobased carbon "used" in the manufacturing process.

Other techniques for assessing the biobased carbon content of materials are described in U.S. Pat. Nos. 3,885,155, 4,427,884, 4,973,841, 5,438,194, and 5,661,299, and PCT Publication No. WO 2009/155086, each of which is incorporated herein by reference.

DETAILED DESCRIPTION OF CERTAIN EMBODIMENTS

I. Polymer Compositions with Biobased and Fossil-Based Carbon

A. Polymer Compositions

In one aspect, the present invention provides polymer compositions that are both biobased and fossil-carbon sequestering. In some embodiments, the invention encompasses polymer compositions whose manufacture sequesters $CO_2$ produced from a fossil carbon source, and utilizes biobased feedstocks as constituents of the polymer chain.

In certain embodiments, a provided polymer composition comprises aliphatic polycarbonate polymers with biobased and fossil-based carbon. In certain embodiments, such provided polymer compositions comprise aliphatic polycarbonate polyols. In some embodiments, aliphatic polycarbonate polyols are derived from the copolymerization of one or more epoxides and carbon dioxide. Examples of aliphatic polycarbonate polyols derived from epoxides and $CO_2$ are disclosed in PCT Publication No. WO 2010/028362 the entirety of which is incorporated herein by reference.

In certain embodiments, the present invention provides a polymer composition comprising polymer chains having repeating units with a structure:

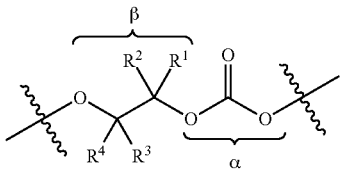

wherein:

R¹, R², R³, and R⁴ are, independently at each occurrence in the polymer chain, selected from the group consisting of: —H; and an optionally substituted group selected from $C_{1-30}$ aliphatic, and $C_{6-14}$ aryl; 3- to 12-membered heterocycle, and 5- to 12-membered heteroaryl, where two or more of R¹, R², R³, and R⁴ can be taken together with intervening atoms to form one or more optionally substituted 3- to 12-membered rings, optionally containing one or more heteroatoms; and the radiocarbon content of carbon atoms at positions labeled α is lower than the radiocarbon content of carbon atoms at positions labeled β.

In some embodiments, R¹ is —H. In some embodiments, R¹ is optionally substituted $C_{1-20}$ aliphatic. In some embodiments, R¹ is optionally substituted $C_{1-15}$ aliphatic. In some embodiments, R¹ is optionally substituted $C_{1-10}$ aliphatic. In some embodiments, R¹ is optionally substituted $C_{1-6}$ aliphatic. In some embodiments, R¹ is optionally substituted $C_{1-6}$ aliphatic. In some embodiments, R¹ is methyl. In some embodiments, R¹ is ethyl. In some embodiments, R¹ is —CH₂OR$^g$ where R$^g$ is selected from the group consisting of $C_{1-6}$ acyl, $C_{1-4}$ aliphatic, and optionally substituted aryl. In some embodiments, R¹ is optionally substituted $C_{6-14}$ aryl. In some embodiments, R¹ is optionally substituted phenyl.

In some embodiments, R² is —H. In some embodiments, R² is optionally substituted $C_{1-20}$ aliphatic. In some embodiments, R² is optionally substituted $C_{1-15}$ aliphatic. In some embodiments, R² is optionally substituted $C_{1-10}$ aliphatic. In some embodiments, R² is optionally substituted $C_{1-6}$ aliphatic. In some embodiments, R² is optionally substituted $C_{1-4}$ aliphatic. In some embodiments, R² is methyl. In some embodiments, R² is ethyl. In some embodiments. R² is —CH₂OR$^g$ where R$^g$ is selected from the group consisting of $C_{1-6}$ acyl, $C_{1-8}$ aliphatic, and optionally substituted aryl. In some embodiments, R² is optionally substituted $C_{6-14}$ aryl. In some embodiments, R² is optionally substituted phenyl.

In some embodiments, R³ is —H. In some embodiments, R³ is optionally substituted $C_{1-20}$ aliphatic. In some embodiments, R³ is optionally substituted $C_{1-15}$ aliphatic. In some embodiments, R³ is optionally substituted $C_{1-10}$ aliphatic. In some embodiments, R³ is optionally substituted $C_{1-6}$ aliphatic. In some embodiments, R³ is optionally substituted $C_{1-4}$ aliphatic. In some embodiments, R³ is methyl. In some embodiments, R³ is ethyl. In some embodiments, R³ is —CH₂OR$^g$ where R$^g$ is selected from the group consisting of $C_{1-6}$ acyl, $C_{1-8}$ aliphatic, and optionally substituted aryl. In some embodiments, R³ is optionally substituted $C_{6-14}$ aryl. In some embodiments, R³ is optionally substituted phenyl.

In some embodiments, R⁴ is —H. In some embodiments, R⁴ is optionally substituted $C_{1-20}$ aliphatic. In some embodiments, R⁴ is optionally substituted $C_{1-6}$ aliphatic. In some embodiments, R⁴ is optionally substituted $C_{1-10}$ aliphatic. In some embodiments, R⁴ is optionally substituted $C_{1-6}$ aliphatic. In some embodiments, R⁴ is optionally substituted $C_{1-4}$ aliphatic. In some embodiments, R⁴ is methyl. In some embodiments, R⁴ is ethyl. In some embodiments, R⁴ is —CH₂OR$^g$ where R$^g$ is selected from the group consisting of $C_{1-6}$ acyl, $C_{1-8}$ aliphatic, and optionally substituted aryl. In some embodiments, R⁴ is optionally substituted $C_{6-14}$ aryl. In some embodiments, R⁴ is optionally substituted phenyl.

In some embodiments, each of R¹, R², R³, and R⁴ are —H. In some embodiments, one of R¹, R², R³, and R⁴ is methyl, and the remaining three are —H.

In some embodiments, polymer composition comprising polymer chains having repeating units with a structure:

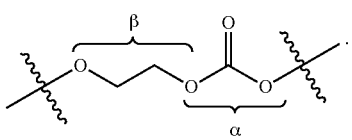

In some embodiments, polymer composition comprising polymer chains having repeating units with a structure:

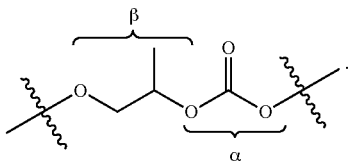

In some embodiments, polymer composition comprising polymer chains having repeating units with a structure:

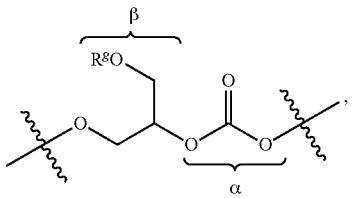

where R$^g$ is as defined above and in the embodiments herein.

In some embodiments, the radiocarbon content of carbon atoms at positions labeled α is lower than the radiocarbon content of carbon atoms at positions labeled β.

In some embodiments, the radiocarbon content of carbon atoms at positions labeled α is at least 5% lower than the radiocarbon content of carbon atoms at positions labeled β. In some embodiments, the radiocarbon content of carbon atoms at positions labeled α is at least 10% lower than the radiocarbon content of carbon atoms at positions labeled β. In some embodiments, the radiocarbon content of carbon atoms at positions labeled α is at least 15% lower than the radiocarbon content of carbon atoms at positions labeled β. In some embodiments, the radiocarbon content of carbon atoms at positions labeled α is at least 20% lower than the radiocarbon content of carbon atoms at positions labeled β. In some embodiments, the radiocarbon content of carbon atoms at positions labeled α is at least 25% lower than the radiocarbon content of carbon atoms at positions labeled β. In some embodiments, the radiocarbon content of carbon atoms at positions labeled α is at least 30% lower than the radiocarbon content of carbon atoms at positions labeled β. In some embodiments, the radiocarbon content of carbon atoms at positions labeled α is at least 35% lower than the radiocarbon content of carbon atoms at positions labeled β. In some embodiments, the radiocarbon content of carbon atoms at positions labeled α is at least 40% lower than the radiocarbon content of carbon atoms at positions labeled β. In some embodiments, the radiocarbon content of carbon atoms at positions labeled α is at least 45% lower than the radiocarbon content of carbon atoms at positions labeled β. In some embodiments, the radiocarbon content of carbon atoms at positions labeled α is at least 50% lower than the radiocarbon content of carbon atoms at positions labeled β. In some embodiments, the radiocarbon content of carbon atoms at positions labeled α is at least 55% lower than the radiocarbon content of carbon atoms at positions labeled β. In some embodiments, the radiocarbon content of carbon atoms at positions labeled α is at least 60% lower than the radiocarbon content of carbon atoms at positions labeled β. In some embodiments, the radiocarbon content of carbon atoms at positions labeled α is at least 65% lower than the radiocarbon content of carbon atoms at positions labeled β. In some embodiments, the radiocarbon content of carbon atoms at positions labeled α is at least 70% lower than the radiocarbon content of carbon atoms at positions labeled β. In some embodiments, the radiocarbon content of carbon atoms at positions labeled α is at least 75% lower than the radiocarbon content of carbon atoms at positions labeled β. In some embodiments, the radiocarbon content of carbon atoms at positions labeled α is at least 80% lower than the radiocarbon content of carbon atoms at positions labeled β. In some embodiments, the radiocarbon content of carbon atoms at positions labeled α is at least 85% lower than the radiocarbon content of carbon atoms at positions labeled β. In some embodiments, the radiocarbon content of carbon atoms at positions labeled α is at least 90% lower than the radiocarbon content of carbon atoms at positions labeled β. In some embodiments, the radiocarbon content of carbon atoms at positions labeled α is at least 95% lower than the radiocarbon content of carbon atoms at positions labeled β.

In some embodiments, a polymer composition comprises polymer chains characterized in that the carbon atoms at positions labeled α have a pMC value measured according to ASTM D6866-16 (Method B) that is lower than a pMC value of the carbon atoms at positions labeled β.

In some embodiments, the carbon atoms at positions labeled α have a pMC value measured according to ASTM D6866-16 (Method B) of less than about 50. In some embodiments, the carbon atoms at positions labeled α have a pMC value measured according to ASTM D6866-16 (Method B) of less than about 45. In some embodiments, the carbon atoms at positions labeled α have a pMC value of less than about 40. In some embodiments, the carbon atoms at positions labeled α have a pMC value measured according to ASTM D6866-16 (Method B) of less than about 35. In some embodiments, the carbon atoms at positions labeled α have a pMC value of less than about 30. In some embodiments, the carbon atoms at positions labeled α have a pMC value measured according to ASTM D6866-16 (Method B) of less than about 25. In some embodiments, the carbon atoms at positions labeled α have a pMC value measured according to ASTM D6866-16 (Method B) of less than about 20. In some embodiments, the carbon atoms at positions labeled α have a pMC value measured according to ASTM D6866-16 (Method B) of less than about 15. In some embodiments, the carbon atoms at positions labeled α have a pMC value measured according to ASTM D6866-16 (Method B) of less than about 10. In some embodiments, the carbon atoms at positions labeled α have a pMC value measured according to ASTM D6866-16 (Method B) of less than about 5. In some embodiments, the carbon atoms at positions labeled α have a pMC value measured according to ASTM D6866-16 (Method B) of less than about 1. In some embodiments, the carbon atoms at positions labeled α have a pMC value measured according to ASTM D6866-16 (Method B) of less than about 0.1. In some embodiments, the carbon atoms at positions labeled α have a pMC value measured according to ASTM D6866-16 (Method B) of less than about 0.01. In some embodiments, the carbon atoms at positions labeled α have a pMC value measured according to ASTM D6866-16 (Method B) of about 0.

In some embodiments, the carbon atoms at positions labeled α have a pMC value measured according to ASTM D6866-16 (Method B) of between about 0 and about 10. In some embodiments, the carbon atoms at positions labeled α have a pMC value measured according to ASTM D6866-16 (Method B) of between about 0 and about 1. In some embodiments, the carbon atoms at positions labeled α have a pMC value measured according to ASTM D6866-16 (Method B) of between about 0 and about 0.1. In some embodiments, the carbon atoms at positions labeled α have a pMC value measured according to ASTM D6866-16 (Method B) of between about 0 and about 0.01. In some embodiments, the carbon atoms at positions labeled α have a pMC value measured according to ASTM D6866-16 (Method B) of between about 0 and about 5. In some embodiments, the carbon atoms at positions labeled α have a pMC value measured according to ASTM D6866-16 (Method B) of between about 5 and about 10.

In some embodiments, the carbon atoms at positions labeled α have a pMC value measured according to ASTM D6866-16 (Method B) of about 50. In some embodiments, the carbon atoms at positions labeled α have a pMC value measured according to ASTM D6866-16 (Method B) of about 45. In some embodiments, the carbon atoms at positions labeled α have a pMC value measured according to ASTM D6866-16 (Method B) of about 40. In some embodiments, the carbon atoms at positions labeled α have a pMC value measured according to ASTM D6866-16 (Method B) of about 35. In some embodiments, the carbon atoms at positions labeled α have a pMC value measured according to ASTM D6866-16 (Method B) of about 30. In some embodiments, the carbon atoms at positions labeled α have a pMC value measured according to ASTM D6866-16 (Method B) of about 25. In some embodiments, the carbon atoms at positions labeled α have a pMC value measured according to ASTM D6866-16 (Method B) of about 20. In some embodiments, the carbon atoms at positions labeled α have a pMC value measured according to ASTM D6866-16 (Method B) of about 15. In some embodiments, the carbon atoms at positions labeled α have a pMC value measured according to ASTM D6866-16 (Method B) of about 10. In some embodiments, the carbon atoms at positions labeled α have a pMC value measured according to ASTM D6866-16 (Method B) of about 5. In some embodiments, the carbon atoms at positions labeled α have a pMC value measured according to ASTM D6866-16 (Method B) of about 1. In some embodiments, the carbon atoms at positions labeled α have a pMC value measured according to ASTM D6866-16 (Method B) of about 0.1. In some embodiments, the carbon atoms at positions labeled α have a pMC value measured according to ASTM D6866-16 (Method B) of about 0.01. In some embodiments, the carbon atoms at positions labeled α have a pMC value measured according to ASTM D6866-16 (Method B) of about 0.

In some embodiments, the carbon atoms at positions labeled β have a pMC value measured according to ASTM D6866-16 (Method B) of greater than about 75. In some embodiments, the carbon atoms at positions labeled β have a pMC value measured according to ASTM D6866-16 (Method B) of greater than about 80. In some embodiments, the carbon atoms at positions labeled β have a pMC value measured according to ASTM D6866-16 (Method B) of greater than about 85. In some embodiments, the carbon atoms at positions labeled β have a pMC value measured according to ASTM D6866-16 (Method B) of greater than about 90. In some embodiments, the carbon atoms at positions labeled β have a pMC value measured according to ASTM D6866-16 (Method B) of greater than about 95. In some embodiments, the carbon atoms at positions labeled β have a pMC value measured according to ASTM D6866-16 (Method B) of greater than about 100. In some embodiments, the carbon atoms at positions labeled β have a pMC value measured according to ASTM D6866-16 (Method B) of greater than about 105.

In some embodiments, the carbon atoms at positions labeled β have a pMC value measured according to ASTM D6866-16 (Method B) of between about 75 and about 107.5. In some embodiments, the carbon atoms at positions labeled β have a pMC value measured according to ASTM D6866-16 (Method B) of between about 85 and about 107.5. In some embodiments, the carbon atoms at positions labeled β have a pMC value measured according to ASTM D6866-16 (Method B) of between about 95 and about 107.5. In some embodiments, the carbon atoms at positions labeled β have a pMC value measured according to ASTM D6866-16 (Method B) of between about 105 and about 107.5. In some embodiments, the carbon atoms at positions labeled β have a pMC value measured according to ASTM D6866-16 (Method B) of between about 75 and about 100. In some embodiments, the carbon atoms at positions labeled β have a pMC value measured according to ASTM D6866-16 (Method B) of between about 75 and about 85. In some embodiments, the carbon atoms at positions labeled β have a pMC value measured according to ASTM D6866-16 (Method B) of between about 85 and about 105. In some embodiments, the carbon atoms at positions labeled β have a pMC value measured according to ASTM D6866-16 (Method B) of between about 95 and about 105.

In some embodiments, the carbon atoms at positions labeled β have a pMC value measured according to ASTM D6866-16 (Method B) of about 75. In some embodiments, the carbon atoms at positions labeled β have a pMC value measured according to ASTM D6866-16 (Method B) of about 80. In some embodiments, the carbon atoms at positions labeled β have a pMC value measured according to ASTM D6866-16 (Method B) of about 85. In some embodiments, the carbon atoms at positions labeled β have a pMC value measured according to ASTM D6866-16 (Method B) of about 90. In some embodiments, the carbon atoms at positions labeled β have a pMC value measured according to ASTM D6866-16 (Method B) of about 95. In some embodiments, the carbon atoms at positions labeled β have a pMC value measured according to ASTM D6866-16 (Method B) of about 100. In some embodiments, the carbon atoms at positions labeled β have a pMC value measured according to ASTM D6866-16 (Method B) of about 105. In some embodiments, the carbon atoms at positions labeled β have a pMC value measured according to ASTM D6866-16 (Method B) of about 107.5.

In some embodiments, a polymer composition comprises greater than about 10% biobased carbon content. In some embodiments, a polymer composition comprises greater than about 20% biobased carbon content. In some embodiments, a polymer composition comprises greater than about 30% biobased carbon content. In some embodiments, a polymer composition comprises greater than about 40% biobased carbon content. In some embodiments, a polymer composition comprises greater than about 50% biobased carbon content. In some embodiments, a polymer composition comprises greater than about 60% biobased carbon content. In some embodiments, a polymer composition comprises greater than about 70% biobased carbon content. In some embodiments, a polymer composition comprises greater than about 80% biobased carbon content. In some embodiments, a polymer composition comprises greater than about 90% biobased carbon content. In some embodiments, a polymer composition comprises greater than about 95% biobased carbon content. In some embodiments, a polymer composition comprises greater than about 98% biobased carbon content. In some embodiments, a polymer composition comprises greater than about 99% biobased carbon content.

In some embodiments, a polymer composition comprises less than about 90% biobased carbon content. In some embodiments, a polymer composition comprises less than about 80% biobased carbon content. In some embodiments, a polymer composition comprises less than about 70% biobased carbon content. In some embodiments, a polymer composition comprises less than about 60% biobased carbon content. In some embodiments, a polymer composition comprises less than about 50% biobased carbon content. In some embodiments, a polymer composition comprises less than about 400% biobased carbon content. In some embodiments, a polymer composition comprises less than about 30% biobased carbon content. In some embodiments, a polymer composition comprises less than about 20% biobased carbon content. In some embodiments, a polymer composition comprises less than about 10% biobased carbon content.

In some embodiments, a polymer composition comprises between about 10% and about 90% biobased carbon content. In some embodiments, a polymer composition comprises between about 20% and about 90% biobased carbon content. In some embodiments, a polymer composition comprises between about 30% and about 90% biobased carbon content. In some embodiments, a polymer composition comprises between about 40% and about 90% biobased carbon content. In some embodiments, a polymer composition comprises between about 50% and about 90% biobased carbon content. In some embodiments, a polymer composition comprises between about 10% and about 80% biobased carbon content. In some embodiments, a polymer composition comprises between about 10% and about 70% biobased carbon content. In some embodiments, a polymer composition comprises between about 10% and about 60% biobased carbon content. In some embodiments, a polymer composition comprises between about 10% and about 50% biobased carbon content. In some embodiments, a polymer composition comprises between about 20% and about 80% biobased carbon content. In some embodiments, a polymer composition comprises between about 30% and about 70% biobased carbon content. In some embodiments, a polymer composition comprises between about 40% and about 60% biobased carbon content.

In some embodiments, a polymer composition comprises between about 45% and about 55% biobased carbon content. In some embodiments, a polymer composition comprises between about 45% and about 65% biobased carbon content. In some embodiments, a polymer composition comprises between about 50% and about 70% biobased carbon content. In some embodiments, a polymer composition comprises between about 60% and about 80% biobased carbon content. In some embodiments, a polymer composition comprises between about 70% and about 80% biobased carbon content. In some embodiments, a polymer composition comprises between about 65% and about 85% biobased carbon content. In some embodiments, a polymer composition comprises between about 75% and about 85% biobased carbon content. In some embodiments, a polymer composition comprises between about 65% and about 75% biobased carbon content. In some embodiments, a polymer composition comprises between about 55% and about 65% biobased carbon content.

In some embodiments, all of the carbon atoms at the positions labeled α are derived from $CO_2$ sequestered from a fossil carbon source, and all of the carbon atoms at the positions labeled β are derived from a biobased epoxide.

In some embodiments, at least about 50% of the carbon atoms at the positions labeled α are derived from $CO_2$ sequestered from a fossil carbon source. In some embodiments, at least about 60% of the carbon atoms at the positions labeled α are derived from $CO_2$ sequestered from a fossil carbon source. In some embodiments, at least about 70% of the carbon atoms at the positions labeled α are derived from $CO_2$ sequestered from a fossil carbon source. In some embodiments, at least about 80% of the carbon atoms at the positions labeled α are derived from $CO_2$ sequestered from a fossil carbon source. In some embodiments, at least about 90% of the carbon atoms at the positions labeled α are derived from $CO_2$ sequestered from a fossil carbon source. In some embodiments, at least about 95% of the carbon atoms at the positions labeled α are derived from $CO_2$ sequestered from a fossil carbon source. In some embodiments, at least about 96% of the carbon atoms at the positions labeled α are derived from $CO_2$ sequestered from a fossil carbon source. In some embodiments, at least about 97% of the carbon atoms at the positions labeled α are derived from $CO_2$ sequestered from a fossil carbon source. In some embodiments, at least about 98% of the carbon atoms at the positions labeled α are derived from $CO_2$ sequestered from a fossil carbon source. In some embodiments, at least about 99% of the carbon atoms at the positions labeled α are derived from $CO_2$ sequestered from a fossil carbon source. In some embodiments, at least about 99.5% of the carbon atoms at the positions labeled α are derived from $CO_2$ sequestered from a fossil carbon source.

In some embodiments, at least about 50% of the carbon atoms at the positions labeled β are derived from a biobased epoxide. In some embodiments, at least about 60% of the carbon atoms at the positions labeled β are derived from a biobased epoxide. In some embodiments, at least about 70% of the carbon atoms at the positions labeled β are derived from a biobased epoxide. In some embodiments, at least about 80% of the carbon atoms at the positions labeled β are derived from a biobased epoxide. In some embodiments, at least about 90% of the carbon atoms at the positions labeled β are derived from a biobased epoxide. In some embodiments, at least about 95% of the carbon atoms at the positions labeled β are derived from a biobased epoxide. In some embodiments, at least about 96% of the carbon atoms at the positions labeled β are derived from a biobased epoxide. In some embodiments, at least about 97% of the carbon atoms at the positions labeled β are derived from a biobased epoxide. In some embodiments, at least about 98% of the carbon atoms at the positions labeled β are derived from a biobased epoxide. In some embodiments, at least about 99% of the carbon atoms at the positions labeled β are derived from a biobased epoxide. In some embodiments, at least about 99.5% of the carbon atoms at the positions labeled β are derived from a biobased epoxide.

In some embodiments, biobased epoxides are selected from the group consisting of ethylene oxide, propylene oxide, epoxides derived from natural oils, epoxides derived from fatty acids, epoxides derived from fatty alcohols, epoxides derived from terpenes, and mixtures of any two or more of these. In some embodiments, biobased epoxides are selected from the group consisting of ethylene oxide, propylene oxide, glycidol ethers, glycidol esters, and limonene oxide. In some embodiments, biobased epoxides are ethylene oxide or propylene oxide. In some embodiments, biobased epoxides are ethylene oxide. In some embodiments, biobased epoxides are propylene oxide. In some embodiments, biobased epoxides are limonene oxide.

In some embodiments, a biobased epoxide is an epoxide derived from a terpene. In some embodiments, a biobased epoxide derived from a terpene is selected from the group consisting of limonene oxide and α-pinene oxide.

In some embodiments, a biobased epoxide is an epoxide derived from plant oils. In some embodiments, a biobased epoxide derived from plant oils is selected from the group consisting of 1,4-cyclohexadiene, cyclohexene, methyl-9,10-epoxystearate, and 18-hydroxy-9,10-epoxyoctadecanoate.

In some embodiments, a biobased epoxide is an epoxide derived from glycerol. In some embodiments, a biobased epoxide derived from glycerol is selected from the group consisting of glycidol, glycidol ethers, glycidol esters, and epichlorohydrin. In certain embodiments where the epoxide comprises a glycidol ether or ester, such ethers and esters are derived by combining glycidol with a biobased alcohol or carboxylic acid respectively (or a reactive derivative of such a biobased alcohol or carboxylic acid).

In some embodiments, biobased epoxides include epoxides derived from naturally occurring materials such as epoxidized resins or oils. Examples of such epoxides include, but are not limited to: Epoxidized Soybean Oil; Epoxidized Linseed Oil; Epoxidized Octyl Soyate; Epoxidized PGDO; Methyl Epoxy Soyate; Butyl Epoxy Soyate; Epoxidized Octyl Soyate; Methyl Epoxy Linseedate; Butyl Epoxy Linseedate; and Octyl Epoxy Linseedate. These and similar materials are available commercially from Arkema Inc. under the trade name Vikoflex®. Examples of such commercially available Vikoflex® materials include Vikoflex 7170 Epoxidized Soybean Oil, Vikoflex 7190 Epoxidized Linseed, Vikoflex 4050 Epoxidized Octyl Soyate, Vikoflex 5075 Epoxidized PGDO, Vikoflex 7010 Methyl Epoxy Soyate, Vikoflex 7040 Butyl Epoxy Soyate, Vikoflex 7080 Epoxidized Octyl Soyate, Vikoflex 9010 Methyl Epoxy Linseedate, Vikoflex 9040 Butyl Epoxy Linseedate, and Vikoflex 9080 Octyl Epoxy Linseedate.

In certain embodiments, polymer chains comprise aliphatic polycarbonate polymers derived from fossil-based carbon dioxide and one or more epoxides, wherein at least one of the epoxides is a biobased epoxide. In certain embodiments, aliphatic polycarbonate chains comprise a copolymer of fossil-based carbon dioxide and biobased ethylene oxide. In certain embodiments, aliphatic polycarbonate chains comprise a copolymer of fossil-based carbon dioxide and biobased propylene oxide.

In certain embodiments, aliphatic polycarbonate chains comprise a terpolymer of carbon dioxide and biobased ethylene oxide along with one or more additional epoxides selected from the group consisting of propylene oxide, 1,2-butene oxide, 2,3-butene oxide, cyclohexene oxide, 3-vinyl cyclohexene oxide, 3-ethyl cyclohexene oxide, cyclopentene oxide, epichlorohydrin, limonene oxide, glicydyl esters, glycidyl ethers, styrene oxides, and epoxides of higher alpha olefins. In certain embodiments, such terpolymers contain a majority of repeat units derived from biobased ethylene oxide with lesser amounts of repeat units derived from one or more additional epoxides. In certain embodiments, terpolymers contain about 50% to about 99.5% biobased ethylene oxide-derived repeat units. In certain embodiments, terpolymers contain greater than about 60% biobased ethylene oxide-derived repeat units. In certain embodiments, terpolymers contain greater than 75% biobased ethylene oxide-derived repeat units. In certain embodiments, terpolymers contain greater than 80% biobased ethylene oxide-derived repeat units. In certain embodiments, terpolymers contain greater than 85% biobased ethylene oxide-derived repeat units. In certain embodiments, terpolymers contain greater than 90% biobased ethylene oxide-derived repeat units. In certain embodiments, terpolymers contain greater than 95% biobased ethylene oxide-derived repeat units.

In certain embodiments, the aliphatic polycarbonate chains comprise a copolymer of carbon dioxide and biobased propylene oxide along with one or more additional epoxides selected from the group consisting of ethylene oxide, 1,2-butene oxide, 2,3-butene oxide, cyclohexene oxide, 3-vinyl cyclohexene oxide, cyclopentene oxide, epichlorohydrin, limonene oxide, glicydyl esters, glycidyl ethers, styrene oxides, and epoxides of higher alpha olefins. In certain embodiments, such terpolymers contain a majority of repeat units derived from biobased propylene oxide with lesser amounts of repeat units derived from one or more additional epoxides. In certain embodiments, terpolymers contain about 50% to about 99.5% biobased propylene oxide-derived repeat units. In certain embodiments, terpolymers contain greater than 60% biobased propylene oxide-derived repeat units. In certain embodiments, terpolymers contain greater than 75% biobased propylene oxide-derived repeat units. In certain embodiments, terpolymers contain greater than 80% biobased propylene oxide-derived repeat units. In certain embodiments, terpolymers contain greater than 85% biobased propylene oxide-derived repeat units. In certain embodiments, terpolymers contain greater than 90% biobased propylene oxide-derived repeat units. In certain embodiments, terpolymers contain greater than 95% biobased propylene oxide-derived repeat units.

In certain embodiments, the aliphatic polycarbonate chains comprise a copolymer of carbon dioxide and biobased limonene oxide along with one or more additional epoxides selected from the group consisting of ethylene oxide, propylene oxide, 1,2-butene oxide, 2,3-butene oxide, cyclohexene oxide, 3-vinyl cyclohexene oxide, cyclopentene oxide, epichlorohydrin, glicydyl esters, glycidyl ethers, styrene oxides, and epoxides of higher alpha olefins. In certain embodiments, such terpolymers contain a majority of repeat units derived from biobased limonene oxide with lesser amounts of repeat units derived from one or more additional epoxides. In certain embodiments, terpolymers contain about 50% to about 99.5% biobased limonene oxide-derived repeat units. In certain embodiments, terpolymers contain greater than 60% biobased limonene oxide-derived repeat units. In certain embodiments, terpolymers contain greater than 75% biobased limonene oxide-derived repeat units. In certain embodiments, terpolymers contain greater than 80% biobased limonene oxide-derived repeat units. In certain embodiments, terpolymers contain greater than 85% biobased limonene oxide-derived repeat units. In certain embodiments, terpolymers contain greater than 90% biobased limonene oxide-derived repeat units. In certain embodiments, terpolymers contain greater than 95% biobased limonene oxide-derived repeat units.

It is advantageous for many of the embodiments described herein that aliphatic polycarbonate polyols used herein have a high percentage of reactive end groups. Such reactive end-groups are typically hydroxyl groups, but other reactive functional groups may be present if the polyols are treated to modify the chemistry of the end groups, such modified materials may terminate in amino groups, thiol groups, alkene groups, carboxylate groups, isocyanate groups, silyl groups, epoxy groups and the like. For purposes of this invention, the term "aliphatic polycarbonate polyol" includes both traditional hydroxy-terminated materials as well as these end-group modified compositions.

In certain embodiments, aliphatic polycarbonate polyols utilized herein are characterized in that at least 90% of the end groups are reactive groups. In certain embodiments, aliphatic polycarbonate polyols utilized herein are characterized in that at least 95% of the end groups are reactive groups. In certain embodiments, aliphatic polycarbonate polyols utilized herein are characterized in that at least 96% of the end groups are reactive groups. In certain embodiments, aliphatic polycarbonate polyols utilized herein are characterized in that at least 97% of the end groups are reactive groups. In certain embodiments, aliphatic polycarbonate polyols utilized herein are characterized in that at least 98% of the end groups are reactive groups. In certain embodiments, aliphatic polycarbonate polyols utilized herein are characterized in that at least 99% of the end groups are reactive groups. In certain embodiments, aliphatic polycarbonate polyols utilized herein are characterized in that at least 99.5% of the end groups are reactive groups. In certain embodiments, aliphatic polycarbonate polyols utilized herein are characterized in that at least 99.7% of the end groups are reactive groups. In certain embodiments, aliphatic polycarbonate polyols utilized herein are characterized in that at least 99.8% of the end groups are reactive groups. In certain embodiments, aliphatic polycarbonate polyols utilized herein are characterized in that at least 99.9% of the end groups are reactive groups.

In certain embodiments, aliphatic polycarbonate polyols utilized herein are characterized in that at least 90% of the end groups are —OH groups. In certain embodiments, aliphatic polycarbonate polyols utilized herein are characterized in that at least 95% of the end groups are —OH groups. In certain embodiments, aliphatic polycarbonate polyols utilized herein are characterized in that at least 96% of the end groups are —OH groups. In certain embodiments, aliphatic polycarbonate polyols utilized herein are characterized in that at least 97% of the end groups are —OH groups. In certain embodiments, aliphatic polycarbonate polyols utilized herein are characterized in that at least 98% of the end groups are —OH groups. In certain embodiments, aliphatic polycarbonate polyols utilized herein are characterized in that at least 99% of the end groups are —OH groups. In certain embodiments, aliphatic polycarbonate polyols utilized herein are characterized in that at least 99.5% of the end groups are —OH groups. In certain embodiments, aliphatic polycarbonate polyols utilized herein are characterized in that at least 99.7% of the end groups are —OH groups. In certain embodiments, aliphatic polycarbonate polyols utilized herein are characterized in that at least 99.8% of the end groups are —OH groups. In certain embodiments, aliphatic polycarbonate polyols utilized herein are characterized in that at least 99.9% of the end groups are —OH groups.

In certain embodiments, aliphatic polycarbonate polyols utilized herein have an "OH number" (OH #) greater than about 20 as measured using methods well known in the art. In certain embodiments, aliphatic polycarbonate polyols utilized herein have an OH # greater than about 40. In certain embodiments, the aliphatic polycarbonate polyols utilized herein have an OH # greater than about 50, greater than about 75, greater than about 100, or greater than about 120.

In certain embodiments, it is advantageous if the aliphatic polycarbonate polyols utilized herein have a substantial proportion of primary hydroxyl end groups. These are the norm for compositions comprising poly(ethylene carbonate), but for polyols derived from copolymerization of substituted epoxides with $CO_2$, it is common for some or most of the chain ends to consist of secondary hydroxyl groups. In certain embodiments, such polyols are treated to increase the proportion of primary —OH end groups. This may be accomplished by reacting the secondary hydroxyl groups with reagents such as ethylene oxide, reactive lactones, and the like. In certain embodiments, the aliphatic polycarbonate polyols are treated with beta lactones, caprolactone and the like to introduce primary hydroxyl end groups. In certain embodiments, the aliphatic polycarbonate polyols are treated with ethylene oxide to introduce primary hydroxyl end groups. In certain embodiments, the aliphatic polycarbonate polyols are treated with biobased ethylene oxide to introduce primary hydroxyl end groups.

In certain embodiments, in the aliphatic polymer compositions described above and herein, polycarbonate chains have a Mn in the range of 500 g/mol to about 250,000 g/mol. In some embodiments, Mn is measured by size-exclusion chromatography. In some embodiments, Mn is measured by gel permeation chromatography. In some embodiments, gel permeation chromatography comprises a polystyrene standard.

In certain embodiments, polymer compositions described herein have a Mn greater than about 100,000 g/mol. In certain embodiments, polymer compositions described herein have a Mn less than about 100,000 g/mol. In certain embodiments, polymer compositions described herein have a Mn less than about 70,000 g/mol. In certain embodiments, polymer compositions described herein have a Mn less than about 50,000 g/mol. In certain embodiments, polymer compositions described herein have a Mn between about 500 g/mol and about 40,000 g/mol. In certain embodiments, polymer compositions described herein have a Mn less than about 25,000 g/mol. In certain embodiments, polymer compositions described herein have a Mn between about 500 g/mol and about 20,000 g/mol. In certain embodiments, polymer compositions described herein have a Mn between about 500 g/mol and about 10,000 g/mol. In certain embodiments, polymer compositions described herein have a Mn between about 500 g/mol and about 5,000 g/mol. In certain embodiments, polymer compositions described herein have a Mn between about 1,000 g/mol and about 5,000 g/mol. In certain embodiments, polymer compositions described herein have a Mn between about 5,000 g/mol and about 10,000 g/mol. In certain embodiments, polymer compositions described herein have a Mn between about 500 g/mol and about 1,000 g/mol. In certain embodiments, polymer compositions described herein have a Mn between about 1,000 g/mol and about 3,000 g/mol. In certain embodiments, polymer compositions described herein have a Mn of about 5,000 g/mol. In certain embodiments, polymer compositions described herein have a Mn of about 4,000 g/mol. In certain embodiments, polymer compositions described herein have a Mn of about 3,000 g/mol. In certain embodiments, polymer compositions described herein have a Mn of about 2,500 g/mol. In certain embodiments, polymer compositions described herein have a Mn of about 2,000 g/mol. In certain embodiments, polymer compositions described herein have a Mn of about 1,500 g/mol. In certain embodiments, polymer compositions described herein have a Mn of about 1,000 g/mol. In certain embodiments, polymer compositions described herein have a Mn of about 750 g/mol. In certain embodiments, polymer compositions described herein have a Mn of about 500 g/mol.

In certain embodiments, polymer compositions of the present invention are characterized in that they have a narrow molecular weight distribution. This can be indicated by the polydispersity indices (PDI) of the polymer composition. In certain embodiments, polymer compositions described herein have a PDI less than 3. In certain embodiments, polymer compositions described herein have a PDI less than 2. In certain embodiments, polymer compositions described herein have a PDI less than 1.8. In certain embodiments, polymer compositions described herein have a PDI less than 1.5. In certain embodiments, polymer compositions described herein have a PDI less than 1.4. In certain embodiments, polymer compositions described herein have a PDI between about 1.0 and 1.2. In certain embodiments, polymer compositions described herein have a PDI between about 1.0 and 1.1.

In certain embodiments, polymer compositions of the present invention do not have a narrow PDI. This can be the case if, for example, a polydisperse chain transfer agent is used to initiate an epoxide $CO_2$ copolymerization, or if a plurality of polymer compositions with different molecular weights are blended. In certain embodiments, polymer compositions described herein have a PDI greater than 3. In certain embodiments, polymer compositions described herein have a PDI greater than 2. In certain embodiments, polymer compositions described herein have a PDI greater than 1.8. In certain embodiments, polymer compositions described herein have a PDI greater than 1.5. In certain embodiments, polymer compositions described herein have a PDI greater than 1.4. In certain embodiments, the head-to-tail content of the polymer is as determined by size exclusion chromatography.

In certain embodiments, there an aliphatic polycarbonate is derived from mono-substituted epoxides (e.g., such as propylene oxide, 1,2-butylene oxide, epichlorohydrin, epoxidized alpha olefins, or a glycidol derivative), the aliphatic polycarbonate is characterized in that it is regioregular. Regioregularity may be expressed as the percentage of adjacent monomer units that are oriented in a head-to-tail arrangement within the polymer chain. In certain embodiments, aliphatic polycarbonate chains in the inventive polymer compositions have a head-to-tail content higher than about 80%. In certain embodiments, the head-to-tail content is higher than about 85%. In certain embodiments, the head-to-tail content is higher than about 90%. In certain embodiments, the head-to-tail content is greater than about 91%, greater than about 92/%, greater than about 93%, greater than about 94%, or greater than about 95%.

In some embodiments, PDI is measured by size-exclusion chromatography. In some embodiments, PDI is measured by gel permeation chromatography. In some embodiments, gel permeation chromatography comprises a polystyrene standard.

i. Substantially Alternating Aliphatic Polycarbonate Polyols

In certain embodiments, compositions of the present invention comprise substantially alternating polycarbonates. In some embodiments, such substantially alternating polycarbonates are both biobased and fossil-carbon sequestering.

In certain embodiments, polymer compositions of the present invention comprise substantially alternating aliphatic polycarbonate polymers containing a high percentage of carbonate linkages and a low content of ether linkages. In some embodiments, the percentage of carbonate linkages may be determined by $^1$H or $^{13}$C NMR spectroscopy. In some embodiments, the percentage of carbonate linkages may be determined by infra red (IR) or Raman spectroscopy.

In certain embodiments, aliphatic polycarbonate compositions of the present invention are characterized in that, on average in the composition, the percentage of carbonate linkages is 85% or greater. In certain embodiments, aliphatic polycarbonate compositions of the present invention are characterized in that, on average in the composition, the percentage of carbonate linkages is 90% or greater. In certain embodiments, aliphatic polycarbonate compositions of the present invention are characterized in that, on average in the composition, the percentage of carbonate linkages is 91% or greater. In certain embodiments, aliphatic polycarbonate compositions of the present invention are characterized in that, on average in the composition, the percentage of carbonate linkages is 92% or greater. In certain embodiments, aliphatic polycarbonate compositions of the present invention are characterized in that, on average in the composition, the percentage of carbonate linkages is 93% or greater. In certain embodiments, aliphatic polycarbonate compositions of the present invention are characterized in that, on average in the composition, the percentage of carbonate linkages is 94% or greater. In certain embodiments, aliphatic polycarbonate compositions of the present invention are characterized in that, on average in the composition, the percentage of carbonate linkages is 95% or greater. In certain embodiments, aliphatic polycarbonate compositions of the present invention are characterized in that, on average in the composition, the percentage of carbonate linkages is 96% or greater. In certain embodiments, aliphatic polycarbonate compositions of the present invention are characterized in that, on average in the composition, the percentage of carbonate linkages is 97% or greater. In certain embodiments, aliphatic polycarbonate compositions of the present invention are characterized in that, on average in the composition, the percentage of carbonate linkages is 98% or greater. In certain embodiments, aliphatic polycarbonate compositions of the present invention are characterized in that, on average in the composition, the percentage of carbonate linkages is 99% or greater. In certain embodiments, aliphatic polycarbonate compositions of the present invention are characterized in that, on average in the composition, the percentage of carbonate linkages is 99.5% or greater. In certain embodiments, the percentages above exclude ether linkages present in polymerization initiators or chain transfer agents and refer only to the linkages formed during epoxide $CO_2$ copolymerization.

In certain embodiments, aliphatic polycarbonate compositions of the present invention are characterized in that they contain essentially no ether linkages either within the polymer chains derived from epoxide $CO_2$ copolymerization or within any polymerization initiators, chain transfer agents or end groups that may be present in the polymer. In certain embodiments, aliphatic polycarbonate compositions of the present invention are characterized in that they contain, on average, less than one ether linkage per polymer chain within the composition. In certain embodiments, aliphatic polycarbonate compositions of the present invention are characterized in that they contain essentially no ether linkages.

In some embodiments, compositions of the present invention comprise aliphatic polycarbonate polyols having a structure P1:

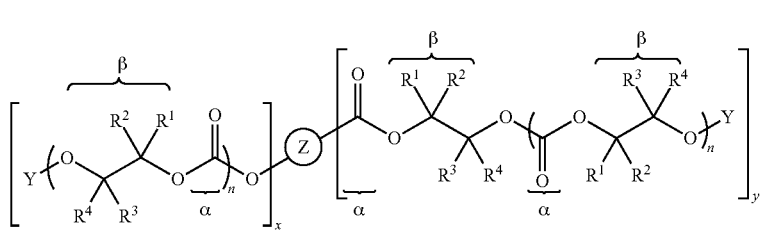

wherein, $R^1$, $R^2$, $R^3$, $R^4$, α, and β are described above and herein:

Y is, at each occurrence, independently —H, a reactive group (as described above and herein), or a site of attachment to any of the chain-extending moieties or isocyanates described in the classes and subclasses herein;

n is at each occurrence, independently an integer from about 2 to about 50:

is a covalent bond or a multivalent moiety; and x and y are each independently an integer from 0 to 6, where the sum of x and y is between 2 and 6.

In certain embodiments, the multivalent moiety

embedded within the aliphatic polycarbonate chain is derived from a polyfunctional chain transfer agent having two or more sites from which epoxide/$CO_2$ copolymerization can occur. In certain embodiments, such copolymerizations are performed in the presence of polyfunctional chain transfer agents as exemplified in PCT Publication No. WO 2010/028362. In certain embodiments, such copolymerizations are performed as exemplified in U.S. Patent Publication No. U.S. 2011/0245424. In certain embodiments, such copolymerizations are performed as exemplified in Cyriac et al. *Green Chem.* 2011 (13), 3469-3475.

In some embodiments, n is, at each occurrence independently an integer from about 2 to about 50. In some embodiments, n is, at each occurrence independently an integer from about 10 to about 50. In some embodiments, n is, at each occurrence independently an integer from about 20 to about 50. In some embodiments, n is, at each occurrence independently an integer from about 30 to about 50. In some embodiments, n is, at each occurrence independently an integer from about 40 to about 50. In some embodiments, n is, at each occurrence independently an integer from about 2 to about 25. In some embodiments, n is, at each occurrence independently an integer from about 2 to about 10.

In certain embodiments, a polyfunctional chain transfer agent has a formula:

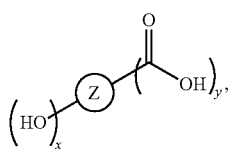

wherein each of

, x, and y is as described above and herein. In certain embodiments, such polyfunctional chain transfer agents are biobased.

In certain embodiments, aliphatic polycarbonate chains in polymer compositions of the present invention comprise chains with a structure P2:

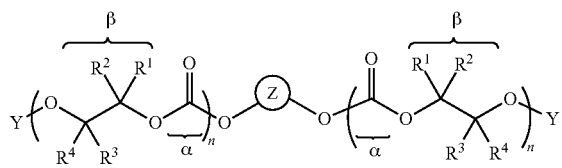

P2 wherein each of $R^1$, $R^2$, $R^3$, $R^4$, Y,

n, α, and β is as described above and herein.

In certain embodiments where aliphatic polycarbonate chains have a structure P2,

is derived from a dihydric alcohol. In such instances

represents the carbon-containing backbone of the dihydric alcohol, while the two oxygen atoms adjacent to

are derived from the —OH groups of the diol. For example, if the polyfunctional chain transfer agent were ethylene glycol, then

would be —$CH_2CH_2$— and P2 would have the following structure:

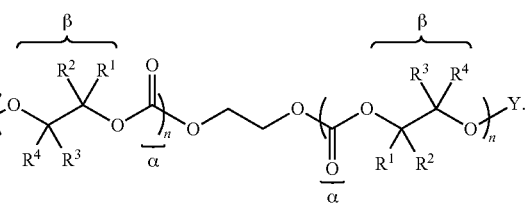

In certain embodiments where

is derived from a dihydric alcohol, the dihydric alcohol comprises a $C_{2-40}$ diol. In certain embodiments, the dihydric alcohol is selected from the group consisting of: 1,2-ethanediol, 1,2-propanediol, 1,3-propanediol, 1,2-butanediol, 1,3-butanediol, 1,4-butanediol, 1,5-pentanediol, 2,2-dimethylpropane-1,3-diol, 2-butyl-2-ethylpropane-1,3-diol, 2-methyl-2,4-pentane diol, 2-ethyl-1,3-hexane diol, 2-methyl-1,3-propane diol, 1,5-hexanediol, 1,6-hexanediol, 1,8-octanediol, 1,10-decanediol, 1,12-dodecanediol, 2,2,4,4-tetramethylcyclobutane-1,3-diol, 1,3-cyclopentanediol, 1,2-cyclohexanediol, 1,3-cyclohexanediol, 1,4-cyclohexanediol, 1,2-cyclohexanedimethanol, 1,3-cyclohexanedimethanol, 1,4-cyclohexanedimethanol, 1,4-cyclohexanediethanol, isosorbide, glycerol monoesters, glycerol monoethers, trimethylolpropane monoesters, trimethylolpropane monoethers, pentaerythritol diesters, pentaerythritol diethers, and alkoxylated derivatives of any of these. In certain embodiments, any of the above dihydric alcohols are characterized in that they are derived from biomass.

In certain embodiments where

is derived from a dihydric alcohol, the dihydric alcohol is selected from the group consisting of: diethylene glycol, triethylene glycol, tetraethylene glycol, higher poly(ethylene glycol), such as those having number average molecular weights of from 220 to about 2000 g/mol, dipropylene glycol, tripropylene glycol, and higher poly(propylene glycol) such as those having number average molecular weights of from 234 to about 2000 g/mol. In certain embodiments, any of the above dihydric alcohols are characterized in that they are derived from biomass.

In certain embodiments where

is derived from a dihydric alcohol, the dihydric alcohol comprises an alkoxylated derivative of a molecule selected from the group consisting of: a diacid, a diol, or a hydroxy acid. In certain embodiments, the alkoxylated derivatives comprise ethoxylated or propoxylated molecules.

In certain embodiments where

is derived from a dihydric alcohol, the dihydric alcohol comprises a polymeric diol. In certain embodiments, a polymeric diol is selected from the group consisting of polyethers, polyesters, hydroxy-terminated polyolefins, polyether-copolyesters, polyether polycarbonates, polycarbonate-copolyesters, polyoxymethylene polymers, and alkoxylated analogs of any of these. In certain embodiments, the polymeric diol has an average molecular weight less than about 2000 g/mol. In certain embodiments, any of the above dihydric alcohols are characterized in that they are derived from biomass.

In certain embodiments,

is derived from a polyhydric alcohol with more than two hydroxy groups. In embodiments in which

is derived from a polyhydric alcohol with more than two hydroxyl groups, these >2 functional polyhydric alcohols are a component of a mixture containing predominantly polyhydric alcohols with two hydroxyl groups. In certain embodiments, these >2 functional polyhydric alcohols are less than 20% of the total polyhydric alcohols mixture by weight. In certain embodiments, these >2 functional polyhydric alcohols are less than 10% of the total polyhydric alcohols mixture. In certain embodiments, these >2 functional polyhydric alcohols are less than 5% of the total polyhydric alcohols mixture. In certain embodiments, these >2 functional polyhydric alcohols are less than 2% of the total polyhydric alcohols mixture.

In certain embodiments, the aliphatic polycarbonate chains in polymer compositions of the present invention comprise aliphatic polycarbonate chains where the moiety

is derived from a triol. In certain embodiments, such aliphatic polycarbonate chains have the structure P3:

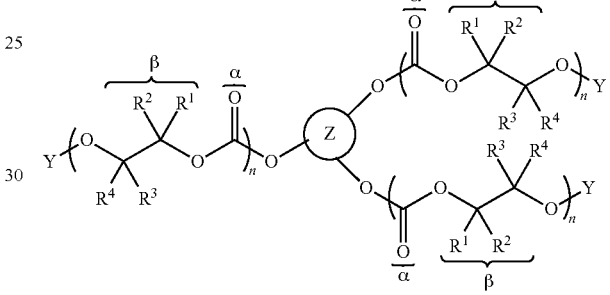

P3 wherein each of $R^1$, $R^2$, $R^3$, $R^4$, Y,

n, α, and β is as described above and herein.

In certain embodiments where

is derived from a triol, the triol is selected from the group consisting of: glycerol, 1,2,4-butanetriol, 2-(hydroxymethyl)-1,3-propanediol; hexane triols, trimethylol propane, trimethylol ethane, trimethylolhexane, 1,2,4-cyclohexanetrimethanol, pentaerythritol mono esters, pentaerythritol mono ethers, and alkoxylated analogs of any of these. In certain embodiments, such alkoxylated derivatives comprise ethoxylated or propoxylated molecules. In certain embodiments, any of the above triols are characterized in that they are derived from biomass.

In certain embodiments,

is derived from an alkoxylated derivative of a trifunctional carboxylic acid or trifunctional hydroxy acid. In certain embodiments, alkoxylated derivatives comprise ethoxylated or propoxylated molecules.

In certain embodiments, where

is derived from a polymeric triol, the polymeric triol is selected from the group consisting of polyethers, polyesters, hydroxy-terminated polyolefins, polyether-copolyesters, polyether polycarbonates, polyoxymethylene polymers, polycarbonate-copolyesters, and alkoxylated analogs of any of these. In certain embodiments, the alkoxylated polymeric triols comprise ethoxylated or propoxylated molecules. In certain embodiments, any of the above triols are characterized in that they are derived from biomass.

In certain embodiments,

is derived from a polyhydric alcohol with four hydroxy groups. In certain embodiments, aliphatic polycarbonate chains in polymer compositions of the present invention comprise aliphatic polycarbonate chains where the moiety

is derived from a tetraol. In certain embodiments, such tetraols are characterized in that they are derived from biomass. In certain embodiments, aliphatic polycarbonate chains in polymer compositions of the present invention comprise chains with the structure P4:

P4

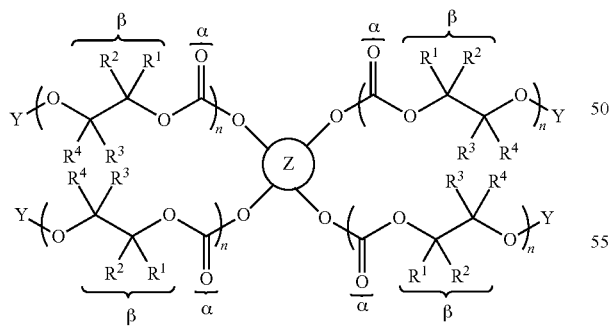

wherein each of $R^1$, $R^2$, $R^3$, $R^4$, Y,

n, α, and β is as described above and herein.

In certain embodiments,

is derived from a polyhydric alcohol with more than four hydroxy groups. In certain embodiments, such polyhydric alcohols are characterized in that they are derived from biomass. In certain embodiments,

is derived from a polyhydric alcohol with six hydroxy groups. In certain embodiments, a polyhydric alcohol is dipentaerythritol or an alkoxylated analog or other derivative thereof. In certain embodiments, a polyhydric alcohol is sorbitol or an alkoxylated analog thereof. In certain embodiments, aliphatic polycarbonate chains in polymer compositions of the present invention comprise chains with the structure P5:

P5

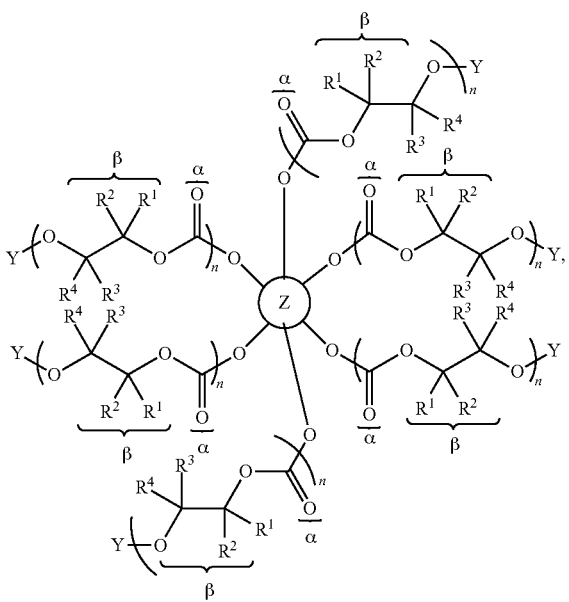

wherein each of $R^1$, $R^2$, $R^3$, $R^4$, Y,

n, α and β is as described above and herein.

In certain embodiments, aliphatic polycarbonates of the present invention comprise a combination of bifunctional chains (e.g., polycarbonates of formula P2) in combination with higher functional chains (e.g., one or more polycarbonates of formulae P3 to P5).

In certain embodiments,

is derived from a hydroxy acid. In certain embodiments, such hydroxy acids are characterized in that they are derived from biomass. In certain embodiments, aliphatic polycarbonate chains in polymer compositions of the present invention comprise chains with the structure P6:

P6

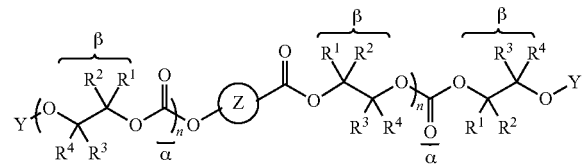

wherein each of $R^1$, $R^2$, $R^3$, $R^4$, Y,

, n, α, and β is as described above and herein. In such instances,

represents the carbon-containing backbone of the hydroxy acid, while ester and carbonate linkages adjacent to

are derived from the —$CO_2H$ group and the hydroxy group of the hydroxy acid. For example, if

were derived from 3-hydroxypropanoic acid, then

would be —$CH_2CH_2$— and P6 would have the following structure:

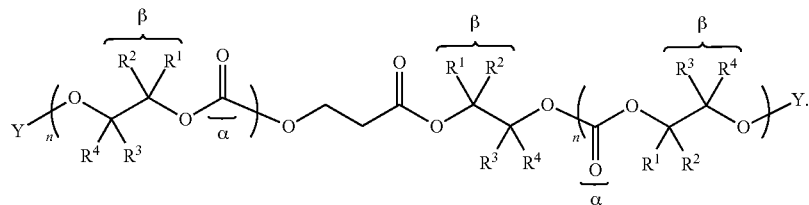

In certain embodiments,

is derived from an optionally substituted $C_{2-40}$ hydroxy acid. In certain embodiments,

is derived from a polyester. In certain embodiments, such polyesters have a molecular weight less than about 2000 g/mol.

In certain embodiments, a hydroxy acid is an alpha-hydroxy acid. In certain embodiments, a hydroxy acid is selected from the group consisting of: glycolic acid, DL-lactic acid, D-lactic acid. L-lactic, citric acid, and mandelic acid. In certain embodiments, any of the above hydroxy acids are characterized in that they are derived from biomass.

In certain embodiments, a hydroxy acid is a beta-hydroxy acid. In certain embodiments, a hydroxy acid is selected from the group consisting of: 3-hydroxypropionic acid, DL 3-hydroxybutryic acid, D-3 hydroxybutryic acid. L-3-hydroxybutyric acid. DL-3-hydroxy valeric acid, D-3-hydroxy valeric acid, L-3-hydroxy valeric acid, salicylic acid, and derivatives of salicylic acid. In certain embodiments, any of the above hydroxy acids are characterized in that they are derived from biomass.

In certain embodiments, a hydroxy acid is a α-ω hydroxy acid. In certain embodiments, a hydroxy acid is selected from the group consisting of: optionally substituted $C_{3-20}$ aliphatic α-ω hydroxy acids and oligomeric esters. In certain embodiments, any of the above hydroxy acids are characterized in that they are derived from biomass.

In certain embodiments, a hydroxy acid is selected from the group consisting of:

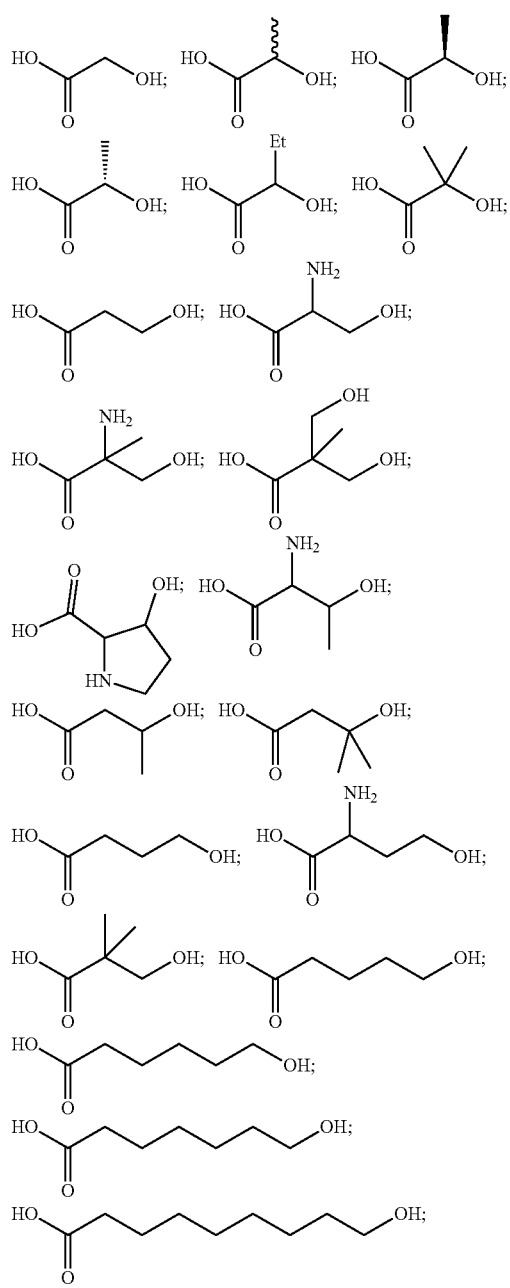
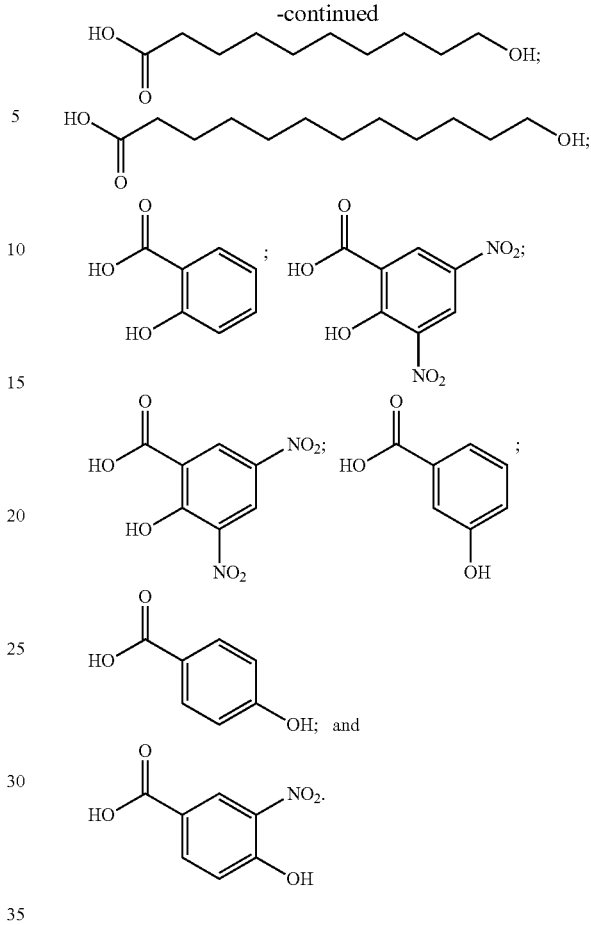

In certain embodiments, any of the above hydroxy acids are characterized in that they are derived from biomass.

In certain embodiments, $$\text{(Z)}$$

is derived from a polycarboxylic acid. In certain embodiments, such polycarboxylic acids are characterized in that they are derived from biomass. In certain embodiments, aliphatic polycarbonate chains in polymer compositions of the present invention comprise chains with the structure P7:

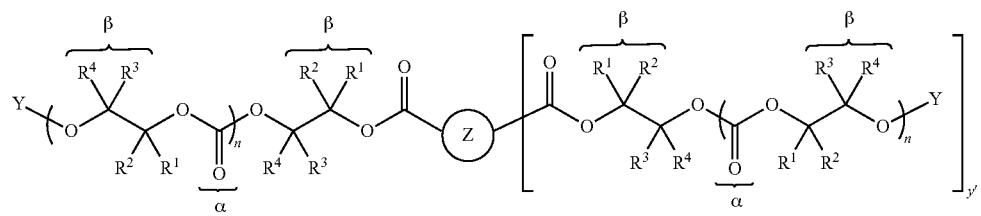

P7 wherein each of $R^1$, $R^2$, $R^3$, $R^4$, Y, (Z)

n, α, and β is as described above and herein, and y' is an integer from 1 to 5 inclusive.

In embodiments where the aliphatic polycarbonate chains have a structure P7, (Z)

represents the carbon-containing backbone (or a bond in the case of oxalic acid) of a polycarboxylic acid, while ester groups adjacent to (Z)

are derived from —$CO_2H$ groups of the polycarboxylic acid. For example, if (Z)

were derived from succinic acid ($HO_2CCH_2CH_2CO_2H$), then (Z)

would be —$CH_2CH_2$— and P7 would have the following structure:

$$\text{Y}\!\!-\!\!\left(\!\!-\!\!O\!-\!\!\underset{R^2\ R^1}{\overset{R^4\ R^3}{C}}\!\!-\!\!O\!-\!\!\underset{\alpha}{\underbrace{\overset{O}{\overset{\|}{C}}}}\!\!-\!\!\right)_{\!\!n}\!\!\overset{\beta}{\overbrace{O\!-\!\!\underset{R^4\ R^3}{\overset{R^2\ R^1}{C}}\!\!-\!\!O}}\!\!-\!\!\overset{O}{\overset{\|}{C}}\!\!-\!\!CH_2CH_2\!\!-\!\!\overset{O}{\overset{\|}{C}}\!\!-\!\!O\!\!\overset{\beta}{\overbrace{\underset{R^1\ R^2}{\overset{R^3\ R^4}{C}}}}\!\!-\!\!O\!\!-\!\!\left(\!\!\underset{\alpha}{\underbrace{\overset{O}{\overset{\|}{C}}}}\!\!-\!\!O\!-\!\!\overset{\beta}{\overbrace{\underset{R^3\ R^4}{\overset{R^1\ R^2}{C}}}}\!\!-\!\!O\!\!-\!\!\right)_{\!\!n}\!\!\!-\!\!\text{Y}$$

wherein each of $R^1$, $R^2$, $R^3$, $R^4$, Y, n, α, and β is as described above and herein.

In certain embodiments, (Z)

is derived from a dicarboxylic acid. In certain embodiments, aliphatic polycarbonate chains in polymer compositions of the present invention comprise chains with the structure P8:

P8

$$\text{Y}\!\!-\!\!\left(\!\!-\!\!O\!-\!\!\underset{R^2\ R^1}{\overset{R^4\ R^3}{C}}\!\!-\!\!O\!-\!\!\underset{\alpha}{\underbrace{\overset{O}{\overset{\|}{C}}}}\!\!-\!\!\right)_{\!\!n}\!\!\overset{\beta}{\overbrace{O\!-\!\!\underset{R^4\ R^3}{\overset{R^2\ R^1}{C}}\!\!-\!\!O}}\!\!-\!\!\overset{O}{\overset{\|}{C}}\!\!-\!\!(Z)\!\!-\!\!\overset{O}{\overset{\|}{C}}\!\!-\!\!O\!\!\overset{\beta}{\overbrace{\underset{R^3\ R^4}{\overset{R^1\ R^2}{C}}}}\!\!-\!\!O\!\!-\!\!\left(\!\!\underset{\alpha}{\underbrace{\overset{O}{\overset{\|}{C}}}}\!\!-\!\!O\!-\!\!\overset{\beta}{\overbrace{\underset{R^3\ R^4}{\overset{R^1\ R^2}{C}}}}\!\!-\!\!O\!\!-\!\!\right)_{\!\!n}\!\!\!-\!\!\text{Y}$$

wherein each of $R^1$, $R^2$, $R^3$, $R^4$, Y, (Z), n, α, and β is as described above and herein.

In certain embodiments, (Z)

is selected from the group consisting of: phthalic acid, isophthalic acid, terephthalic acid, maleic acid, succinic acid, malonic acid, glutaric acid, adipic acid, pimelic acid, suberic acid, and azelaic acid.

In certain embodiments, (Z)

is derived from a diacid selected from the group consisting of:

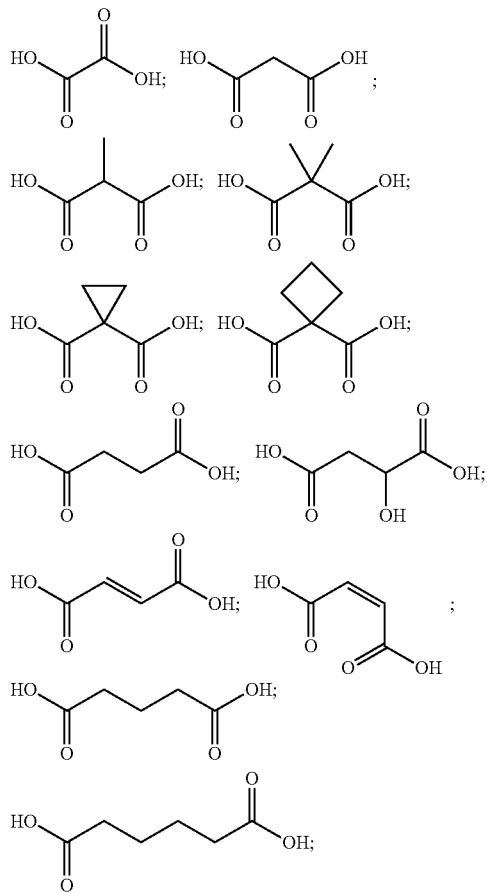

In certain embodiments, (Z)

is derived from a phosphorous-containing molecule. In certain embodiments, (Z)

has a formula —P(O)(OR)$_k$— where each R is independently an optionally substituted C$_{1-20}$ aliphatic group or an optionally substituted aryl group and k is 0, 1, or 2.

For example, if

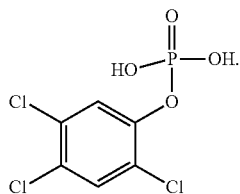

were derived from PhO—P(O)(OH)$_2$, then

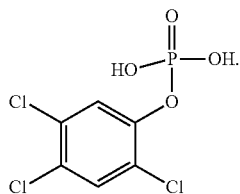

would be —P(O)OPh)- and P7 would have the following structure:

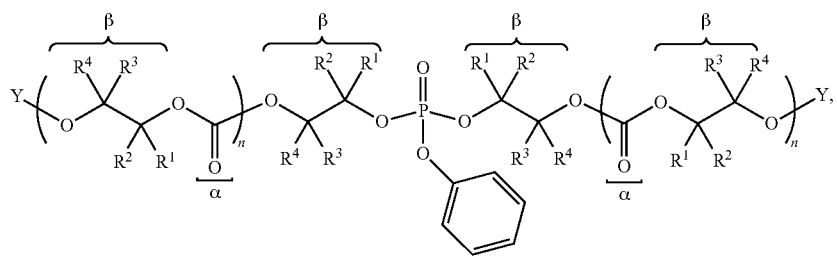

wherein each of R$^1$, R$^2$, R$^3$, R$^4$, Y, n, α, and β is as described above and herein.

In certain embodiments,

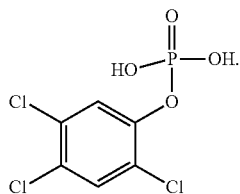

is derived from a phosphorous-containing molecule selected from the group consisting of:

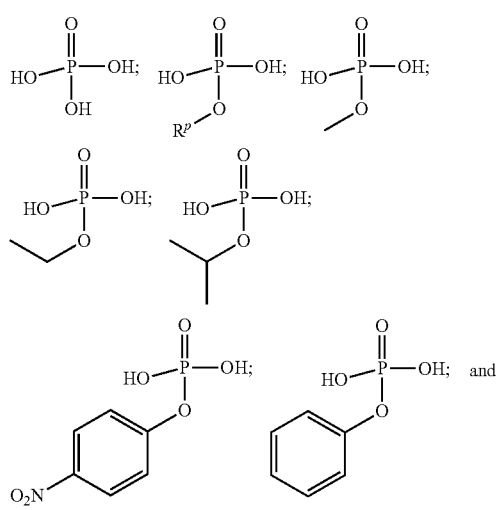

has a formula —P(O)(R$^p$)$_{p'}$— where R$^p$ is an optionally substituted C$_{1-20}$ aliphatic group or an optionally substituted aryl group and p' is 0, 1, or 2. In certain embodiments,

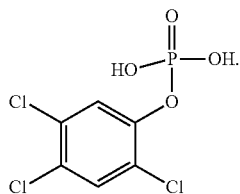

is derived from a phosphorous-containing molecule selected from the group consisting of:

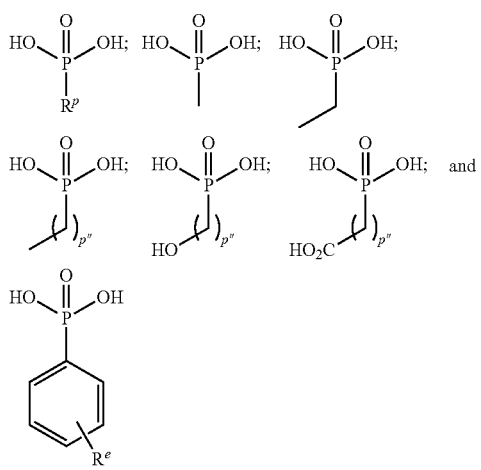

where R$^p$ is as described above and herein, and
R$^e$ is, at each occurrence, independently selected from the group consisting of: halogen, —NO$_2$, —CN, —SR$^f$, —S(O)R$^f$, —S(O)$_2$R$^f$, —NR$^f$C(O)R$^f$, —OC(O)R$^f$, —CO$_2$R$^f$, —NCO, —N$_3$, —OR$^f$, —OC(O)N(R$^f$)$_2$, —N(R$^f$)$_2$, —NR$^f$C(O)R$^f$, —NR$^f$C(O)OR$^f$; or an optionally substituted radical selected from the group consisting of C$_{1-20}$ aliphatic, C$_{1-20}$ heteroaliphatic, a 3- to 14-membered carbocycle, a 3- to 12-membered heterocycle, a 5- to 12-membered heteroaryl, and 6- to 10-membered aryl; where two or more adjacent R$^e$ groups can be taken together to form an optionally substituted saturated, partially unsaturated, or aromatic 5- to 12-membered ring containing 0 to 4 heteroatoms; where each occurrence of R$^f$ is independently —H, or an optionally substituted moiety selected from the group consisting of C$_{1-6}$ aliphatic, C$_{1-6}$ heteroaliphatic, 3- to 7-membered heterocyclic, 3- to 7-membered carbocyclic 6- to 10-membered aryl, and 5- to 10-membered heteroaryl; and p″ is an integer selected from 2-30.

In certain embodiments,

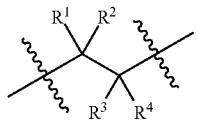

has a formula —PR— where R is an optionally substituted C$_{1-20}$ aliphatic group or an optionally substituted aryl group.

In certain embodiments, each

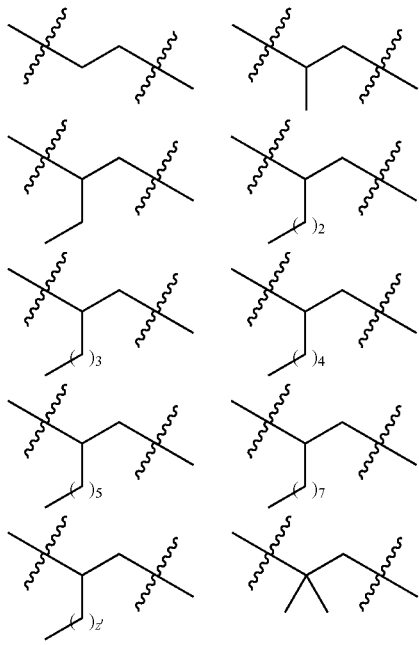

in the structures herein is independently selected from the group consisting of:

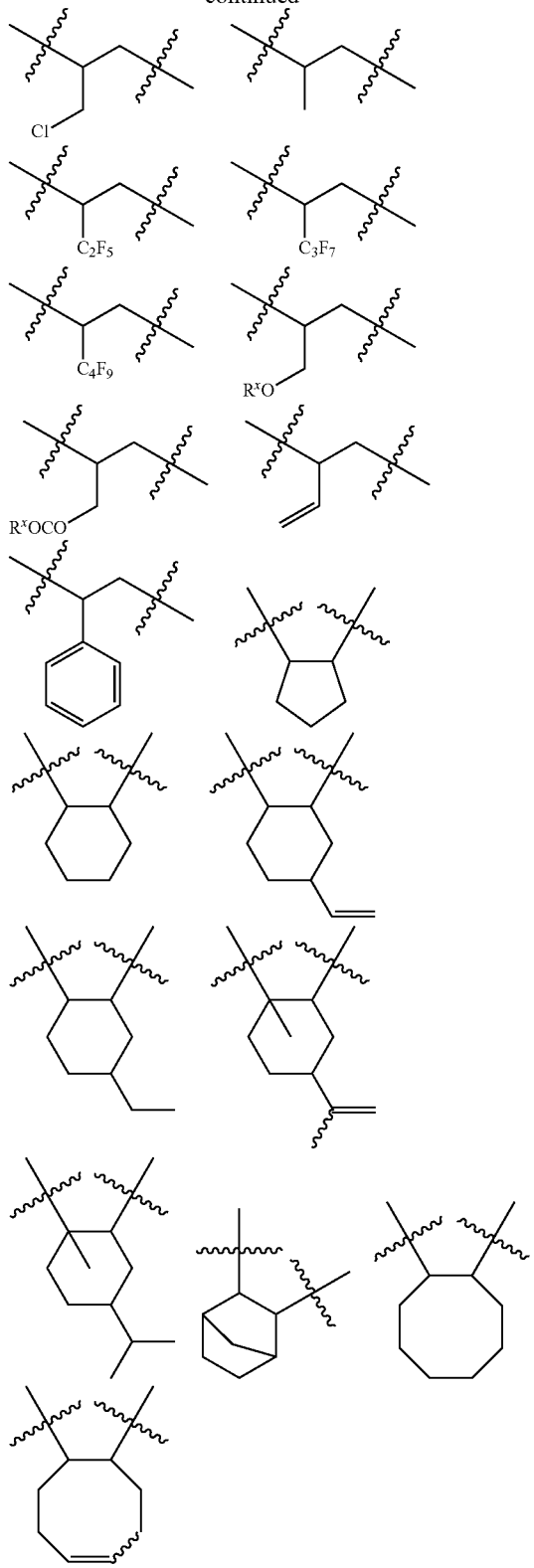

wherein each R$^x$ is independently an optionally substituted moiety selected from the group consisting of C$_{2-20}$ aliphatic, C$_{2-20}$ heteroaliphatic, 3- to 14-membered carbocyclic, 6- to 10-membered aryl, 5- to 10-membered heteroaryl, and 3- to 12-membered heterocyclic; and z′ is an integer selected from 9-30.

In certain embodiments, each

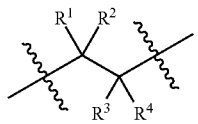

in the structures herein is independently selected from the group consisting of:

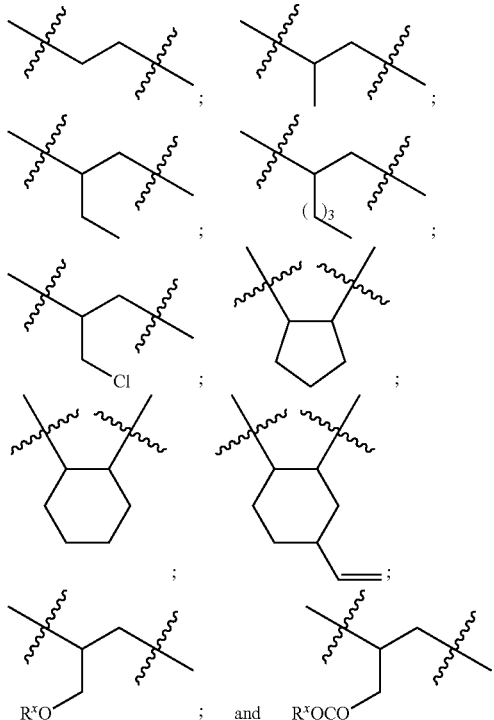

wherein $R^x$ is as described above and herein.

In certain embodiments, the moiety —Y in the structures herein is —H.

In certain embodiments, —Y comprises an ester linkage to an optionally substituted $C_{2-40}$ linker terminated with an —OH group. In certain embodiments, —Y is selected from the group consisting of:

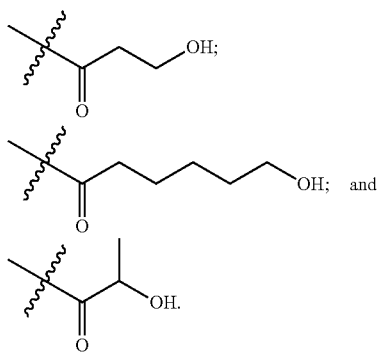

In certain embodiments, —Y comprises an ester linkage to an optionally substituted $C_{2-40}$ linker terminated with an —$CO_2H$ group. In certain embodiments, —Y is selected from the group consisting of:

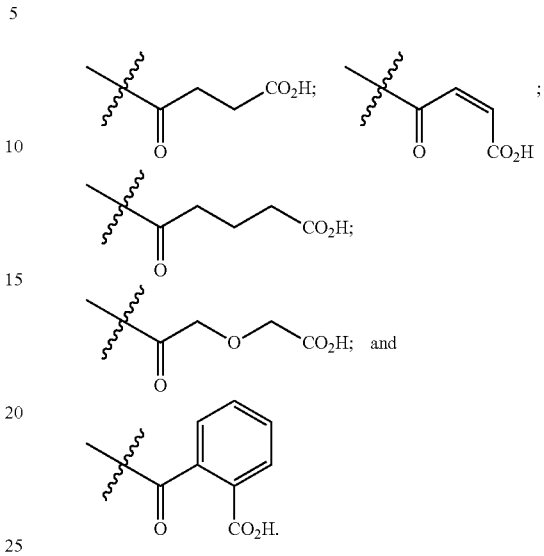

In certain embodiments, the moiety —Y in the structures herein comprises a hydroxy-terminated polymer. In certain embodiments, —Y comprises a hydroxy-terminated polyether. In certain embodiments, —Y comprises

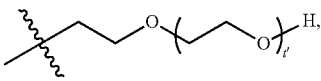

where t' is an integer from 1 to 20. In certain embodiments, —Y comprises

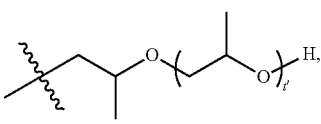

where t' is an integer from 1 to 20. In certain embodiments, —Y comprises

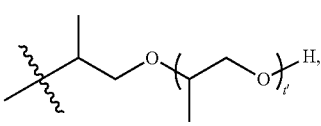

where t' is an integer from 1 to 20.

In certain embodiments, —Y comprises a hydroxy-terminated polyester. In certain embodiments, —Y is selected from the group consisting of:

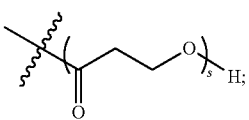

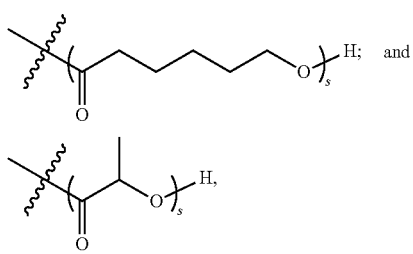

where s is an integer from 2 to 20.

In certain embodiments, aliphatic polycarbonate chains comprise:

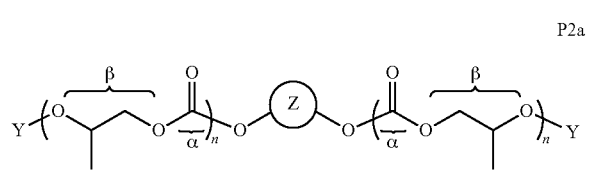

P2a wherein each of

—Y, n, α, and β is as described above and herein.

In certain embodiments, aliphatic polycarbonate chains comprise:

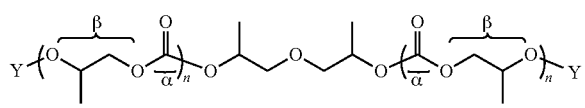

P2b wherein each of —Y n, α, and β is as described above and herein.

In certain embodiments, aliphatic polycarbonate chains comprise:

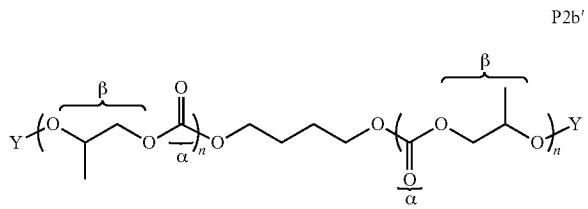

P2b' wherein each of —Y n, α, and β is as described above and herein.

In certain embodiments, aliphatic polycarbonate chains comprise:

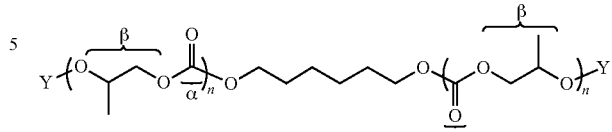

P2b'' wherein each of —Y n, α, and β is as described above and herein.

In certain embodiments, aliphatic polycarbonate chains comprise:

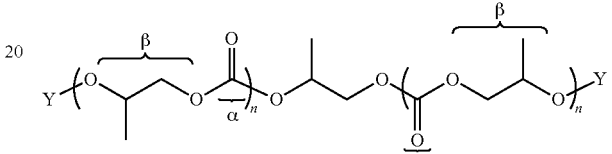

P2b''' wherein each of —Y n, α, and β is as described above and herein.

In certain embodiments, aliphatic polycarbonate chains comprise:

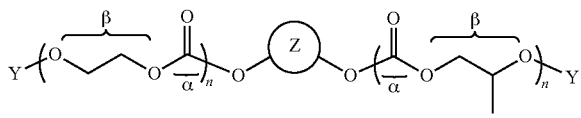

P2c wherein each of

—Y, n, α, and β is as described above and herein.

In certain embodiments, aliphatic polycarbonate chains comprise:

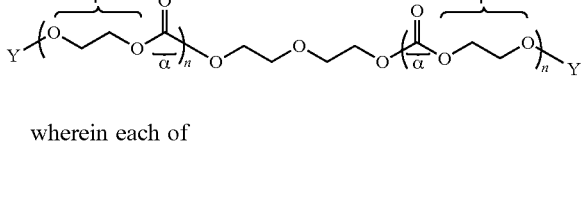

P2c' wherein each of

—Y, n, α, and β is as described above and herein.

In certain embodiments, aliphatic polycarbonate chains comprise:

P2c″

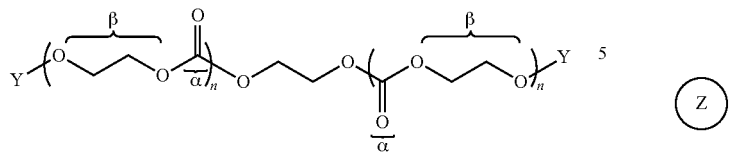

wherein each of (Z)

Y, n, α, and β is as described above and herein.

In certain embodiments, aliphatic polycarbonate chains comprise:

P2c‴

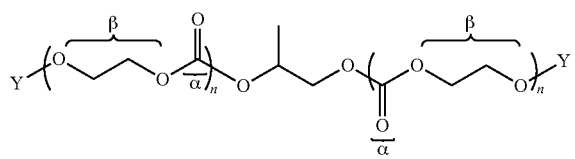

wherein each of (Z)

—Y, n, α, and β is as described above and herein.

In certain embodiments, aliphatic polycarbonate chains comprise:

P2d

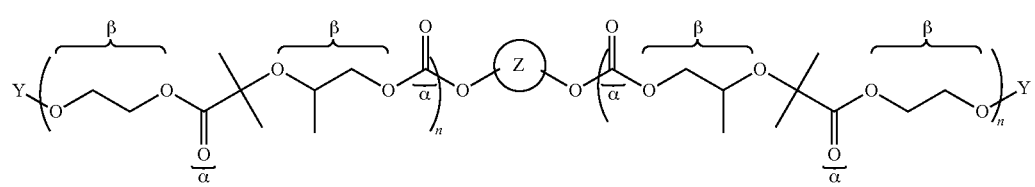

wherein each of —Y n, α, and β is as described above and herein.

In certain embodiments, aliphatic polycarbonate chains comprise:

P2f

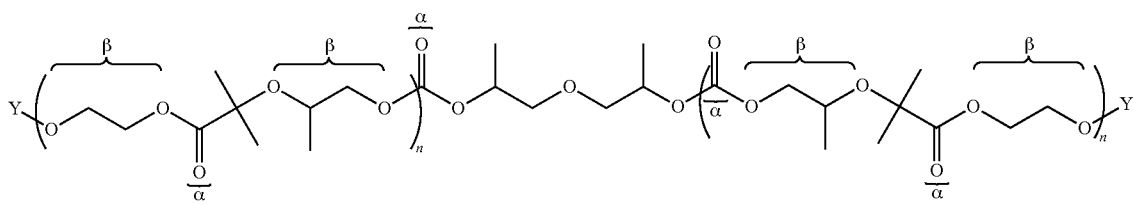

wherein each of (Z)

—Y, n, α, and β is as described above and herein.

In certain embodiments, aliphatic polycarbonate chains comprise:

P2g wherein each of —Y n, α, and β is as described above and herein.

In certain embodiments, aliphatic polycarbonate chains comprise:

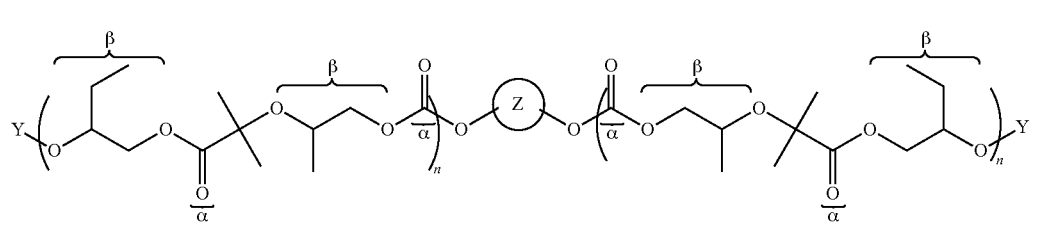

P2h wherein each of

—Y, n, α, and β is as described above and herein.

In certain embodiment, aliphatic polycarbonate chains comprise:

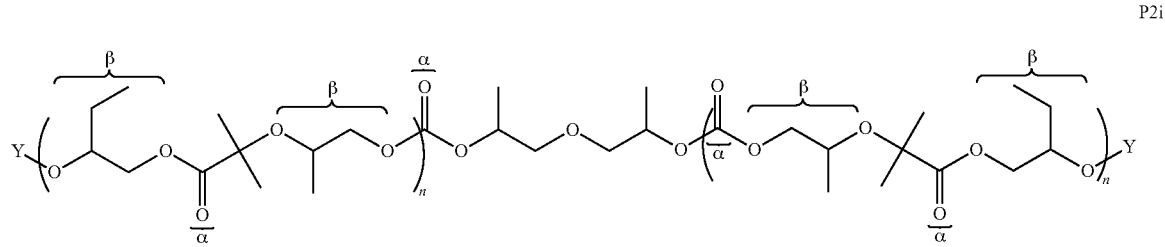

P2i wherein each of —Y n, α, and β is as described above and herein.

In certain embodiments, aliphatic polycarbonate chains comprise:

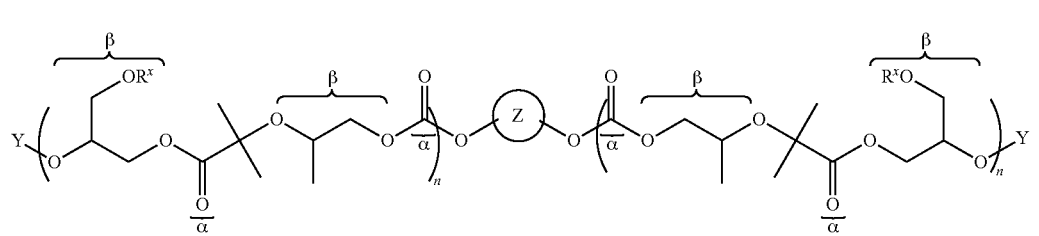

P2j wherein each of

—Y, $R^x$, n, α, and β is as described above and herein.

In certain embodiments, aliphatic polycarbonate chains comprise:

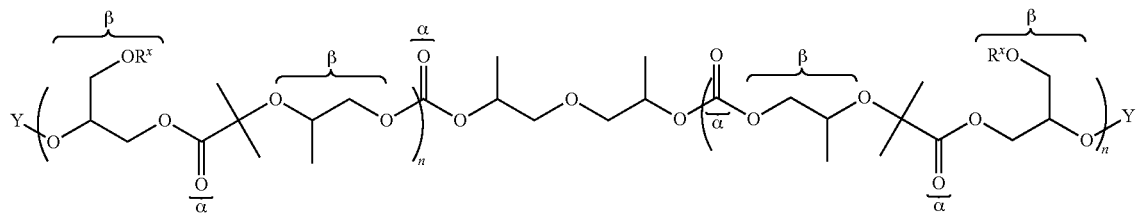

P2k wherein each of —Y, $R^x$, n, α, and β is as described above and herein.

In certain embodiments, aliphatic polycarbonate chains comprise:

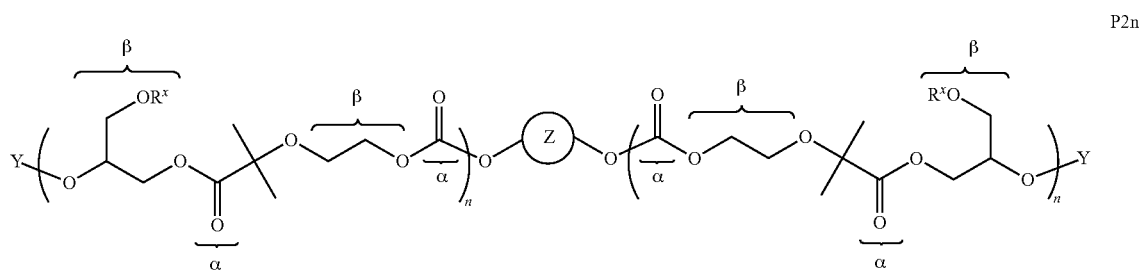

P2n wherein each of

$R^x$, —Y n, α, and β is as described above and herein.

In certain embodiments, aliphatic polycarbonate chains comprise:

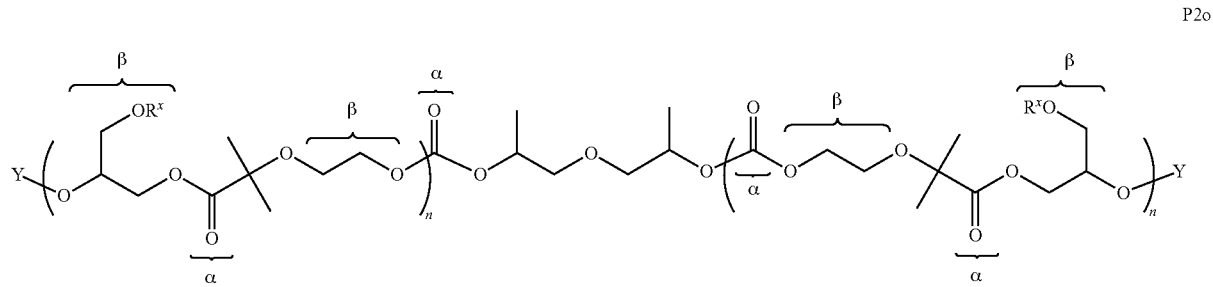

P2o wherein each of —Y, $R^x$, n, α, and β is as described above and herein.

In certain embodiments, aliphatic polycarbonate chains comprise:

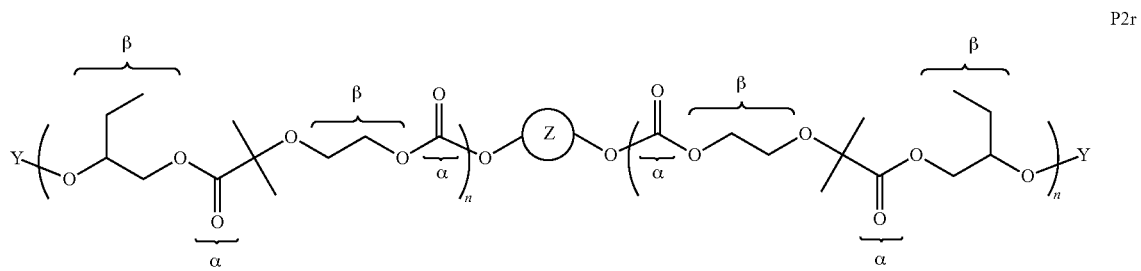

P2r wherein each of

—Y, n, α, and β is as described above and herein.

In certain embodiments, aliphatic polycarbonate chains comprise:

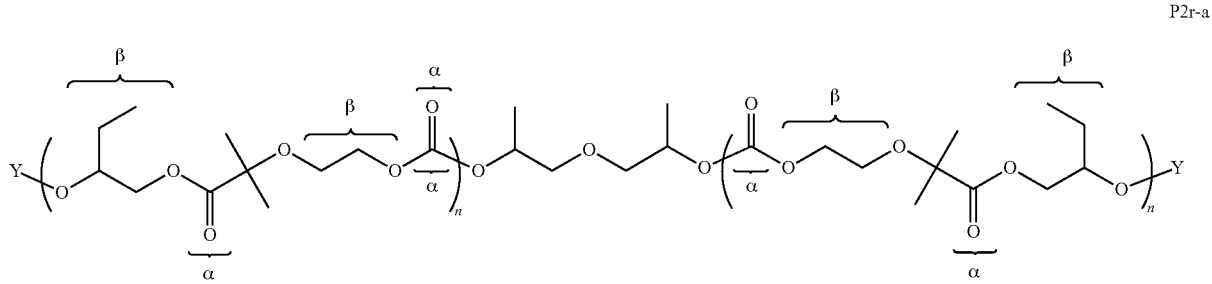

P2r-a wherein each of —Y n, α, and β is as described above and herein.

In certain embodiments, in polycarbonates of structures P2a, P2c, P2f, P2h, P2j, P2n, and P2r,

is selected from the group consisting of: ethylene glycol; diethylene glycol, triethylene glycol, 1,3 propane diol; 1,4 butane diol, hexylene glycol, 1,6 hexane diol, neopentyl glycol, propylene glycol, dipropylene glycol, tripropylene glycol, and alkoxylated derivatives of any of these. In certain embodiments, any of the above diols are characterized in that they are derived from biomass.

In certain embodiments, in polycarbonates of structures P2, P2a, P2b, P2b', P2b'', P2b''', P2c, P2c', P2c'', P2c''', P2d, P2f, P2g, P2h, P2i, P2j, P2k, P2n, P2o, P2r, and P2r-a, the embedded chain transfer agent is characterized in that it is derived from biomass. In certain embodiments, in polycarbonates of structures P2, P2a, P2b, P2b', P2b'', P2b''', P2c, P2c', P2c'', P2c''', P2d, P2f, P2g, P2h, P2i, P2j, P2k, P2n, P2o, P2r, and P2r-a, the embedded chain transfer agent is characterized in that it is not derived from biomass.

In certain embodiments, in polycarbonates of structures P2, P2a, P2b, P2b', P2b'', P2b''', P2c, P2c', P2c'', P2c''', P2d, P2f, P2g, P2h, P2i, P2j, P2k, P2n, P2o, P2r, and P2r-a, —Y is —H.

In certain embodiments, aliphatic polycarbonate chains comprise:

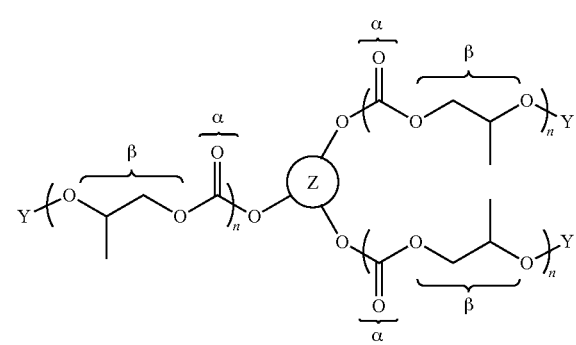

P3a wherein each of —Y n, α, and β is as described above and herein.

In certain embodiments, aliphatic polycarbonate chains comprise:

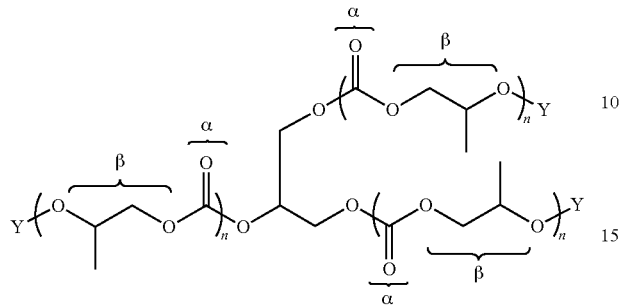

P3b wherein each of —Y n, α, and β is as described above and herein.

In certain embodiments, aliphatic polycarbonate chains comprise:

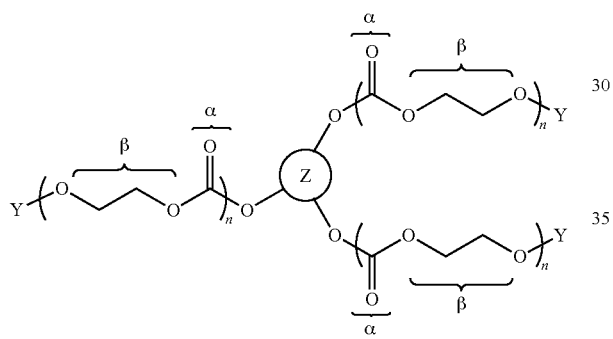

P3c wherein each of —Y n, α, and β is as described above and herein.

In certain embodiments, aliphatic polycarbonate chains comprise:

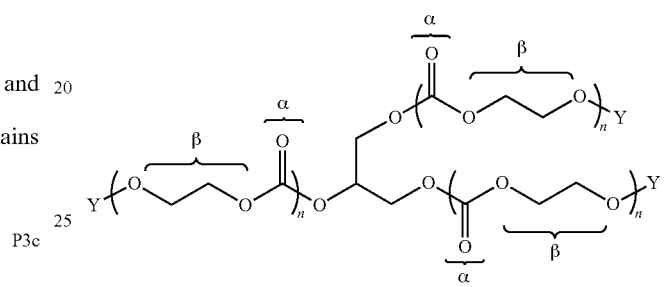

P3d wherein each of —Y n, α, and β is as described above and herein.

In certain embodiments, aliphatic polycarbonate chains comprise:

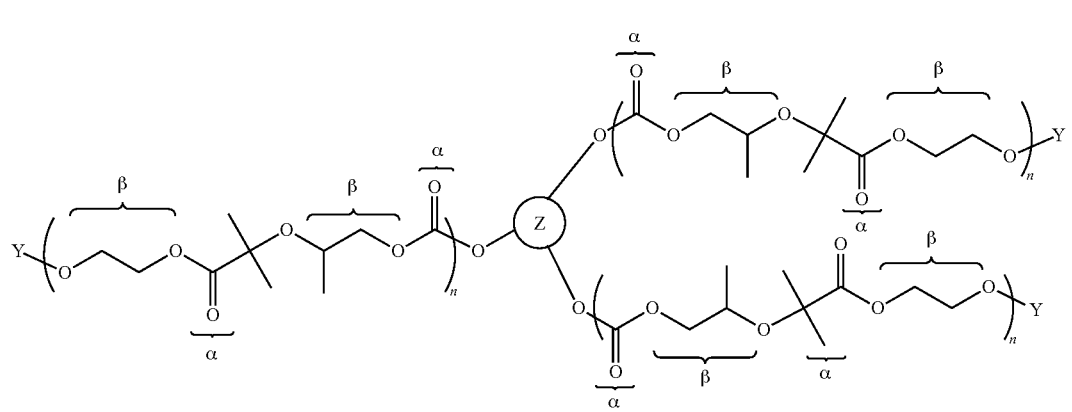

P3f wherein each of —Y n, α, and β is as described above and herein.

In certain embodiments, aliphatic polycarbonate chains comprise:
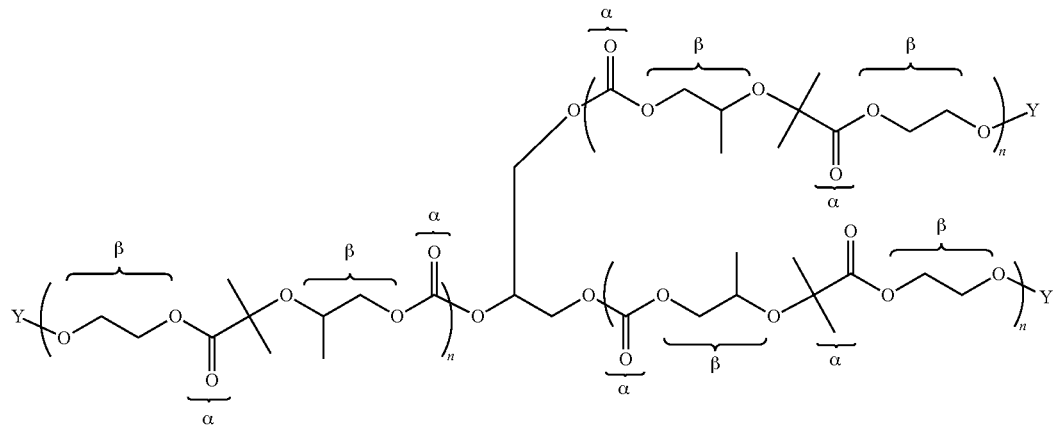
P3g
wherein each of —Y n, α, and β is as described above and herein.
In certain embodiments, aliphatic polycarbonate chains comprise:
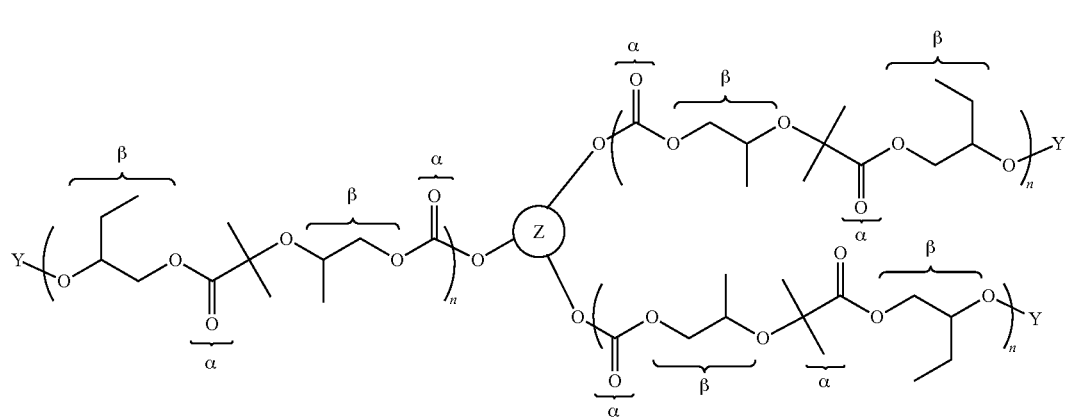
P3h
wherein each of —Y n, α, and β is as described above and herein.

In certain embodiments, aliphatic polycarbonate chains comprise:
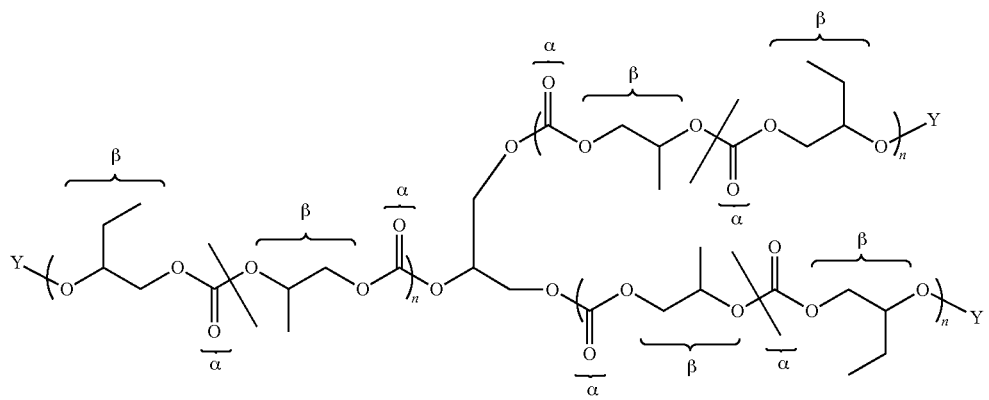
P3i
wherein each of —Y n, α, and β is as described above and herein.
In certain embodiments, aliphatic polycarbonate chains comprise:
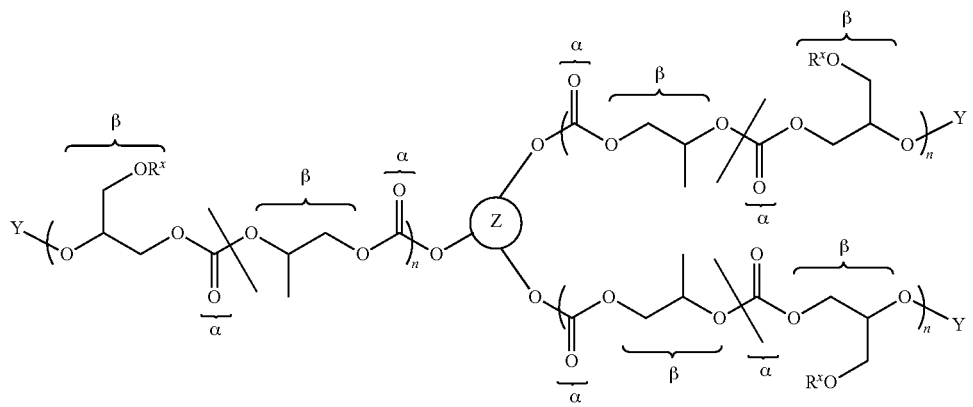
P3j
wherein each of —Y, $R^x$, n, α, and β is as described above and herein.
In certain embodiments, aliphatic polycarbonate chains comprise:
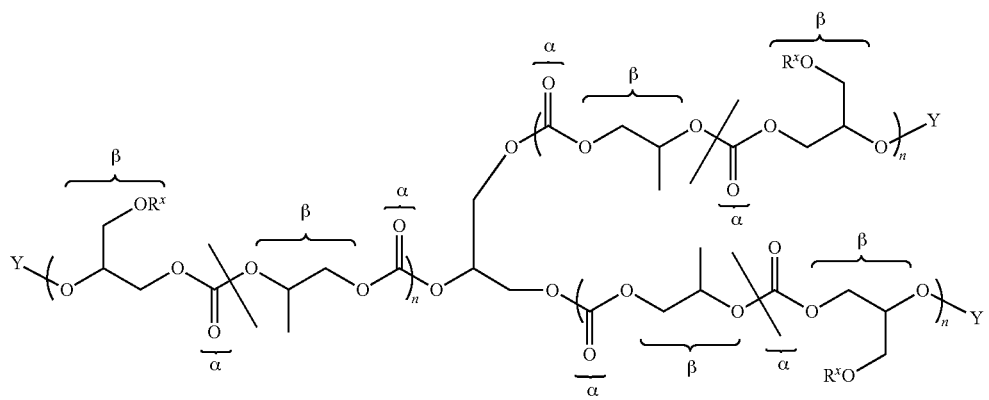
P3k wherein each of —Y, $R^x$, n, α, and β is as described above and herein.
In certain embodiments, aliphatic polycarbonate chains comprise:
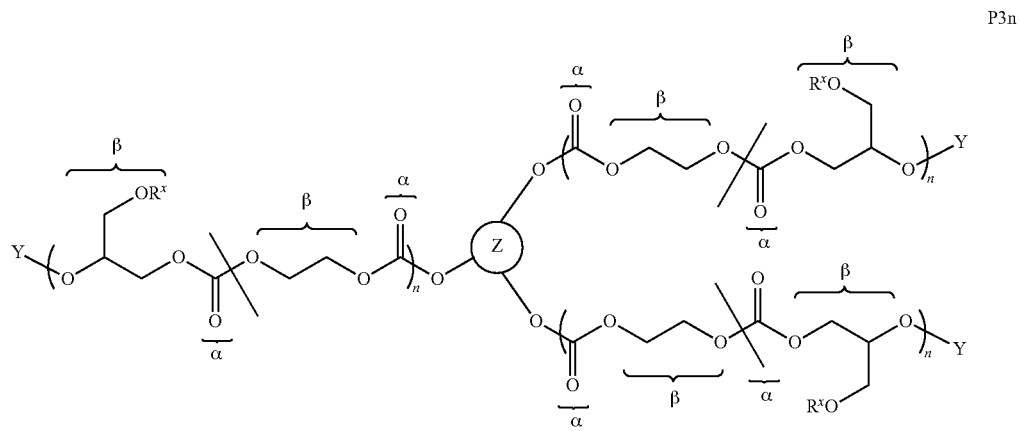
P3n
wherein each of —Y, $R^x$, n, α, and β is as described above and herein.
In certain embodiments, aliphatic polycarbonate chains comprise:
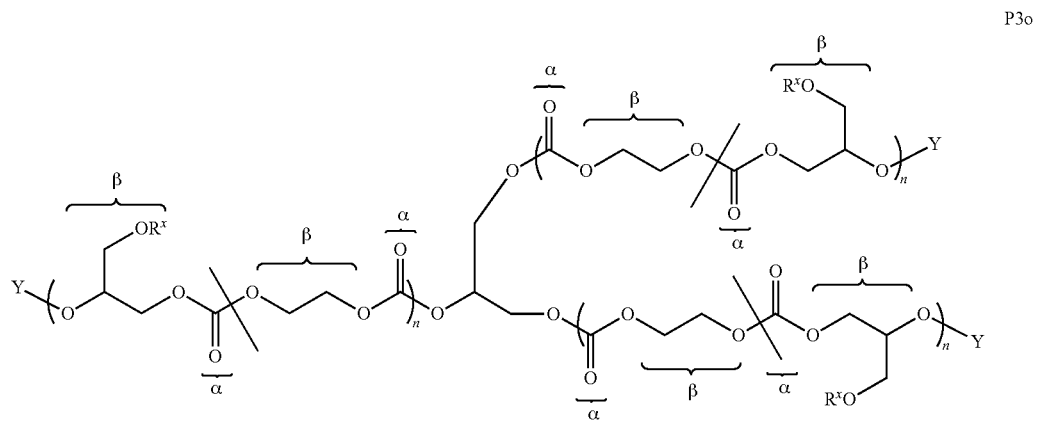
P3o
wherein each of —Y, $R^x$, n, α, and β is as described above and herein.

In certain embodiments, aliphatic polycarbonate chains comprise:

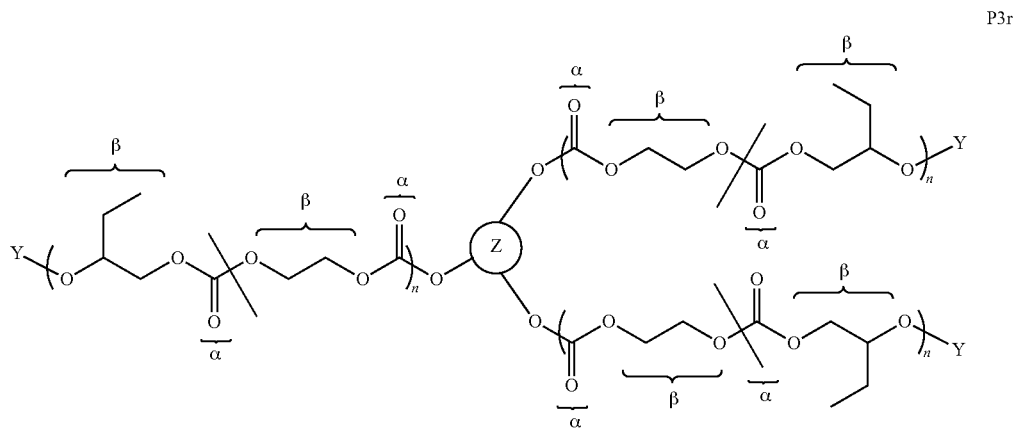

P3r wherein each of —Y n, α, and β is as described above and herein.

In certain embodiments, aliphatic polycarbonate chains comprise:

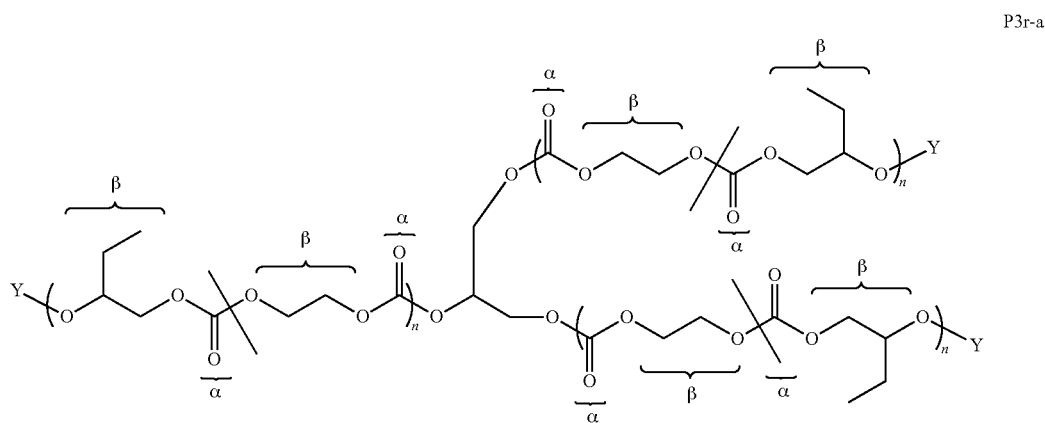

P3r-a wherein each of —Y n, α, and β is as described above and herein.

In certain embodiments, in polycarbonates of structures P3a, P3c, P3f, P3h, P3j, P3n, P3r, and P3r-a,

is selected from the group consisting of: glycerol, 1,2,4-butanetriol, 2-(hydroxymethyl)-1,3-propanediol; hexane triols, trimethylol propane, trimethylol ethane, trimethylolhexane, 1,2,4-cyclohexanetrimethanol, pentaerythritol mono esters, pentaerythritol mono ethers, and alkoxylated analogs of any of these. In certain embodiments, such alkoxylated derivatives comprise ethoxylated or propoxylated molecules. In certain embodiments, any of the above triols are characterized in that they are derived from biomass. In certain embodiments, in polycarbonates of structures P3, P3a, P3b, P3c, P3d. P3f, P3g, P3h, P3i, P3j, P3k, P3n, P3o, P3r, and P3r-a, the embedded chain transfer agent is characterized in that it is derived from biomass. In certain embodiments, in polycarbonates of structures P3, P3a, P3b, P3c, P3d, P3f, P3g, P3h, P3i, P3j, P3k, P3n, P3o, P3r, and P3r-a, the embedded chain transfer agent is characterized in that it is not derived from biomass.

In certain embodiments, in polycarbonates of structures P3, P3a, P3b, P3c, P3d, P3f, P3g, P3h, P3i, P3j, P3k P3n, P3o, P3r, and P3r-a, —Y is —H.

In certain embodiments, aliphatic polycarbonate chains comprise:

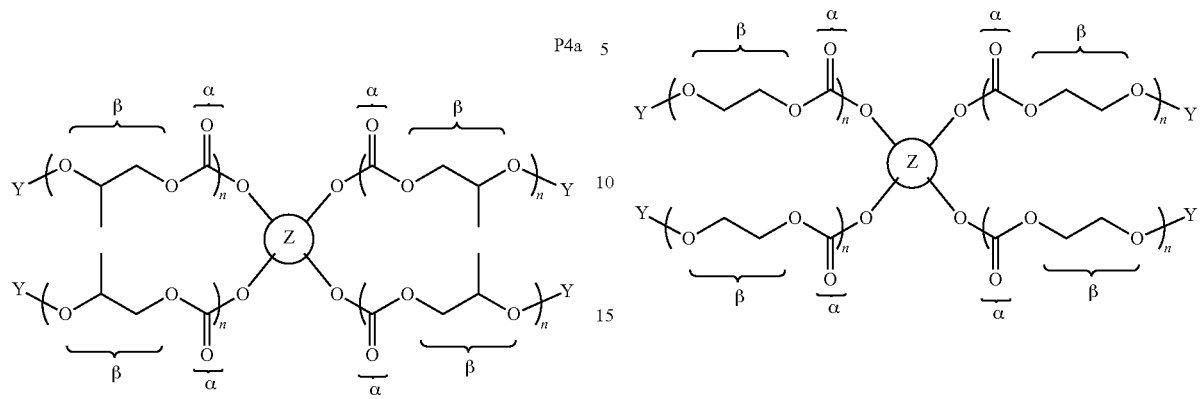

P4a wherein each of —Y n, α, and β is as described above and herein.

In certain embodiments, aliphatic polycarbonate chains comprise:

wherein each of —Y n, α, and β is as described above and herein.

In certain embodiments, aliphatic polycarbonate chains comprise:

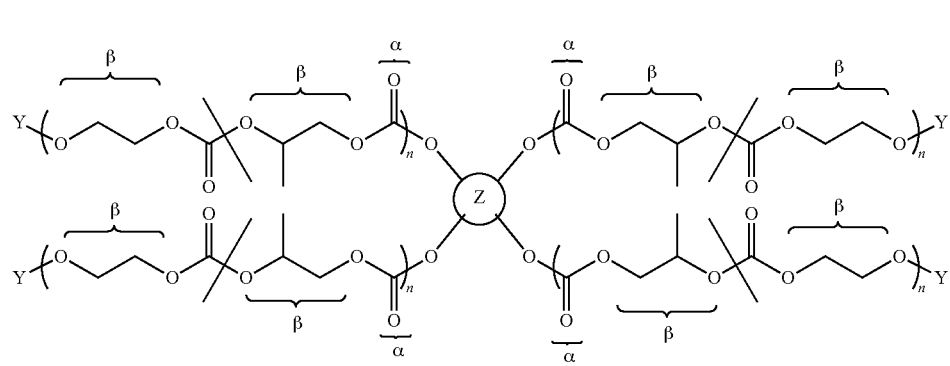

P4f wherein each of —Y n, α, and β is as described above and herein.

In certain embodiments, aliphatic polycarbonate chains comprise:

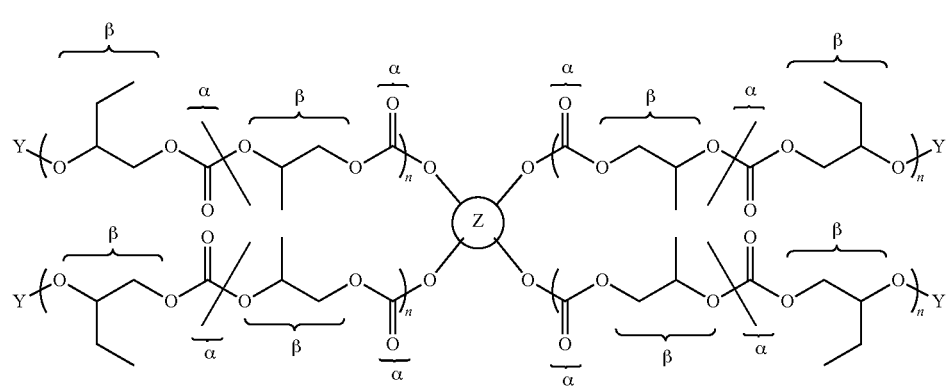

P4h wherein each of —Y n, α, and β is as described above and herein.

In certain embodiments, aliphatic polycarbonate chains comprise:

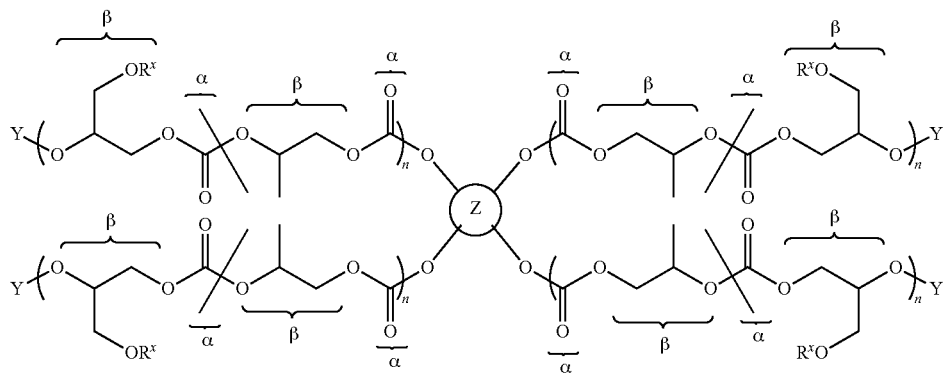

P4j wherein each of —Y, $R^x$, n, $\alpha$, and $\beta$ is as described above and herein.

In certain embodiments, aliphatic polycarbonate chains comprise:

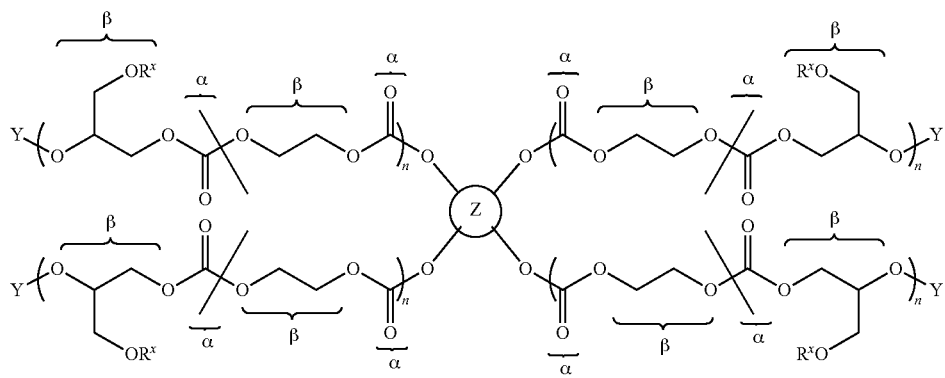

P4n wherein each of —Y, $R^x$, n, $\alpha$, and $\beta$ is as described above and herein.

In certain embodiments, aliphatic polycarbonate chains comprise:

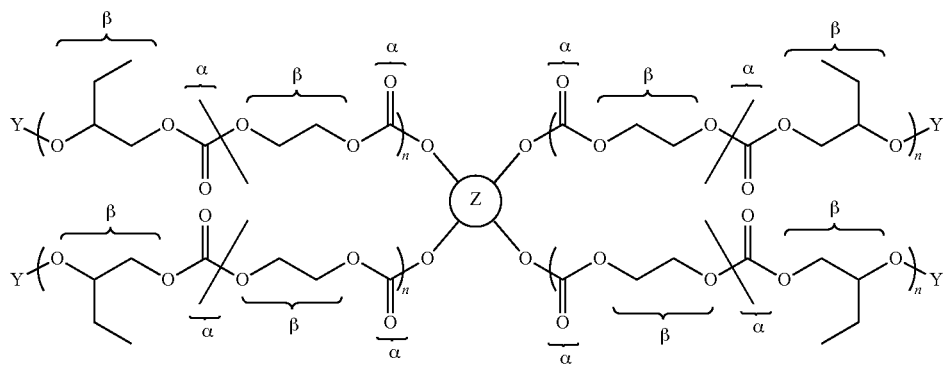

P4r wherein each of —Y n, $\alpha$, and $\beta$ is as described above and herein.

In certain embodiments, in polycarbonates of structures P4a, P4c, P4f, P4h, P4j, P4n, and P4r, the embedded chain transfer agent is characterized in that it is derived from biomass. In certain embodiments, in polycarbonates of structures P4a, P4c, P4f, P4h, P4j, P4n, and P4r, the embedded chain transfer agent is characterized in that it is not derived from biomass.

In certain embodiments, in polycarbonates of structures P4a, P4c, P4f, P4h, P4j, P4n, and P4r, —Y is —H.

In certain embodiments, aliphatic polycarbonate chains comprise:

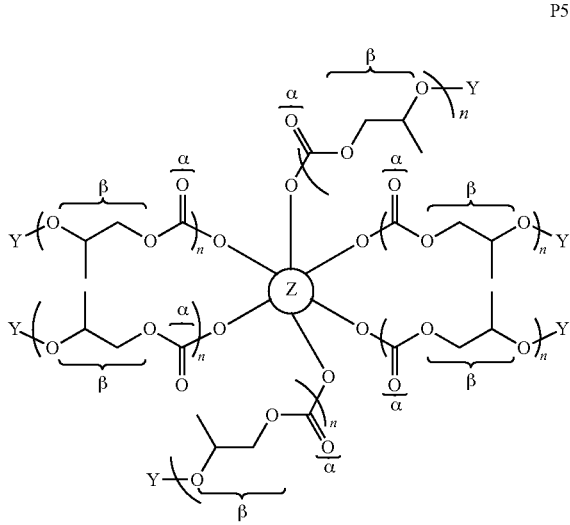

P5a

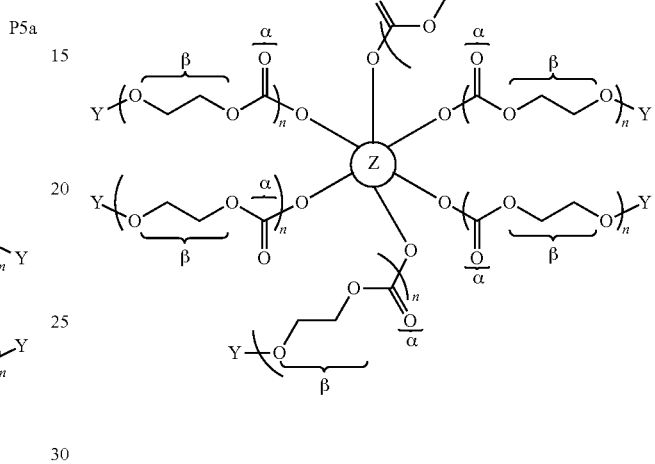

P5c wherein each of —Yn, α, and β is as described above and herein.

In certain embodiments, aliphatic polycarbonate chains comprise:

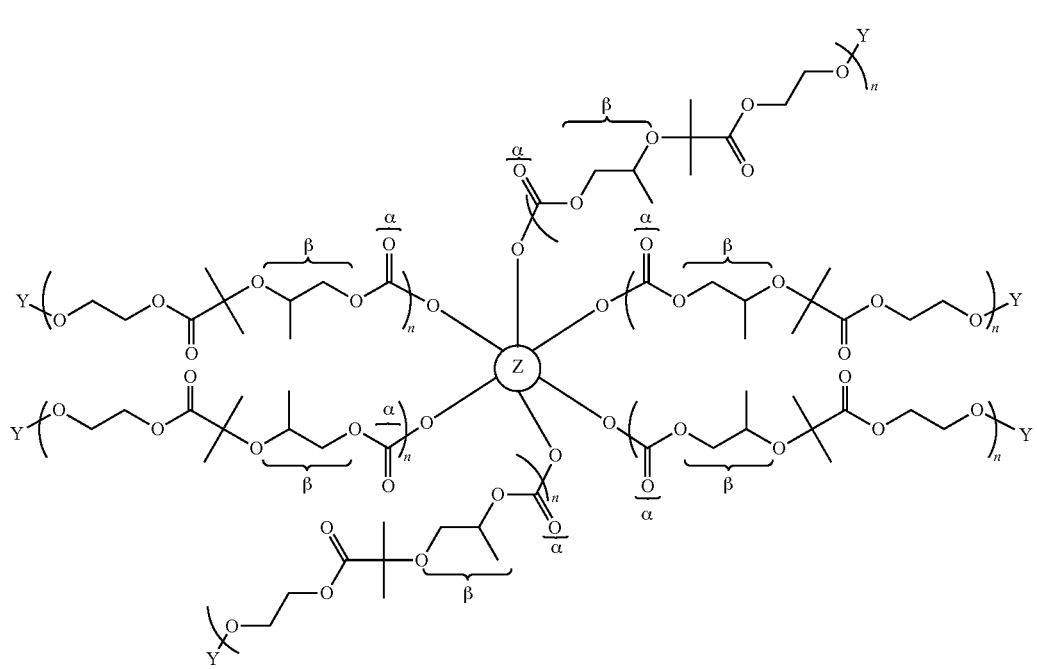

P5f wherein each of —Yn, α, and β is as described above and herein.

In certain embodiments, aliphatic polycarbonate chains comprise:
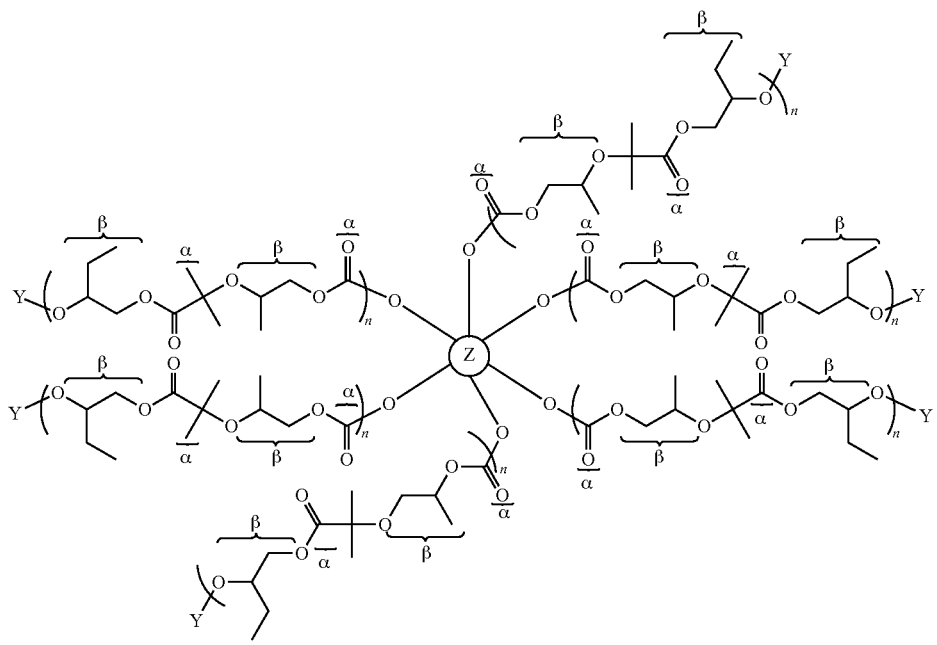
P5h
wherein each of —Y n, α, and β is as described above and herein.
In certain embodiments, aliphatic polycarbonate chains comprise:
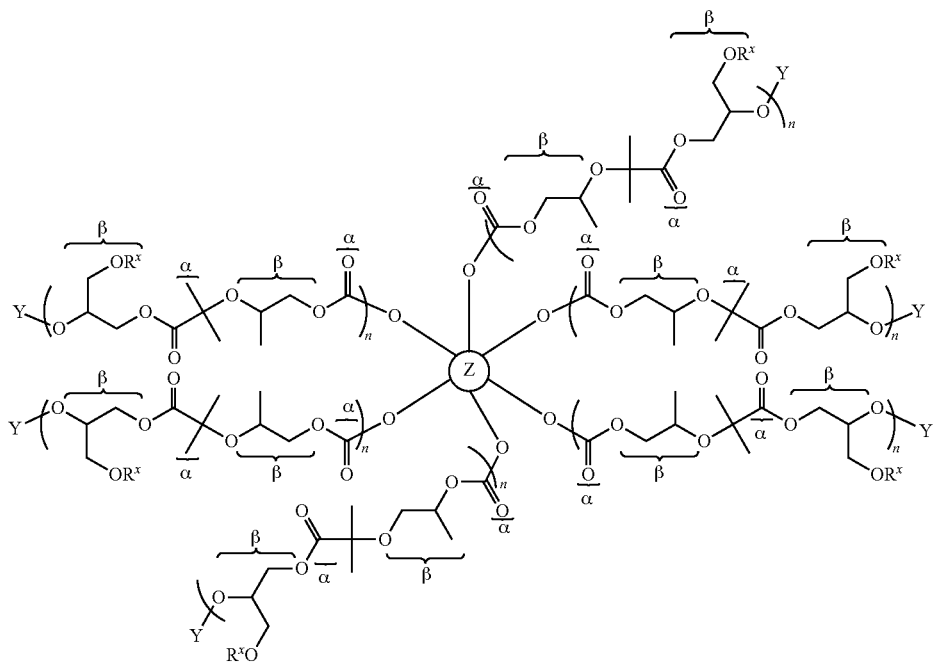
P5j
wherein each of —Y, $R^x$, n, α, and β is as described above and herein.

In certain embodiments, aliphatic polycarbonate chains comprise:
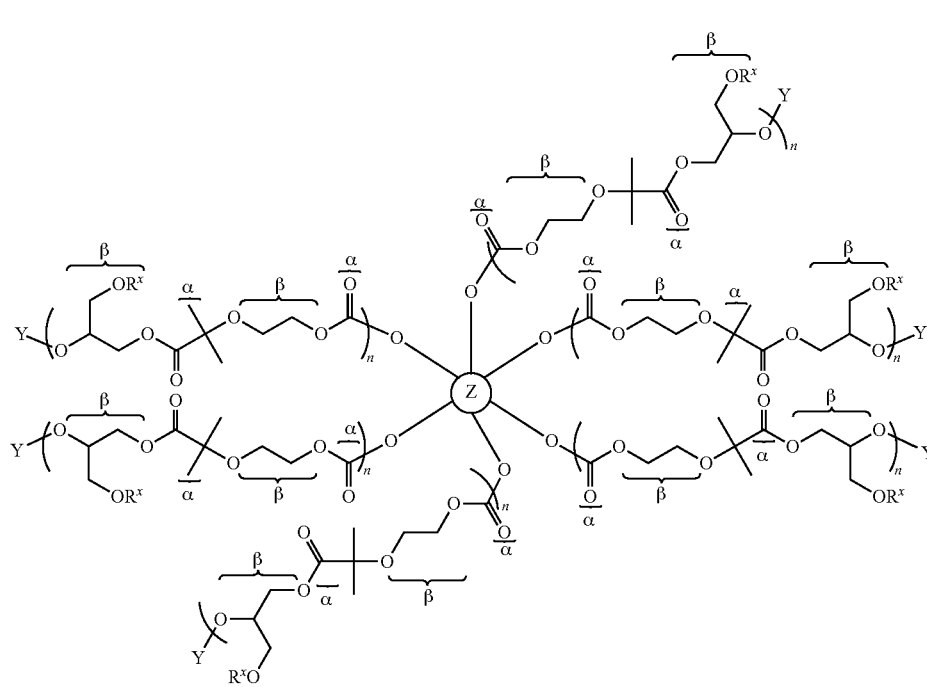
P5n
wherein each of —Y, $R^x$, n, $\alpha$, and $\beta$ is as described above and herein.
In certain embodiments, aliphatic polycarbonate chains comprise:
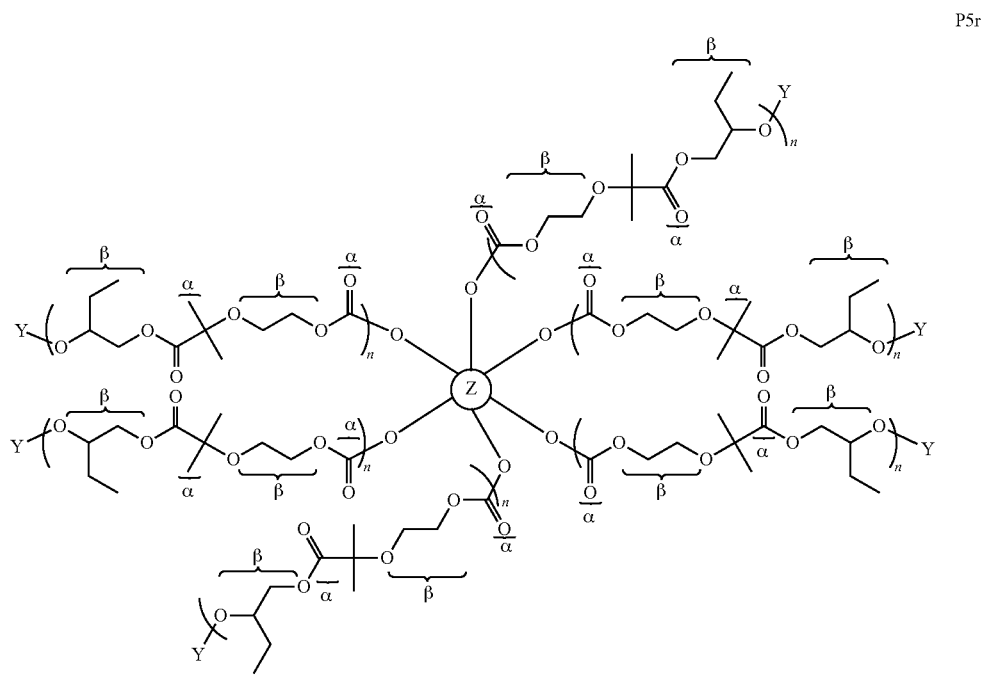
P5r
wherein each of —Y n, $\alpha$, and $\beta$ is as described above and herein.

In certain embodiments, in polycarbonates of structures P5a, P5c, P5f, P5h, P5j, P5n, and P5r,

is selected from the group consisting of: carbohydrates and their alkoxylated derivatives. In certain embodiments, any of the above triols are characterized in that they are derived from biomass.

In certain embodiments, in polycarbonates of structures P5a, P5c, P5f, P5h, P5j, P5n, and P5r, the embedded chain transfer agent is characterized in that it is derived from biomass. In certain embodiments, in polycarbonates of structures P5a, P5c, P5f, P5h, P5j, P5n, and P5r, the embedded chain transfer agent is characterized in that it is not derived from biomass.

In certain embodiments, in polycarbonates of structures P5a, P5c, P5f, P5h, P5j, P5n, and P5r, —Y is —H.

For polycarbonates comprising repeat units derived from two or more epoxides, such as those represented by structures P2f, P2g, P2h, P2i, P2j, P2k, P2n, P2o, P2r, P2r-a, P3f, P3g, P3h, P3i, P3j, P3k, P3n, P3o, P3r, P3r-a, P4f, P4h, P4j, P4n, P4r, P5f, P5h, P5j, P5n, and P5r, depicted above, it is to be understood that the structures drawn may represent mixtures of positional isomers or regioisomers that are not explicitly depicted. For example, the polymer repeat unit adjacent to either end group of the polycarbonate chains can be derived from either one of the two epoxides comprising the copolymers. Thus, while the polymers may be drawn with a particular repeat unit attached to an end group, the terminal repeat units might be derived from either of the two epoxides and a given polymer composition might comprise a mixture of all of the possibilities in varying ratios. The ratio of these end-groups can be influenced by several factors including the ratio of the different epoxides used in the polymerization, the structure of the catalyst used, the reaction conditions used (i.e., temperature pressure, etc.) as well as by the timing of addition of reaction components. Similarly, while the drawings above may show a defined regiochemistry for repeat units derived from substituted epoxides, the polymer compositions will, in some cases, contain mixtures of regioisomers. The regioselectivity of a given polymerization can be influenced by numerous factors including the structure of the catalyst used and the reaction conditions employed. To clarify, this means that the composition represented by structure P2r above, may contain a mixture of several molecules as shown in the diagram below. This diagram shows the isomers graphically for polymer P2r, where the structures below the depiction of the chain show each regio- and positional isomer possible for the monomer unit adjacent to the chain transfer agent and the end groups on each side of the main polymer chain. Each end group on the polymer may be independently selected from the groups shown on the left or right while the central portion of the polymer including the chain transfer agent and its two adjacent monomer units may be independently selected from the groups shown. In certain embodiments, the polymer composition comprises a mixture of all possible combinations of these. In other embodiments, the polymer composition is enriched in one or more of these.

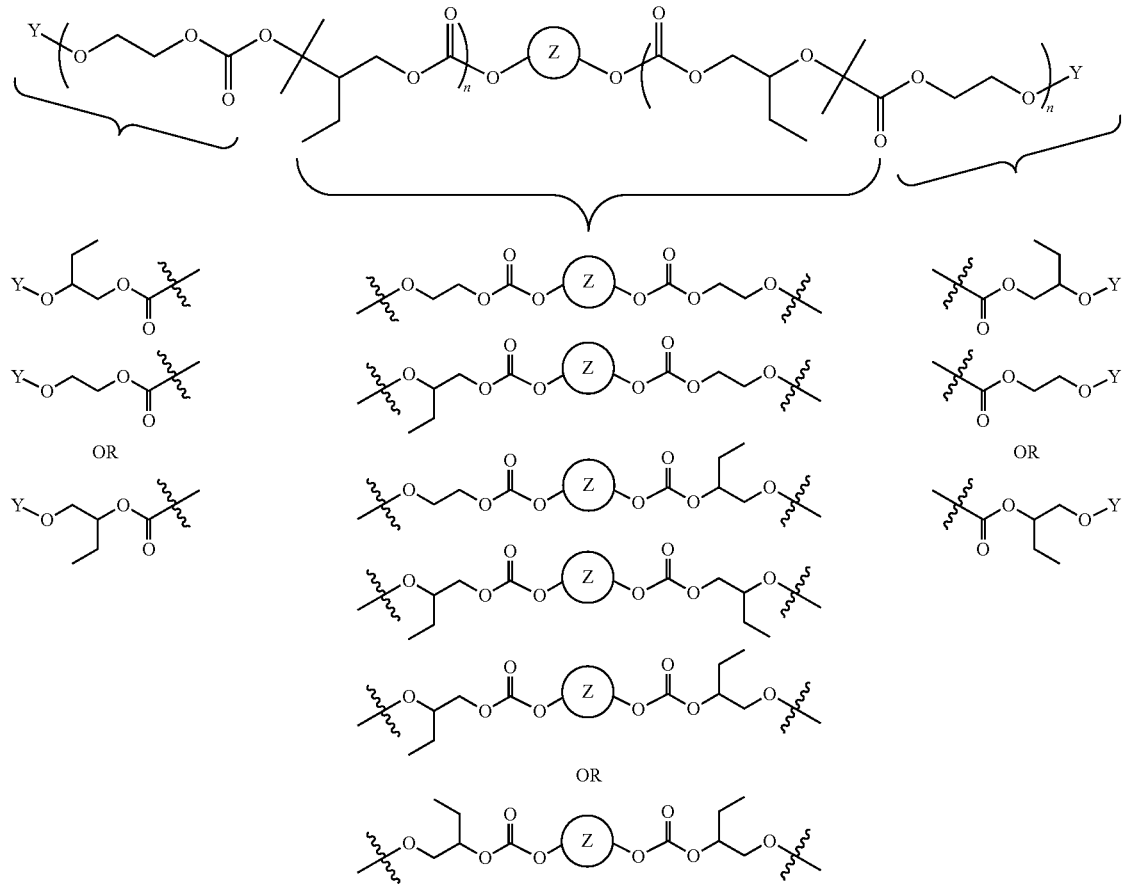

In certain embodiments, the aliphatic polycarbonate polyol is selected from the group consisting of Q1, Q2, Q3, Q4, Q5, Q6, and mixtures of any two or more of these.

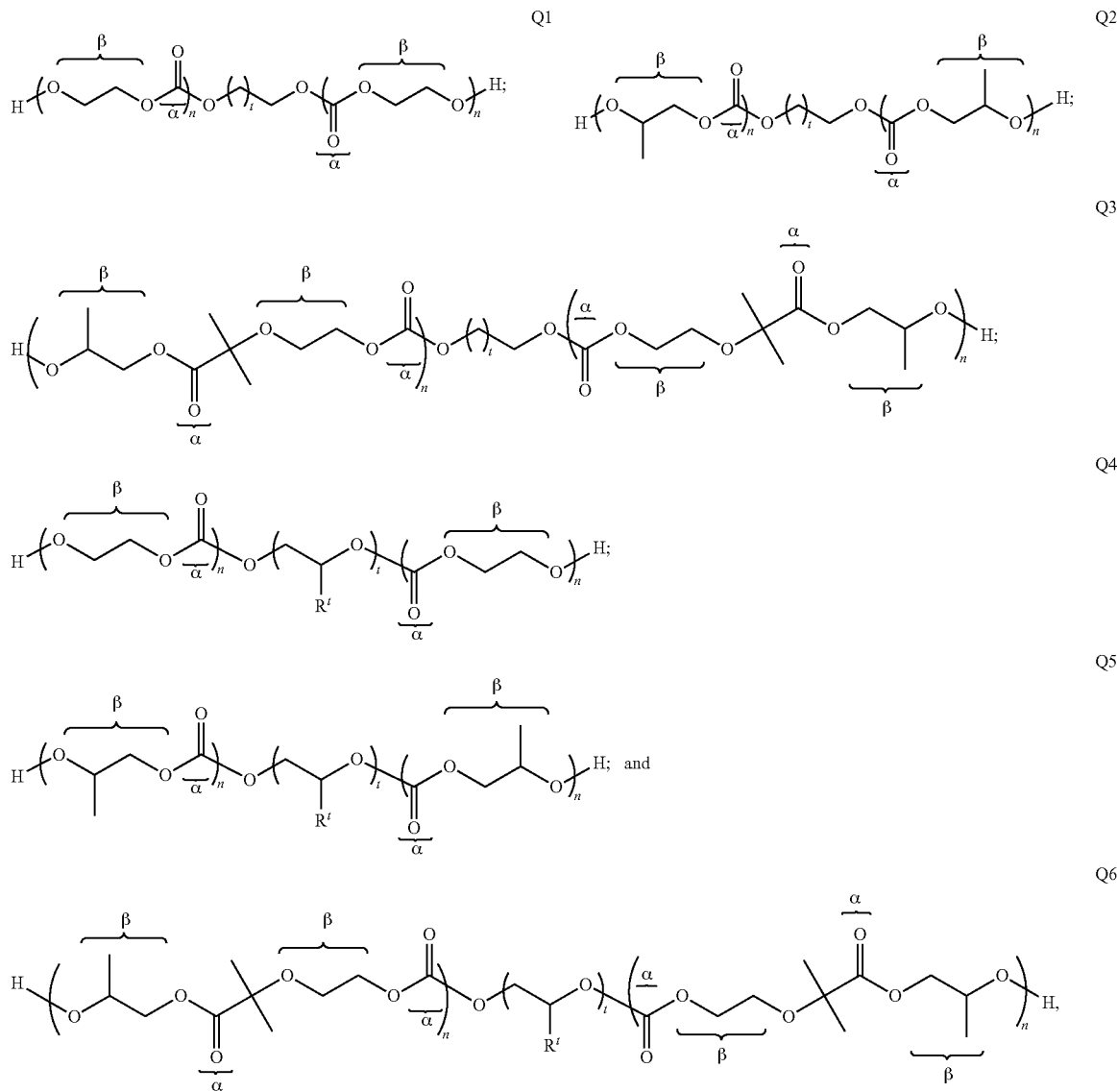

where α, β, and n are as described above and herein; and; t is an integer from 1 to 12 inclusive, and $R^t$ is independently at each occurrence —H, or —CH$_3$.

In certain embodiments, the aliphatic polycarbonate polyol is selected from the group consisting of:
Poly(ethylene carbonate) of formula Q1 having an average molecular weight number of between about 500 g/mol and about 3,000 g/mol, a polydispersity index less than about 1.25, at least 85% carbonate linkages, and at least 98% —OH end groups:
Poly(ethylene carbonate) of formula Q1 having an average molecular weight number of about 500 g/mol, a polydispersity index less than about 1.25, at least 85% carbonate linkages, and at least 98% —OH end groups:
Poly(ethylene carbonate) of formula Q1 having an average molecular weight number of about 1,000 g/mol, a polydispersity index less than about 1.25, at least 85% carbonate linkages, and at least 98% —OH end groups:
Poly(ethylene carbonate) of formula Q1 having an average molecular weight number of about 2,000 g/mol, a polydispersity index less than about 1.25, at least 85% carbonate linkages, and at least 98% —OH end groups;
Poly(ethylene carbonate) of formula Q1 having an average molecular weight number of about 3,000 g/mol, a polydispersity index less than about 1.25, at least 85% carbonate linkages, and at least 98% —OH end groups:
Poly(propylene carbonate) of formula Q2 having an average molecular weight number of between about 500 g/mol and about 3,000 g/mol, a polydispersity index less than about 1.25, at least 95% carbonate linkages, and at least 98% —OH end groups:
Poly(propylene carbonate) of formula Q2 having an average molecular weight number of about 500) g/mol, a polydispersity index less than about 1.25, at least 95% carbonate linkages, and at least 98% —OH end groups:

Poly(propylene carbonate) of formula Q2 having an average molecular weight number of about 1,000 g/mol, a polydispersity index less than about 1.25, at least 95% carbonate linkages, and at least 98% —OH end groups:
Poly(propylene carbonate) of formula Q2 having an average molecular weight number of about 2,000 g/mol, a polydispersity index less than about 1.25, at least 95% carbonate linkages, and at least 98% —OH end groups;
Poly(propylene carbonate) of formula Q2 having an average molecular weight number of about 3,000 g/mol, a polydispersity index less than about 1.25, at least 95% carbonate linkages, and at least 98% —OH end groups;
Poly(ethylene-co-propylene carbonate) of formula Q3 having an average molecular weight number of between about 500 g/mol and about 3,000 g/mol, a polydispersity index less than about 1.25, at least 90% carbonate linkages, and at least 98% —OH end groups;
Poly(ethylene-co-propylene carbonate) of formula Q3 having an average molecular weight number of about 500 g/mol, a polydispersity index less than about 1.25, at least 90% carbonate linkages, and at least 98% —OH end groups:
Poly(ethylene-co-propylene carbonate) of formula Q3 having an average molecular weight number of about 1,000 g/mol, a polydispersity index less than about 1.25, at least 90% carbonate linkages, and at least 98% —OH end groups;
Poly(ethylene-co-propylene carbonate) of formula Q3 having an average molecular weight number of about 2,000 g/mol (e.g., n is on average between about 10 and about 11), a polydispersity index less than about 1.25, at least 90% carbonate linkages, and at least 98% —OH end groups:
Poly(ethylene-co-propylene carbonate) of formula Q3 having an average molecular weight number of about 3,000 g/mol, a polydispersity index less than about 1.25, at least 95% carbonate linkages, and at least 98% —OH end groups;
Poly(ethylene carbonate) of formula Q4 having an average molecular weight number of between about 500 g/mol and about 3,000 g/mol (e.g., each n is between about 4 and about 16), a polydispersity index less than about 1.25, at least 95% carbonate linkages, and at least 98% —OH end groups;
Poly(ethylene carbonate) of formula Q4 having an average molecular weight number of about 500) g/mol, a polydispersity index less than about 1.25, at least 85% carbonate linkages, and at least 98% —OH end groups:
Poly(ethylene carbonate) of formula Q4 having an average molecular weight number of about 1,000 g/mol, a polydispersity index less than about 1.25, at least 85% carbonate linkages, and at least 98% —OH end groups:
Poly(ethylene carbonate) of formula Q4 having an average molecular weight number of about 2,000 g/mol, a polydispersity index less than about 1.25, at least 85% carbonate linkages, and at least 98% —OH end groups;
Poly(ethylene carbonate) of formula Q4 having an average molecular weight number of about 3,000 g/mol, a polydispersity index less than about 1.25, at least 85% carbonate linkages, and at least 98% —OH end groups.
Poly(propylene carbonate) of formula Q5 having an average molecular weight number of between about 500 g/mol and about 3,000 g/mol, a polydispersity index less than about 1.25, at least 95% carbonate linkages, and at least 98% —OH end groups;
Poly(propylene carbonate) of formula Q5 having an average molecular weight number of about 500 g/mol, a polydispersity index less than about 1.25, at least 95% carbonate linkages, and at least 98% —OH end groups;
Poly(propylene carbonate) of formula Q5 having an average molecular weight number of about 1,000 g/mol, a polydispersity index less than about 1.25, at least 95% carbonate linkages, and at least 98% —OH end groups:
Poly(propylene carbonate) of formula Q5 having an average molecular weight number of about 2,000 g/mol, a polydispersity index less than about 1.25, at least 95% carbonate linkages, and at least 98% —OH end groups;
Poly(propylene carbonate) of formula Q5 having an average molecular weight number of about 3,000 g/mol, a polydispersity index less than about 1.25, at least 95% carbonate linkages, and at least 98% —OH end groups;
Poly(ethylene-co-propylene carbonate) of formula Q6 having an average molecular weight number of between about 500 g/mol and about 3,000 g/mol, a polydispersity index less than about 1.25, at least 90% carbonate linkages, and at least 98% —OH end groups;
Poly(ethylene-co-propylene carbonate) of formula Q6 having an average molecular weight number of about 500 g/mol, a polydispersity index less than about 1.25, at least 90% carbonate linkages, and at least 98% —OH end groups:
Poly(ethylene-co-propylene carbonate) of formula Q6 having an average molecular weight number of about 1,000 g/mol, a polydispersity index less than about 1.25, at least 90% carbonate linkages, and at least 98% —OH end groups:
Poly(ethylene-co-propylene carbonate) of formula Q6 having an average molecular weight number of about 2,000 g/mol (, n is on average between about 10 and about 11), a polydispersity index less than about 1.25, at least 90% carbonate linkages, and at least 98% —OH end groups;
Poly(ethylene-co-propylene carbonate) of formula Q6 having an average molecular weight number of about 3,000 g/mol, a polydispersity index less than about 1.25, at least 95% carbonate linkages, and at least 98% —OH end groups; and Mixtures of any two or more of these.

In certain embodiments, the aliphatic polycarbonate polyol is selected from the group consisting of:
a) Poly(propylene carbonate) of formula P2a having a number average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 65 and 85%, and characterized in that the carbon atoms comprising the carbonate linkages in the polymer have a pMC of less than 10.
b) Poly(propylene carbonate) of formula P2a having a number average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 65 and 75%, and characterized in that the moiety $$\boxed{Z}$$

is not derived from biomass, and the carbon atoms comprising the carbonate linkages in the polymer have a pMC of less than 10; and
c) Poly(propylene carbonate) of formula P2a having a number average molecular weight number of between about 500 g/mol and about 3,000 g/mol, a polydispersity index less than about 1.25, at least 85% carbonate linkages, and at least 98% —OH end groups, an overall % biobased carbon value according to ASTM D6866-16 (Method B) of between 75 and 85%, and characterized in that the moiety

is derived from biomass, and the carbon atoms comprising the carbonate linkages in the polymer have a pMC of less than 10.

d) Poly(ethylene carbonate) of formula P2c having a number average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 55 and 75%, and characterized in that the carbon atoms comprising the carbonate linkages in the polymer have a pMC of less than 10.

e) Poly(ethylene carbonate) of formula P2c having a number average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 55 and 65%, and characterized in that the moiety

is not derived from biomass, and the carbon atoms comprising the carbonate linkages in the polymer have a pMC of less than 10; and f) Poly(ethylene carbonate) of formula P2c having a number average molecular weight number of between about 500 g/mol and about 3,000 g/mol, a polydispersity index less than about 1.25, at least 85% carbonate linkages, and at least 98% —OH end groups, an overall % biobased carbon value according to ASTM D6866-16 (Method B) of between 65 and 75%, and characterized in that the moiety

is derived from biomass, and the carbon atoms comprising the carbonate linkages in the polymer have a pMC of less than 10.

g) Poly(propylene carbonate) of formula P2a having a number average molecular weight number of between about 500 g/mol and about 3,000 g/mol, a polydispersity index less than about 1.25, at least 90% carbonate linkages, and at least 98% —OH end groups, an overall % biobased carbon according to ASTM D6866-16 (Method B) of between 65 and 85%, and characterized in that the carbon atoms comprising the carbonate linkages in the polymer have a pMC of less than 10.

h) Poly(propylene carbonate) of formula P2a having a number average molecular weight number of between about 500 g/mol and about 3,000 g/mol, a polydispersity index less than about 1.25, at least 90% carbonate linkages, and at least 98% —OH end groups, an overall % biobased carbon according to ASTM D6866-16 (Method B) of between 65 and 75%, and characterized in that the moiety

is not derived from biomass, and the carbon atoms comprising the carbonate linkages in the polymer have a pMC of less than 10; and i) Poly(propylene carbonate) of formula P2a having a number average molecular weight number of between about 500 g/mol and about 3,000 g/mol, a polydispersity index less than about 1.25, at least 90% carbonate linkages, and at least 98% —OH end groups, an overall % biobased carbon value according to ASTM D6866-16 (Method B) of between 75 and 85%, and characterized in that the moiety

is derived from biomass, and the carbon atoms comprising the carbonate linkages in the polymer have a pMC of less than 10.

j) Poly(ethylene carbonate) of formula P2c having a number average molecular weight number of between about 500 g/mol and about 3,000 g/mol, a polydispersity index less than about 1.25, at least 90% carbonate linkages, and at least 98% —OH end groups, an overall % biobased carbon according to ASTM D6866-16 (Method B) of between 55 and 75%, and characterized in that the carbon atoms comprising the carbonate linkages in the polymer have a pMC of less than 10.

k) Poly(ethylene carbonate) of formula P2c having a number average molecular weight number of between about 500 g/mol and about 3,000 g/mol, a polydispersity index less than about 1.25, at least 90% carbonate linkages, and at least 98% —OH end groups, an overall % biobased carbon according to ASTM D6866-16 (Method B) of between 55 and 65%, and characterized in that the moiety

is not derived from biomass, and the carbon atoms comprising the carbonate linkages in the polymer have a pMC of less than 10; and l) Poly(ethylene carbonate) of formula P2c having a number average molecular weight number of between about 500 g/mol and about 3,000 g/mol, a polydispersity index less than about 1.25, at least 90% carbonate linkages, and at least 98% —OH end groups, an overall % biobased carbon value according to ASTM D6866-16 (Method B) of between 65 and 75%, and characterized in that the moiety

is derived from biomass, and the carbon atoms comprising the carbonate linkages in the polymer have a pMC of less than 10.

m) Poly(propylene carbonate) of formula P2a having a number average molecular weight number of between about 500 g/mol and about 3,000 g/mol, a polydispersity index less than about 1.25, at least 95% carbonate linkages, and at least 98% —OH end groups, an overall % biobased carbon according to ASTM D6866-16 (Method B) of between 65 and 85%, and characterized in that the carbon atoms comprising the carbonate linkages in the polymer have a pMC of less than 10.

n) Poly(propylene carbonate) of formula P2a having a number average molecular weight number of between about 500 g/mol and about 3,000 g/mol, a polydispersity index less than about 1.25, at least 95% carbonate linkages, and at least 98% —OH end groups, an overall % biobased carbon according to ASTM D6866-16 (Method B) of between 65 and 75%, and characterized in that the moiety

is not derived from biomass, and the carbon atoms comprising the carbonate linkages in the polymer have a pMC of less than 10; and o) Poly(propylene carbonate) of formula P2a having a number average molecular weight number of between about 500 g/mol and about 3,000 g/mol, a polydispersity index less than about 1.25, at least 95% carbonate linkages, and at least 98% —OH end groups, an overall % biobased carbon value according to ASTM D6866-16 (Method B) of between 75 and 85%, and characterized in that the moiety

is derived from biomass, and the carbon atoms comprising the carbonate linkages in the polymer have a pMC of less than 10.

p) Poly(ethylene carbonate) of formula P2c having a number average molecular weight number of between about 500 g/mol and about 3,000 g/mol, a polydispersity index less than about 1.25, at least 95% carbonate linkages, and at least 98% —OH end groups, an overall % biobased carbon according to ASTM D6866-16 (Method B) of between 55 and 75%, and characterized in that the carbon atoms comprising the carbonate linkages in the polymer have a pMC of less than 10.

q) Poly(ethylene carbonate) of formula P2c having a number average molecular weight number of between about 500 g/mol and about 3,000 g/mol, a polydispersity index less than about 1.25, at least 95% carbonate linkages, and at least 98% —OH end groups, an overall % biobased carbon according to ASTM D6866-16 (Method B) of between 55 and 65%, and characterized in that the moiety

is not derived from biomass, and the carbon atoms comprising the carbonate linkages in the polymer have a pMC of less than 10; and r) Poly(ethylene carbonate) of formula P2c having a number average molecular weight number of between about 500 g/mol and about 3,000 g/mol, a polydispersity index less than about 1.25, at least 95% carbonate linkages, and at least 98% —OH end groups, an overall % biobased carbon value according to ASTM D6866-16 (Method B) of between 65 and 75%, and characterized in that the moiety

is derived from biomass, and the carbon atoms comprising the carbonate linkages in the polymer have a pMC of less than 10.

In certain embodiments, for these polycarbonates (a), (b), (c), (d), (e), (f), (g), (h), (i), (j), (k), (l), (m), (n), (o), (p), (q), and (r), the moiety

is selected from the group consisting of: ethylene glycol, diethylene glycol, triethylene glycol, 1,3 propane diol; 1,4 butane diol, hexylene glycol, 1,6 hexane diol, neopentyl glycol, propylene glycol, dipropylene glycol, tripopylene glycol, and alkoxylated derivatives of any of these.

In certain embodiments, the aliphatic polycarbonate polyol is selected from the group consisting of:

s) Poly(propylene carbonate) of formula P3a having a number average molecular weight number of between about 1,000 g/mol and about 4,000 g/mol, a polydispersity index less than about 1.25, at least 85% carbonate linkages, and at least 98% —OH end groups, an overall % biobased carbon according to ASTM D6866-16 (Method B) of between 65 and 85%, and characterized in that the carbon atoms comprising the carbonate linkages in the polymer have a pMC of less than 10.

t) Poly(propylene carbonate) of formula P3a having a number average molecular weight number of between about 1,000 g/mol and about 4,000 g/mol, a polydispersity index less than about 1.25, at least 85% carbonate linkages, and at least 98% —OH end groups, an overall % biobased carbon according to ASTM D6866-16 (Method B) of between 65 and 75%, and characterized in that the moiety

is not derived from biomass, and the carbon atoms comprising the carbonate linkages in the polymer have a pMC of less than 10; and u) Poly(propylene carbonate) of formula P3a having a number average molecular weight number of between about 1,000 g/mol and about 4,000 g/mol, a polydispersity index less than about 1.25, at least 85% carbonate linkages, and at least 98% —OH end groups, an overall % biobased carbon value according to ASTM D6866-16 (Method B) of between 75 and 85%, and characterized in that the moiety

is derived from biomass, and the carbon atoms comprising the carbonate linkages in the polymer have a pMC of less than 10.

v) Poly(ethylene carbonate) of formula P3c having a number average molecular weight number of between about 1,000 g/mol and about 4,000 g/mol, a polydispersity index less than about 1.25, at least 85% carbonate linkages, and at least 98% —OH end groups, an overall % biobased carbon according to ASTM D6866-16 (Method B) of between 55 and 75%, and characterized in that the carbon atoms comprising the carbonate linkages in the polymer have a pMC of less than 10.

w) Poly(ethylene carbonate) of formula P3c having a number average molecular weight number of between about 1,000 g/mol and about 4,000 g/mol, a polydispersity index less than about 1.25, at least 85% carbonate linkages, and at least 98% —OH end groups, an overall % biobased carbon according to ASTM D6866-16 (Method B) of between 55 and 65%, and characterized in that the moiety

is not derived from biomass, and the carbon atoms comprising the carbonate linkages in the polymer have a pMC of less than 10; and x) Poly(ethylene carbonate) of formula P3c having a number average molecular weight number of between about 1,000 g/mol and about 4,000 g/mol, a polydispersity index less than about 1.25, at least 85% carbonate linkages, and at least 98% —OH end groups, an overall % biobased carbon value according to ASTM D6866-16 (Method B) of between 65 and 75%, and characterized in that the moiety

is derived from biomass, and the carbon atoms comprising the carbonate linkages in the polymer have a pMC of less than 10.

y) Poly(propylene carbonate) of formula P3a having a number average molecular weight number of between about 1,000 g/mol and about 4,000 g/mol, a polydispersity index less than about 1.25, at least 90% carbonate linkages, and at least 98% —OH end groups, an overall % biobased carbon according to ASTM D6866-16 (Method B) of between 65 and 85%, and characterized in that the carbon atoms comprising the carbonate linkages in the polymer have a pMC of less than 10.

z) Poly(propylene carbonate) of formula P3a having a number average molecular weight number of between about 1,000 g/mol and about 4,000 g/mol, a polydispersity index less than about 1.25, at least 90% carbonate linkages, and at least 98% —OH end groups, an overall % biobased carbon according to ASTM D6866-16 (Method B) of between 65 and 75%, and characterized in that the moiety

is not derived from biomass, and the carbon atoms comprising the carbonate linkages in the polymer have a pMC of less than 10; and aa) Poly(propylene carbonate) of formula P3a having a number average molecular weight number of between about 1,000 g/mol and about 4,000 g/mol, a polydispersity index less than about 1.25, at least 90% carbonate linkages, and at least 98% —OH end groups, an overall % biobased carbon value according to ASTM D6866-16 (Method B) of between 75 and 85%, and characterized in that the moiety

is derived from biomass, and the carbon atoms comprising the carbonate linkages in the polymer have a pMC of less than 10.

bb) Poly(ethylene carbonate) of formula P3c having a number average molecular weight number of between about 1,000 g/mol and about 4,000 g/mol, a polydispersity index less than about 1.25, at least 90% carbonate linkages, and at least 98% —OH end groups, an overall % biobased carbon according to ASTM D6866-16 (Method B) of between 55 and 75%, and characterized in that the carbon atoms comprising the carbonate linkages in the polymer have a pMC of less than 10.

cc) Poly(ethylene carbonate) of formula P3c having a number average molecular weight number of between about 1,000 g/mol and about 4,000 g/mol, a polydispersity index less than about 1.25, at least 90% carbonate linkages, and at least 98% —OH end groups, an overall % biobased carbon according to ASTM D6866-16 (Method B) of between 55 and 65%, and 65 and characterized in that the moiety

is not derived from biomass, and the carbon atoms comprising the carbonate linkages in the polymer have a pMC of less than 10; and dd) Poly(ethylene carbonate) of formula P3c having a number average molecular weight number of between about 1,000 g/mol and about 4,000 g/mol, a polydispersity index less than about 1.25, at least 90% carbonate linkages, and at least 98% —OH end groups, an overall % biobased carbon value according to ASTM D6866-16 (Method B) of between 65 and 75%, and characterized in that the moiety (Z)

is derived from biomass, and the carbon atoms comprising the carbonate linkages in the polymer have a pMC of less than 10.
- ee) Poly(propylene carbonate) of formula P3a having a number average molecular weight number of between about 1,000 g/mol and about 4,000 g/mol, a polydispersity index less than about 1.25, at least 95% carbonate linkages, and at least 98% —OH end groups, an overall % biobased carbon according to ASTM D6866-16 (Method B) of between 65 and 85%, and characterized in that the carbon atoms comprising the carbonate linkages in the polymer have a pMC of less than 10.
- ff) Poly(propylene carbonate) of formula P3a having a number average molecular weight number of between about 1,000 g/mol and about 4,000 g/mol, a polydispersity index less than about 1.25, at least 95% carbonate linkages, and at least 98% —OH end groups, an overall % biobased carbon according to ASTM D6866-16 (Method B) of between 65 and 75%, and characterized in that the moiety (Z)

is not derived from biomass, and the carbon atoms comprising the carbonate linkages in the polymer have a pMC of less than 10; and
- gg) Poly(propylene carbonate) of formula P3a having a number average molecular weight number of between about 1,000 g/mol and about 4,000 g/mol, a polydispersity index less than about 1.25, at least 95% carbonate linkages, and at least 98% —OH end groups, an overall % biobased carbon value according to ASTM D6866-16 (Method B) of between 75 and 85%, and characterized in that the moiety (Z)

is derived from biomass, and the carbon atoms comprising the carbonate linkages in the polymer have a pMC of less than 10.
- hh) Poly(ethylene carbonate) of formula P3c having a number average molecular weight number of between about 1,000 g/mol and about 4,000 g/mol, a polydispersity index less than about 1.25, at least 95% carbonate linkages, and at least 98% —OH end groups, an overall % biobased carbon according to ASTM D6866-16 (Method B) of between 55 and 75%, and characterized in that the carbon atoms comprising the carbonate linkages in the polymer have a pMC of less than 10.
- ii) Poly(ethylene carbonate) of formula P3c having a number average molecular weight number of between about 1,000 g/mol and about 4,000 g/mol ol, a polydispersity index less than about 1.25, at least 95% carbonate linkages, and at least 98% —OH end groups, an overall % biobased carbon according to ASTM D6866-16 (Method B) of between 55 and 65%, and characterized in that the moiety (z)

is not derived from biomass, and the carbon atoms comprising the carbonate linkages in the polymer have a pMC of less than 10; and
- jj) Poly(ethylene carbonate) of formula P3c having a number average molecular weight number of between about 1,000 g/mol and about 4,000 g/mol, a polydispersity index less than about 1.25, at least 95% carbonate linkages, and at least 98% —OH end groups, an overall % biobased carbon value according to ASTM D6866-16 (Method B) of between 65 and 75%, and characterized in that the moiety (z)

is derived from biomass, and the carbon atoms comprising the carbonate linkages in the polymer have a pMC of less than 10.

In certain embodiments, for these polycarbonates (a), (b), (c), (d), (e), (f), (g), (h), (i), (j), (k), (l), (m), (n), (o), (p), (q), and (r), the moiety (z)

is selected from the group consisting of: glycerol, 1,2,4-butanetriol, 2-(hydroxymethyl)-1,3-propanediol; hexane triols, trimethylol propane, trimethylol ethane, trimethylolhexane, 1,2,4-cyclohexanetrimethanol, pentaerythritol mono esters, pentaerythritol mono ethers, and alkoxylated analogs of any of these. In certain embodiments, such alkoxylated derivatives comprise ethoxylated or propoxylated molecules.

In certain embodiments, the aliphatic polycarbonate polyol is selected from the group consisting of:
- kk) Poly(ethylene carbonate) of formula Q1 having a number average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 55 and 75%, and characterized in that the carbon atoms comprising the carbonate linkages in the polymer have a pMC of less than 10.
- ll) Poly(ethylene carbonate) of formula Q1 having an average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 55 and 65%, and characterized in that the moiety

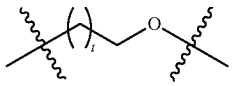

is not derived from biomass, and the carbon atoms comprising the carbonate linkages in the polymer have a pMC of less than 10.

mm) Poly(ethylene carbonate) of formula Q1 having an average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 65 and 75%, and characterized in that the moiety

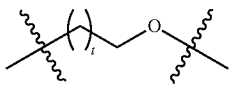

is derived from biomass, and the carbon atoms comprising the carbonate linkages in the polymer have a pMC of less than 10.

nn) Poly(propylene carbonate) of formula Q2 having a number average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 65 and 85%, and characterized in that the carbon atoms comprising the carbonate linkages in the polymer have a pMC of less than 10.

oo) Poly(propylene carbonate) of formula Q2 having an average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 65 and 75%, and characterized in that the moiety

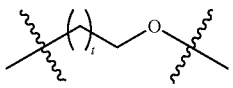

is not derived from biomass, and the carbon atoms comprising the carbonate linkages in the polymer have a pMC of less than 10.

pp) Poly(propylene carbonate) of formula Q2 having an average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 75 and 85%, and characterized in that the moiety

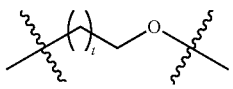

is derived from biomass, and the carbon atoms comprising the carbonate linkages in the polymer have a pMC of less than 10.

qq) Poly(ethylene-co-propylene carbonate) of formula Q3 having a number average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 55 and 85%, and characterized in that the carbon atoms comprising the carbonate linkages in the polymer have a pMC of less than 10.

rr) Poly(ethylene-co-propylene carbonate) of formula Q3 having an average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 55 and 70%, and characterized in that the moiety

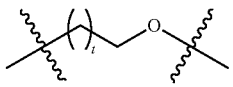

is not derived from biomass, and the carbon atoms comprising the carbonate linkages in the polymer have a pMC of less than 10.

ss) Poly(ethylene-co-propylene carbonate) of formula Q3 having an average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 70 and 85%, and characterized in that the moiety

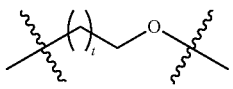

is derived from biomass, and the carbon atoms comprising the carbonate linkages in the polymer have a pMC of less than 10.

tt) Poly(ethylene carbonate) of formula Q4 having a number average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 55 and 75%, and characterized in that the carbon atoms comprising the carbonate linkages in the polymer have a pMC of less than 10.

uu) Poly(ethylene carbonate) of formula Q4 having an average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 55 and 65%, and characterized in that the moiety

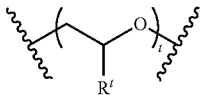

is not derived from biomass, and the carbon atoms comprising the carbonate linkages in the polymer have a pMC of less than 10.

vv) Poly(ethylene carbonate) of formula Q4 having an average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 65 and 75%, and characterized in that the moiety

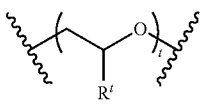

is derived from biomass, and the carbon atoms comprising the carbonate linkages in the polymer have a pMC of less than 10.

ww) Poly(propylene carbonate) of formula Q5 having a number average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 65 and 85%, and characterized in that the carbon atoms comprising the carbonate linkages in the polymer have a pMC of less than 10.

xx) Poly(propylene carbonate) of formula Q5 having an average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 65 and 75%, and characterized in that the moiety

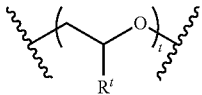

is not derived from biomass, and the carbon atoms comprising the carbonate linkages in the polymer have a pMC of less than 10.

yy) Poly(propylene carbonate) of formula Q5 having an average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 75 and 85%, and characterized in that the moiety

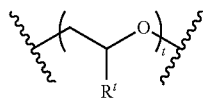

is derived from biomass, and the carbon atoms comprising the carbonate linkages in the polymer have a pMC of less than 10.

zz) Poly(ethylene-co-propylene carbonate) of formula Q6 having a number average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 55 and 85%, and characterized in that the carbon atoms comprising the carbonate linkages in the polymer have a pMC of less than 10.

aaa) Poly(ethylene-co-propylene carbonate) of formula Q6 having an average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 55 and 70%, and characterized in that the moiety

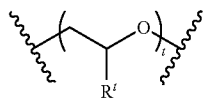

is not derived from biomass, and the carbon atoms comprising the carbonate linkages in the polymer have a pMC of less than 10.

bbb) Poly(ethylene-co-propylene carbonate) of formula Q6 having an average molecular weight number of between about 500 g/mol and about 3,000 g/mol, a polydispersity index less than about 1.25, at least 85% carbonate linkages, and at least 98% —OH end groups, an overall % biobased carbon according to ASTM D6866-16 (Method B) of between 70 and 85%, and characterized in that the moiety

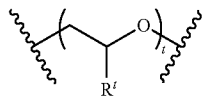

is derived from biomass, and the carbon atoms comprising the carbonate linkages in the polymer have a pMC of less than 10.

In certain embodiments, the

in the embedded chain transfer agent is a moiety derived from a polymeric diol or higher polyhydric alcohol. In certain embodiments, such polymeric alcohols are polyether or polyester polyols. In certain embodiments

is a polyether polyol comprising ethylene glycol or propylene glycol repeating units (—OCH$_2$CH$_2$O—, or —OCH$_2$CH(CH$_3$)O—) or combinations of these. In certain embodiments,

is a polyester polyol comprising the reaction product of a diol and a diacid, or a material derived from ring-opening polymerization of one or more lactones. In certain embodiments, any of the above polymeric diols or higher polyhydric alcohols are characterized in that they are derived from biomass.

In certain embodiments where

comprises a polyether diol, the aliphatic polycarbonate polyol has a structure Q7:

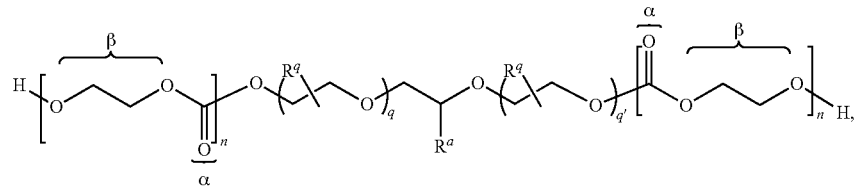

Q7 wherein,
R$^q$ is at each occurrence in the polymer chain independently —H or —CH$_3$;
R$^a$ is —H, or —CH$_3$;
q and q' are independently an integer from about 0 to about 40; and
and n, α, and β are as described above and herein.

In certain embodiments, an aliphatic polycarbonate polyol is selected from the group consisting of:

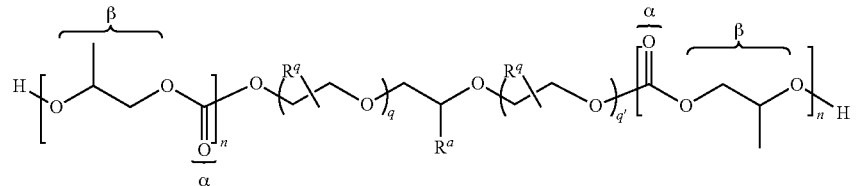

Q7a

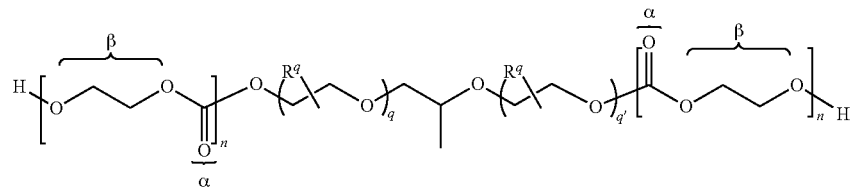

Q7b

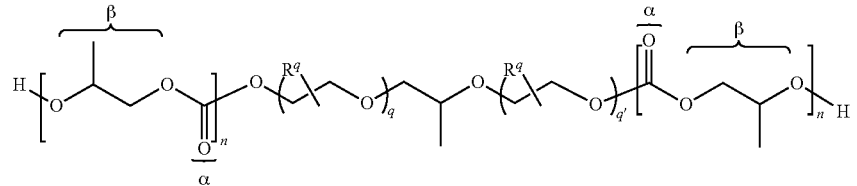

Q7c

Q7d
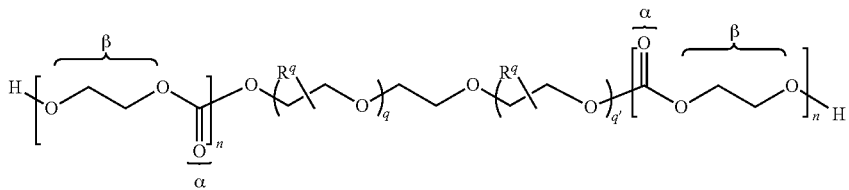
Q7e
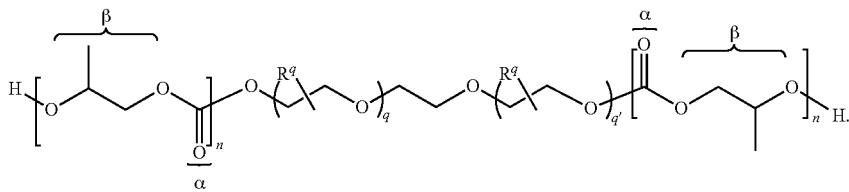
In certain embodiments where
○ Z  (30)
comprises a polyether diol characterized in that the polyether diol is derived from biomass, the aliphatic polycarbonate polyol has a structure Q7':
Q7'
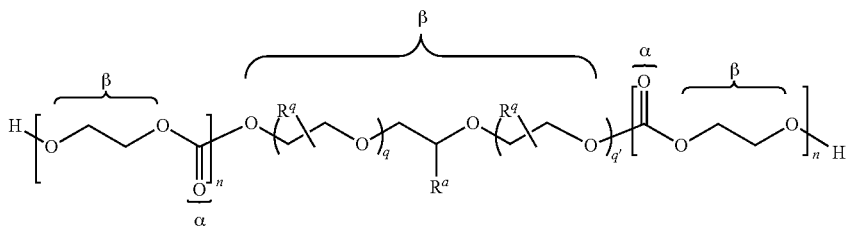
wherein $R^q$, $R^a$, q, q', n, o, and are as described above and herein.
In certain embodiments, an aliphatic polycarbonate polyol is selected from the group consisting of:
Q7a'
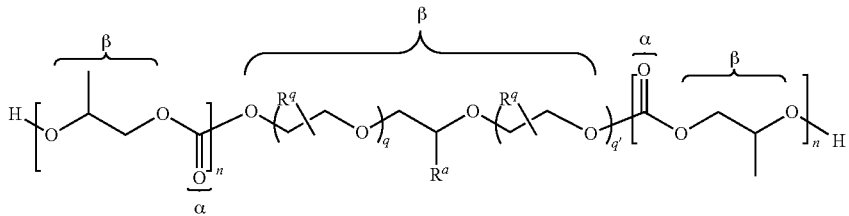

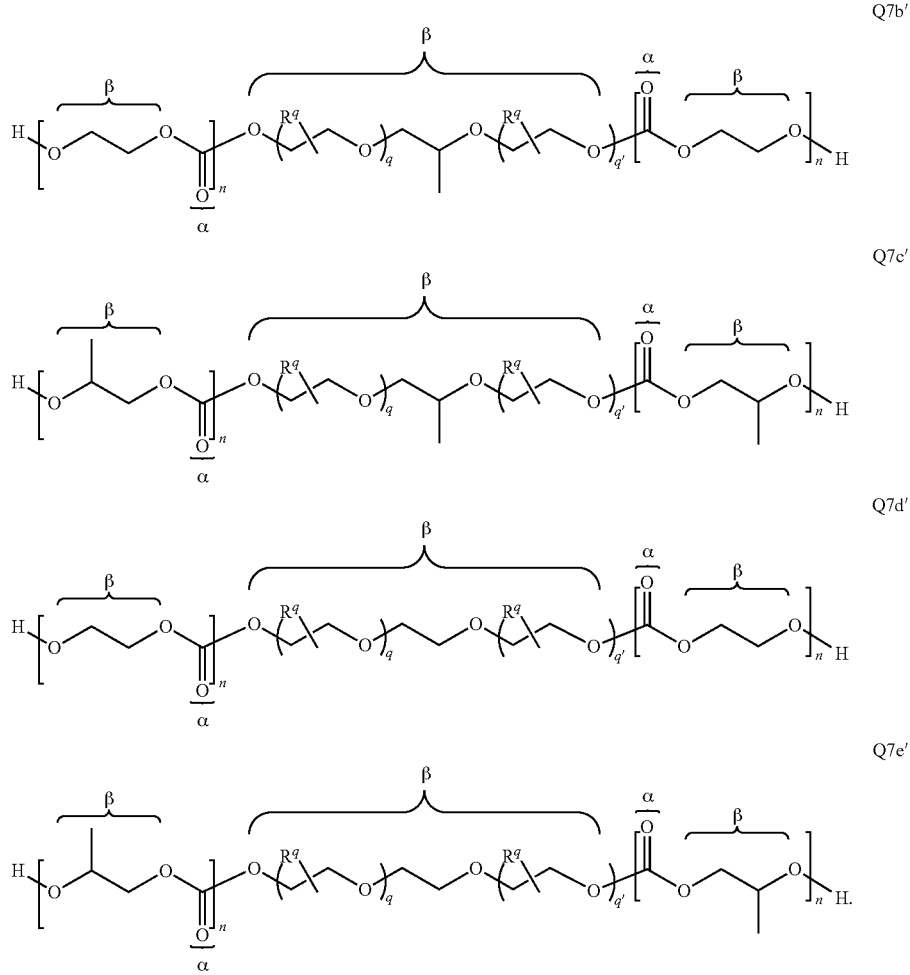

In certain embodiments, where aliphatic polycarbonate polyols comprise molecules conforming to structure Q7 or Q7', the moiety

is derived from a commercially available polyether polyol such as those typically used in the formulation of polyurethane compositions.

In certain embodiments where

comprises a polyester diol, the aliphatic polycarbonate polyol has a structure Q8:

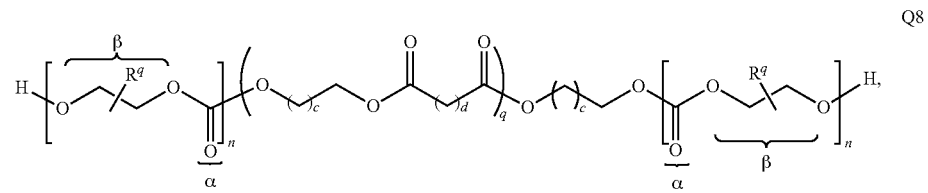

wherein,
c at each occurrence in the polymer chain independently is an integer from 0 to 6;
d at each occurrence in the polymer chain independently is an integer from 1 to 11; and
each of $R^q$, n, q, α, and β is as described above and herein.

In certain embodiments, an aliphatic polycarbonate polyol is selected from the group consisting of:

Q8a
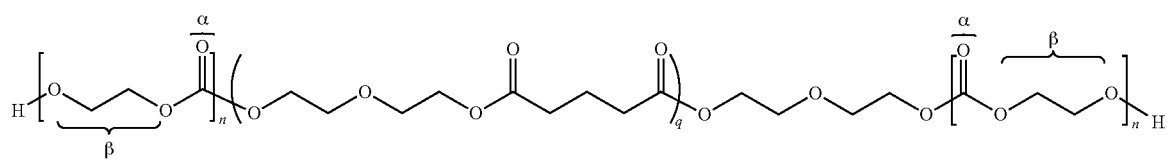

Q8b
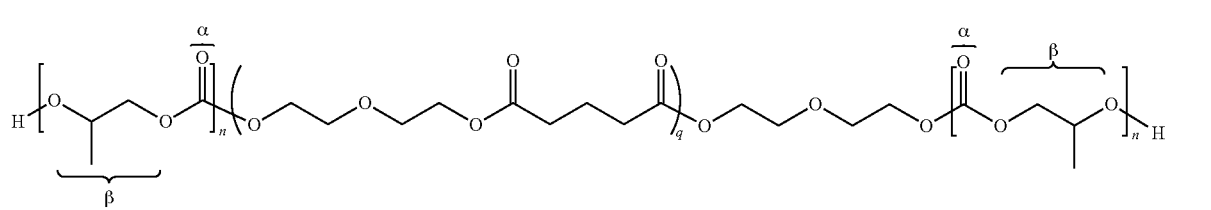

Q8c
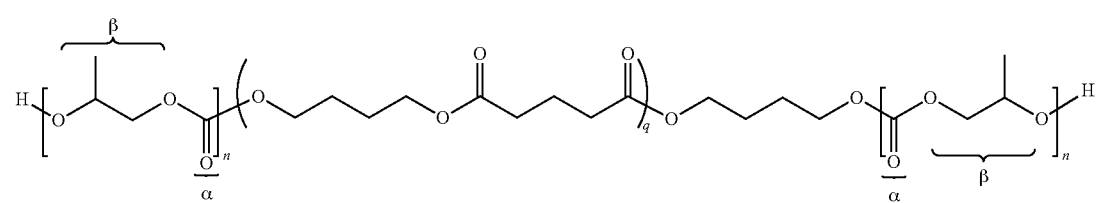

Q8d
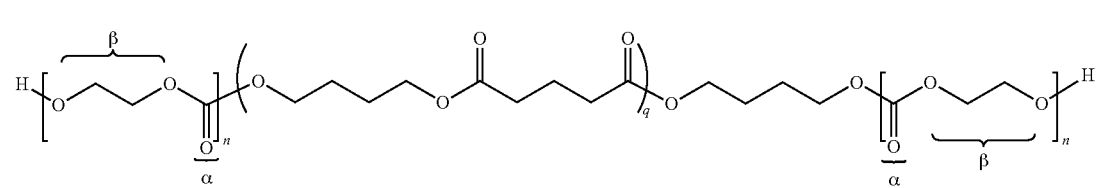

Q8e
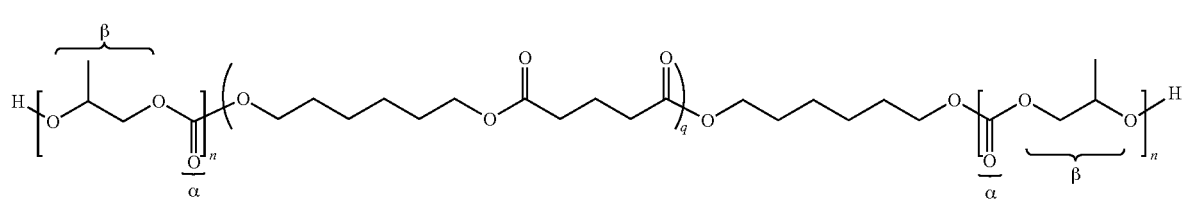

Q8f
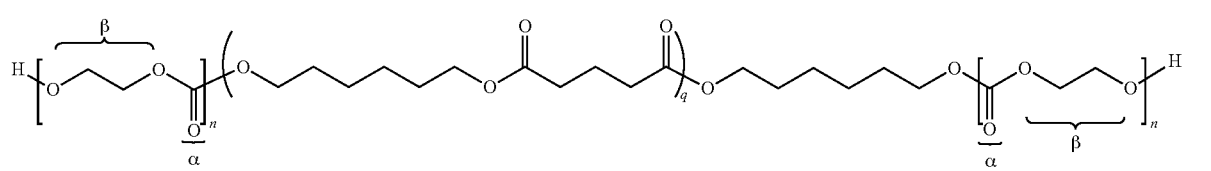

where α, β, q, and n are as described above and herein.

In certain embodiments of formulae Q8, Q8a, Q8b, Q8c, Q8d, Q8e, or Q8f where the polycarbonate derived a polyester polyol, the polyester is characterized in that it is derived from biomass.

In certain embodiments, where aliphatic polycarbonate polyols comprise molecules conforming to structure Q8, the moiety

is derived from a commercially available polyester polyol such as those typically used in the formulation of polyurethane compositions.

ii. Polyether Carbonates

In certain embodiments, polymer compositions of the present invention comprise polyether carbonates (i.e., polymer chains containing carbonate linkages as described above, and ether linkages). In some embodiments, such polyether carbonates are both biobased and fossil-carbon sequestering.

In certain embodiments, polymer compositions of the present invention comprise polyether polycarbonate chains comprising a structure:

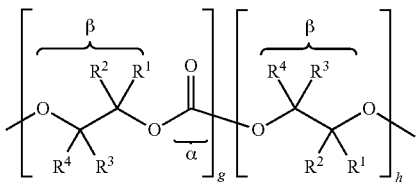

I wherein
each $R^1$, $R^2$, $R^3$, $R^4$, $\alpha$, and $\beta$ is described above and herein; and
g and h are independently an integer from about 0 to about 500, wherein, on average in the composition, the value of h is greater than g.

In some embodiments, the value of h is at least about twice the value of g. In some embodiments, the value of h is at least about three times, at least about four times, at least about five times, at least about ten times, at least about 20 times, at least about 50 times, or at least about 100 times greater than the value of g.

In certain embodiments, polymer compositions of the present invention comprise polycarbonate polymers containing both carbonate linkages and ether linkages. In some embodiments, the percentage of carbonate linkages (or ether linkages) may be determined by $^1$H or $^{13}$C NMR spectroscopy.

In some embodiments, polyether carbonates of the present invention are characterized in that, on average in the composition, the percentage of carbonate linkages is between about 5% and about 50%. In some embodiments, polyether carbonates of the present invention are characterized in that, on average in the composition, the percentage of carbonate linkages is between about 10% and about 50%. In some embodiments, polyether carbonates of the present invention are characterized in that, on average in the composition, the percentage of carbonate linkages is between about 15% and about 50%. In some embodiments, polyether carbonates of the present invention are characterized in that, on average in the composition, the percentage of carbonate linkages is between about 20% and about 50%. In some embodiments, polyether carbonates of the present invention are characterized in that, on average in the composition, the percentage of carbonate linkages is between about 25% and about 50%. In some embodiments, polyether carbonates of the present invention are characterized in that, on average in the composition, the percentage of carbonate linkages is between about 30% and about 50%. In some embodiments, polyether carbonates of the present invention are characterized in that, on average in the composition, the percentage of carbonate linkages is between about 35% and about 50%. In some embodiments, polyether carbonates of the present invention are characterized in that, on average in the composition, the percentage of carbonate linkages is between about 40% and about 50%. In some embodiments, polyether carbonates of the present invention are characterized in that, on average in the composition, the percentage of carbonate linkages is between about 45% and about 50%. In some embodiments, polyether carbonates of the present invention are characterized in that, on average in the composition, the percentage of carbonate linkages is between about 5% and about 40%. In some embodiments, polyether carbonates of the present invention are characterized in that, on average in the composition, the percentage of carbonate linkages is between about 5% and about 30%. In some embodiments, polyether carbonates of the present invention are characterized in that, on average in the composition, the percentage of carbonate linkages is between about 5% and about 20%. In some embodiments, polyether carbonates of the present invention are characterized in that, on average in the composition, the percentage of carbonate linkages is between about 5% and about 10%. In some embodiments, polyether carbonates of the present invention are characterized in that, on average in the composition, the percentage of carbonate linkages is between about 20% and about 50%. In some embodiments, polyether carbonates of the present invention are characterized in that, on average in the composition, the percentage of carbonate linkages is between about 20% and about 40%.

iii. Block Copolymers

In certain embodiments, polymer compositions of the present invention comprise block copolymers. In some embodiments, such block copolymers are both biobased and fossil-carbon sequestering. In certain embodiments, such block copolymers comprise (in addition to the aliphatic polycarbonate, or polyether carbonate) blocks comprising polyethers, polyesters, polyolefins, polyamides (e.g., nylon), polyimides, or combinations of two or more of these.

In some embodiments, provided block copolymers are of formula A-L-B, where A- is an aliphatic polycarbonate or polyether-carbonate chain as described above and herein, having from about 3 to about 500 repeating units, L is a linker moiety or a covalent bond, and —B is selected from the group consisting of polyethers, polyesters, polyolefins, polyamides, polyimides, and combinations of two or more of these, having from about 3 to about 500 repeating units.

In some embodiments, A- is an aliphatic polycarbonate as described above and herein. In some embodiments, A- is a polyether carbonate as described above and herein.

In certain embodiments, L is a covalent bond (i.e., A- is bonded directly to —B). In other embodiments, L is a polyfunctional moiety having appropriate functionality to form a covalent chemical bond with both the polycarbonate chain and the hydrophilic oligomer. In certain instances, L is a moiety formed by the reaction of one functional group on A- and one functional group on —B with a polyfunctional molecule capable of reaction with the functional groups on A- and —B thereby linking them. Examples of suitable polyfunctional moieties for L include, but are not limited to: agents that can form one or more linkages such as ester, amide, ether, amine, thioether, carbonate, or other similar linkages. Examples of polyfunctional molecules suitable for incorporation as L include, but are not limited to: phosgene, diacids, anhydrides, acrylates, diisocyanates, epoxides, diols, diamines, hydroxy mercaptans, mercapto acids, hydroxy acids, amino acids, and any precursors or reactive equivalents thereof.

In certain embodiments, a linker L is a moiety formed directly by the reaction of complementary functional groups on termini of A- and —B. Examples of such moieties include, but are not limited to: L being an ester, (formed from an alcohol group on the terminus of A- and a carboxy group on the terminus of —B, or vice versa); L being an amide; (formed from an amine group on the terminus of A- and a carboxy group on the terminus of —B, or vice versa); L being an olefin (formed, for example, by olefin metathesis); L being a heterocycle, (for example a triazole formed by cycloaddition of an azide and an alkyne), and L being a cyclohexene ring formed by Diels Alder cycloaddition of a diene and a dienophile.

In certain embodiments, a hydrophilic oligomer —B is a polyether chain. In some embodiments, —B is a polyolefin chain bearing hydrophilic functional groups. In certain embodiments, a hydrophilic oligomer —B is a polyamine chain. In certain embodiments, —B is selected from the group consisting of polyoxymethylene, poly(ethylene oxide), poly(propylene oxide), polyvinyl alcohol, poly(vinyl acetate), partially hydrolyzed poly(vinyl acetate), poly(acrylic acid), polyacrylamide, polyethyleneimine, poly(2-hydroxyethyl methacrylate), poly(N-vinylpyrrolidone), polypeptides, polysaccharides, polyepoxysuccinic acid, poly(methyl vinyl ether), poly(allylamine), poly(2-ethyl-2-oxazoline), and block, tapered or random copolymers of any two or more of the above. In some embodiments, —B is polyoxymethylene. In some embodiments, —B is poly(ethylene oxide). In some embodiments, —B is poly(propylene oxide).

In some embodiments, A- has about 3 to about 500 repeating units. In some embodiments, A- has about 3 to about 25 repeating units. In some embodiments. A- has about 3 to about 15 repeating units. In some embodiments, A- has about 3 to about 10 repeating units. In some embodiments, A- has about 10 to about 20 repeating units. In some embodiments, A- has about 10 to about 50 repeating units. In some embodiments, A- has about 10 to about 100 repeating units. In some embodiments, A- has about 50 to about 500 repeating units. In some embodiments, A- has about 100 to about 500 repeating units. In some embodiments, A- has about 250 to about 500 repeating units. In some embodiments, A- has about 350 to about 500 repeating units. In some embodiments, A- has about 10 to about 250 repeating units. In some embodiments, A- has about 50 to about 100 repeating units.

In some embodiments, B— has about 3 to about 500 repeating units. In some embodiments, B— has about 3 to about 25 repeating units. In some embodiments, B— has about 3 to about 15 repeating units. In some embodiments, B— has about 3 to about 10 repeating units. In some embodiments, B— has about 10 to about 20 repeating units. In some embodiments. A- has about 10 to about 50 repeating units. In some embodiments, B— has about 10 to about 100) repeating units. In some embodiments, B— has about 50 to about 500 repeating units. In some embodiments, B— has about 100 to about 500 repeating units. In some embodiments, B— has about 250 to about 500 repeating units. In some embodiments, B— has about 350 to about 500 repeating units. In some embodiments, B— has about 10 to about 250 repeating units. In some embodiments, B— has about 50 to about 100 repeating units.

II. Methods

In one aspect, the present invention provides methods of producing polymer compositions prepared using both the biobased carbon and and sequestered fossil $CO_2$. In some embodiments, the invention encompasses methods of producing polymer compositions whose manufacture sequesters $CO_2$ produced from a fossil carbon source while simultaneously utilizing biobased feedstocks as constituents of the polymer chain.

In some embodiments, the present invention provides methods comprising the steps of:
 a) converting the biobased ethanol or biobased glycerol to a biobased epoxide; and
 b) copolymerizing carbon dioxide sequestered from a fossil carbon source with the biobased epoxide to produce a polymer composition as described above and herein.

In some embodiments, the present invention provides methods comprising the steps of:
 a) fermenting carbohydrates derived from biomass to produce biobased ethanol;
 b) converting the biobased ethanol to a biobased epoxide; and
 c) copolymerizing carbon dioxide sequestered from a fossil carbon source with the biobased epoxide to produce a polymer composition as described above and herein.

In some embodiments, the present invention provides methods comprising the steps of:
 a) treating vegetable oil to produce biobased glycerol;
 b) converting the biobased glycerol to a biobased epoxide; and
 c) copolymerizing carbon dioxide sequestered from a fossil carbon source with the biobased epoxide to produce a polymer composition as described above and herein.

A. Methods of Manufacturing Biobased Ethanol and Biobased Glycerol i. Biobased Ethanol In certain embodiments, provided methods comprise a step of treating biomass to produce biobased ethanol (step (a)). Biobased ethanol is derived from biological feedstocks such as corn starch or cane sugar or glycerol obtained from biodiesel industry through a biological fermentation process.

In some embodiments, a biological source includes first generation, second generation, and third generation sources. In some embodiments, a first generation biological source is selected from the group consisting of corn, wheat, sugar beet, sugar-cane, sorghum, and potatoes. In some embodiments, a second generation biological source is selected from the group consisting of corn stover, wheat straw, bagasse, wood chips, switchgrass, pulp, and paper waste. In some embodiments, a third generation biological source includes algae and cyanobactrial strains genetically engineered to produce ethanol during autotrophic or heterotrophic growth.

Methods of treating a biomass to produce biobased ethanol are well known. For example, in some embodiments, a sugar is provided by a biological source, and the sugar is converted to ethanol through fermentation. In some embodiments, the sugar provided by a biological source is sucrose. In some embodiments, a sugar provided by a biological source is a starch or lignocellulose, which may be hydrolyzed to hexose sugars suitable for microbial fermentation.

In some embodiments, biobased ethanol has a % biobased carbon content measured according to ASTM D6866-16 (Method B) of 100%. In some embodiments, biobased ethanol has a pMC value measured according to ASTM D6866-16 (Method B) of about 95, 100, 102.5, 105, or 107.5.

ii. Biobased Glycerol

In certain embodiments, provided methods comprise a step of treating vegetable oil (triglycerides) to produce biobased glycerol (step (a)).

In some embodiments, the step of producing biobased glycerol comprises transesterification of triglycerides to produce biodiesel and biobased glycerol, as according to Scheme 3.

Scheme 3.

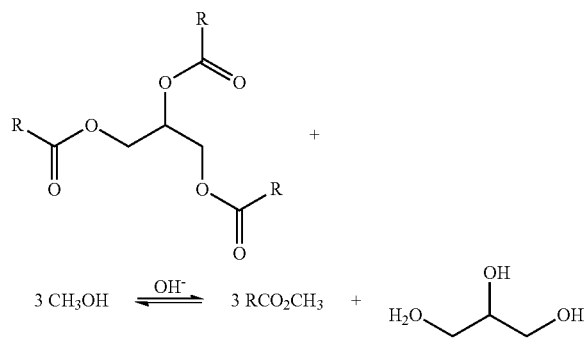

In some embodiments, the step of producing biobased glycerol comprises the step of treating triglycerides with a base catalyst.

B. Methods of Manufacturing Biobased Alkylene Oxides.

In certain embodiments, provided methods comprise a step of converting the biobased ethanol to a biobased epoxide (step (b)), e.g., a biobased alkylene oxide. For example, bio-ethanol is provided from a biological source and converted to biobased ethylene oxide or Biobased Propylene Oxide.

i. Production of Bio-Ethylene Oxide

Biobased ethylene oxide is, for example, manufactured by Croda Inc. (Edison, N.J.). Methods of manufacturing ethylene oxide from bio-ethanol are disclosed in, for example, PCT Publication Nos. WO 2014/125191 and 2014/125192; the entire contents of each of which are incorporated herein by reference.

For example, bio-ethanol is first converted (e.g., dehydrated) to form bio-ethylene, which in turn is converted (e.g., oxidized) to biobased ethylene oxide according to Scheme 4.

Scheme 4

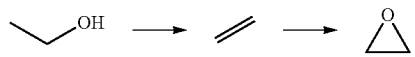

In some embodiments, bio-ethanol is converted to bio-ethylene. Methods of converting bio-ethanol to bio-ethylene are disclosed in, for example, Zhang et al. *Ind. Eng. Chem. Res.* 2013 (52), 9505-9514, the entirety of which is herein incorporated by reference. In some embodiments, bio-ethanol is dehydrated to afford bio-ethylene. In some embodiments, the step of dehydrating bio-ethanol to bio-ethylene comprises heating the reaction mixture. In some embodiments, the step of dehydrating bio-ethanol to bio-ethylene comprises a catalyst. In some embodiments, such a catalyst is selected from the group consisting of a phosphoric acid catalyst, an oxide catalyst (e.g., Alumina), a molecular sieve catalyst, and a heteropolyacid catalyst. In some embodiments, the step of dehydrating bio-ethanol to bio-ethylene comprises washing or purifying the reaction mixture.

In some embodiments, bio-ethylene is converted to bio-ethylene oxide. Methods of converting ethylene to ethylene oxide are disclosed in, for example, U.S. Pat. No. 8,975,424, and PCT Publication Nos. WO 2015/102982, 2014/186480, and 2014/105924; the entire contents of each of which are incorporated herein by reference. In some embodiments, the step of converting bio-ethylene to bio-ethylene oxide comprises $O_2$ gas. In some embodiments, the step of converting bio-ethylene to bio-ethylene oxide comprises a catalyst. In some embodiments, the step of converting bio-ethylene to bio-ethylene oxide comprises a silver catalyst that includes zinc. In some embodiments, the step of converting bio-ethylene to bio-ethylene oxide comprises a silver catalyst. In some embodiments, the step of converting bio-ethylene to bio-ethylene oxide produces $CO_2$ as a byproduct. In some embodiments, the step of converting bio-ethylene to bio-ethylene oxide comprises removing $CO_2$. In some embodiments, the step of converting bio-ethylene to bio-ethylene oxide comprises washing or purifying the reaction mixture. In some embodiments, the step of converting bio-ethylene to bio-ethylene oxide produces a glycol as a byproduct.

ii. Production of Bio-Propylene Oxide

In some embodiments, bio-ethanol or bio-glycerol is converted to bio-propylene oxide. In some embodiments, bio-ethanol or bio-glycerol is converted to bio-propylene, and bio-propylene is converted to bio-propylene oxide, according to Scheme 5.

Scheme 5

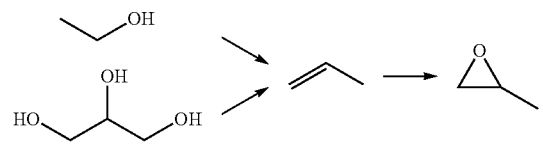

In some embodiments, bio-ethanol is converted to bio-propylene. Methods of converting bio-ethanol to bio-propylene are disclosed in, for example, European Patent Publication No. EP 2090561A1; U.S. Pat. Nos. 6,441,262, 8,598,399, 9,061,954; US Patent Publications Nos. US 2011/0105815, 2011/0137096, 2016/0186070, and PCT Publication Nos. WO 2016/061262 or 2016/109370; the entire contents of each of which are incorporated herein by reference. In some embodiments, the step of converting bio-ethanol to bio-propylene comprises a catalyst. In some embodiments, the step of converting bio-ethanol to bio-propylene comprises a catalyst selected from the group consisting of crystalline silicate (e.g., crystalline silicate having a ratio of Si/Al of at least about 100), a molecular sieve catalyst (e.g., SAPO-5, SAPO-17, SAPO-18, SAPO-20, SAPO-34, SAPO-44, or SAPO56), a rhenium oxide-modified ZSM-5 zeolite catalyst, and a Co/Mn catalyst. In some embodiments, the step of converting bio-ethanol to bio-propylene comprises water. In some embodiments, the step of converting bio-ethanol to bio-propylene comprises heating the reaction mixture.

In some embodiments, bio-glycerol is converted to bio-propylene. Methods of converting bio-glycerol to bio-propylene are disclosed in, for example. Sun et al. *Applied Catalysis B: Environmental.* 2015 (174-175), 13-30; Mota et al. *Journal of Molecular Catalysis A: Chemical.* 2016 (422) 158-164; or Wu et al. *Catalysis Communications* 2017 (92) 80-85; the entire contents of each of which are incorporated herein by reference. In some embodiments, the step of converting bio-glycerol to bio-propylene comprises a catalyst. In some embodiments, the step of converting bio-glycerol to bio-propylene comprises a catalyst selected from the group consisting of a $Cu/Al_2O_3$ catalyst (e.g., $WO_3$-loaded $Cu/Al_2O_3$, $MoO_3$-loaded $Cu/Al_2O_3$, $V_2O_5$-loaded $Cu/Al_2O_3$, or $H_3PO_4$-loaded $Cu/Al_2O_3$), an iron-molybdenum catalyst, a $MoO_3$ modified $Ni_2P/Al_2O_3$ catalyst, and a ZSM-5 catalyst. In some embodiments, the step of converting bio-glycerol to bio-propylene comprises $H_2$. In some embodiments, the step of converting bio-glycerol to bio-propylene comprises heating the reaction mixture.

In some embodiments, bio-propylene is converted to bio-propylene oxide according to methods disclosed in U.S. Pat. No. 9,174,200; Schultz et al. "Production of Propylene Oxide from Propylene Using Patented Silver Based Catalyst" (2016) *Senior Design Reports (CBE).* Paper 86. UPenn Scholarly Commons; or Schmidt et al. *Chimica Oggi—Chemistry Today* 2014 32(2), 31-35; the entire contents of each of which are incorporated herein by reference. In some embodiments, the step of converting bio-propylene to bio-propylene oxide comprises a catalyst. In some embodiments, the step of converting bio-propylene to bio-propylene oxide comprises a catalyst selected from the group consisting of a Ag—W oxide catalyst and a partly titanium substituted silica based zeolite (e.g., TS-1). In some embodiments, the step of converting bio-propylene to bio-propylene oxide comprises heating the reaction mixture. In some embodiments, the step of converting bio-propylene to bio-propylene oxide comprises $O_2$. In some embodiments, the step of converting bio-propylene to bio-propylene oxide comprises hydrogen peroxide.

C. Methods of Manufacturing Polycarbonates with Biobased and Fossil-Based Carbon In certain embodiments, provided methods comprise a step of copolymerizing carbon dioxide sequestered from a fossil carbon source with the biobased epoxide to produce a polymer composition as described above and herein (step (c)). Methods of performing epoxide-$CO_2$ copolymerization are disclosed in PCT publication WO 2010/028362, the entirety of which is incorporated herein by reference.

In certain embodiments, step (c) includes providing a polymerization system that copolymerizes carbon dioxide sequestered from a fossil carbon source with the biobased epoxide to produce a polymer composition as described above and herein. For example, in some embodiments, polymer compositions are derived from polymerization systems that copolymerize one or more epoxides with carbon dioxide in the presence of a chain transfer agents and a polymerization catalyst as shown in Scheme 6.

Scheme 6

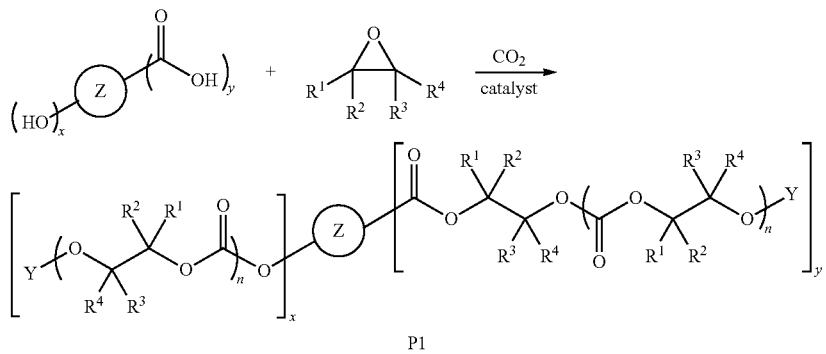

P1 i. Chain Transfer Agents

Suitable chain transfer agents include those described above with respect to

embedded within the aliphatic polycarbonate chain. In certain embodiments, suitable chain transfer agents include polyfunctional chain transfer agents as exemplified in PCT Publication No. WO 2010/028362. In certain embodiments, copolymerizations are performed as exemplified in US Patent Publication No. US 2011/0245424. In certain embodiments, copolymerizations are performed as exemplified in Cyriac et al. *Green Chem.* 2011 (13), 3469-3475.

Suitable chain transfer agents may have a broad array of chemical structures. In general, the only requirement is that each molecule of the chain transfer agent be capable of initiating two or more polycarbonate chains, this can occur by several mechanisms including: by ring-opening an epoxide monomer, by reacting with carbon dioxide molecules to yield a moiety capable of sustaining polymer chain growth, or by a combination of these. In some embodiments, a chain transfer agent may have two or more functional groups independently capable of reacting with carbon dioxide or an epoxide; examples of these include, but are not limited to molecules such as diacids, glycols, diols, triols, hydroxyacids, amino acids, amino alcohols, dithiols, mercapto alcohols, saccharides, catechols, polyethers, etc. In some embodiments, the chain transfer agent may include a multiply active functional group that is itself able to react multiple times to initiate more than one polymer chain.

Examples of the latter include, but are not limited to functional groups having a single atom capable of reacting multiple times such as ammonia, primary amines and water, as well as functional groups having more than one nucleophilic atom such as amindines, guanidines, urea, boronic acids, etc.

In some embodiments, a chain transfer agent is a polyhydric alcohol. In certain embodiments, a polyhydric alcohol is a diol, while in other embodiments the polyhydric alcohol is a triol, a tetraol or a higher polyol. In some embodiments, two hydroxyl groups are on adjacent carbons (i.e., the chain transfer agent is a glycol).

In some embodiments, two hydroxyl groups are on non-adjacent carbons. In certain embodiments, two hydroxyl groups are on the opposite ends of a chain (i.e., the chain transfer agent is an α-ω diol). In certain embodiments, such α-ω diols include $C_3$ to $C_{20}$ aliphatic chains. In certain embodiments, such α-ω diols comprise a polyether. In certain embodiments, such α-ω diols comprise a hydroxy-terminated polyolefin. In certain embodiments, such α-ω diols comprise paraformaldehyde.

In some embodiments, one —OH group of a diol is phenolic and the other is aliphatic. In other embodiments, each hydroxy group is phenolic. In certain embodiments, a chain transfer agent is an optionally substituted catechol, resorcinol or hydroquinone derivative.

In some embodiments, polyalcohol chain transfer agents encompass naturally occurring materials such as sugar alcohols, carbohydrates, saccharides, polysaccharides, starch, starch derivatives, lignins, lignans, partially hydrolyzed triglycerides, and the like, as well as known derivatives of any of these materials. In certain embodiments, a chain transfer agent is starch. In certain embodiments, a chain transfer agent is isosorbide.

In certain embodiments, a chain transfer agent is a polyamine. In some embodiments, a chain transfer agent is a diamine. In other embodiments, a chain transfer agent is a triamine, tetraamine or a higher amine oligomer.

In some embodiments, a chain transfer agent is an amino alcohol. In some embodiments, a chain transfer agent is an amino acid. In some embodiments, a chain transfer agent is an amino thiol. In some embodiments, a chain transfer agent is an amino amide.

In certain embodiments, a chain transfer agent is a diacid, a triacid or a higher polyacid. In some embodiments, a chain transfer agent is a diacid. In certain embodiments, a diacid is phthalic acid, isophthalic acid, terephthalic acid. In certain embodiments, a diacid is maleic acid, succinic acid, malonic acid, glutaric acid, adipic acid, pimelic acid, suberic acid, or azelaic acid. In some embodiments, a chain transfer agent is a triacid. In certain embodiments, a triacid is citric acid, isocitric acid, cis- or trans-aconitic acid, propane-1,2,3-tricarboxylic acid or trimesic acid.

In some embodiments, a chain transfer agent is an amino acid. In certain embodiments, amino acid chain transfer agents include the naturally occurring amino acids. In certain embodiments, amino acid chain transfer acids include peptides. In some embodiments, the peptides contain between 2 and about 20 amino acid residues. In other embodiments, the chain transfer agent is a thiol acid.

In some embodiments, the chain transfer agent is a hydroxy acid. In some embodiments, hydroxy acids are alpha-hydroxy acids. In certain embodiments an alpha hydroxy acid is selected from the group consisting of: glycolic acid, DL-lactic acid, D-lactic acid. L-lactic, citric acid and mandelic acid. In some embodiments, a hydroxy acid is a beta-hydroxy acid. In certain embodiments, a beta hydroxy acid is selected from the group consisting of: 3-hydroxypropionic acid, DL-3-hydroxybutryic acid, D-3 hydroxybutryic acid, L-3-hydroxybutyric acid, DL-3-hydroxy valeric acid, D-3-hydroxy valeric acid, L-3-hydroxy valeric acid, salicylic acid, and derivatives of salicylic acid. In some embodiments, a hydroxy acid is an α-ω hydroxy acid. In certain embodiments, α-ω hydroxy acids are selected from the group consisting of optionally substituted $C_{3-20}$ aliphatic α-ω hydroxy acids. In certain embodiments, an α-ω hydroxy acid is a polyester oligomeric ester.

In some embodiments, a chain transfer agent is provided as a carboxylate salt. In certain embodiments, a carboxylate salt is a group I or II metal salt. In some embodiments, a carboxylate salt is an ammonium salt. In certain embodiments, an ammonium cation is $NH_4$. In some embodiments, an ammonium cation is a protonated primary, secondary, or tertiary amine. In some embodiments, a salt is a quaternary ammonium salt. In some embodiments, a quaternary ammonium cation of a salt is tetramethyl, tetrabutyl, or trahexylammonium ammonium. In certain embodiments, a carboxylate salt is a phosphonium carboxylate.

In certain embodiments, a chain transfer agent is a polythiol. In some embodiments, a chain transfer agent is a dithiol. In some embodiments, a chain transfer agent is a trithiol, higher thiol oligomer.

In some embodiments, a chain transfer agent is a thio alcohol. In some embodiments, a chain transfer agent is an amino thiol. In some embodiments, a chain transfer agent is a thiol carboxylic acid.

In certain embodiments, a chain transfer agent comprises an active NH-containing functional group. In certain embodiments, a nitrogen atom of the NH-containing functional group is nucleophilic. In certain embodiments, an active NH-containing functional group is selected from the group consisting of C-linked amides, N-linked amides, O-linked carbamates N-linked carbamates, ureas, guanidines, amidines, hydrazones, and N- or C-linked thioamides.

In certain embodiments, polymerization systems of the present invention include only one chain transfer agent, while in other embodiments, mixtures of two or more chain transfer agents are used.

In certain embodiments, polymerization systems described above include a solvent in which a chain transfer agent dissolves. In certain embodiments, a chain transfer agent is poorly soluble in the epoxide, but is soluble in a mixture of epoxide and another solvent added to the reaction mixture. In certain embodiments, the solvent added to the polymerizations system is chosen from the group consisting of esters, nitriles, ketones, aromatic hydrocarbons, ethers, amines and combinations of two or more of these.

In some embodiments, a polymerization initiator includes a multiply active functional group that is itself able to react multiple times to initiate more than one polymer chain. One subset of such multiply-active functional groups react multiple times at the same atom. Examples of such groups include, but are not limited to ammonia, primary amines, hydrogen sulfide and water, all of which remain nucleophilic after the first addition and are thereby able to react again initiating additional polymer chains. Another subset of multiply active functional groups can react at different atoms in the functional group to initiate multiple chains. Examples of such groups include, but are not limited to guanidines, ureas, boronic acids, hydroxyl amines, and amidines.

In some embodiments, a chain transfer agent may contain a single multiply active functional group. In certain embodiments, a chain transfer agent may contain two or more multiply active functional groups.

In some embodiments, a chain transfer agent used in any of the methods herein is derived from biomass.

ii. Polymerization Catalysts

In some embodiments, suitable polymerization catalysts include metal complexes, e.g., transition metal complexes. Thus, in some embodiments, such metal complexes are capable of catalyzing the copolymerization of carbon dioxide and epoxides. In certain embodiments, polymerization catalysts include those disclosed in R.-R. Ang et al., *Journal of Cleaner Production.* 102 (2015) 1-17; Zhang, et al., *Chem. Rev.* 2018 (118), 839-885; Liu et al., *Current Opinion in Green and Sustainable Chemistry* 2017 (3), 61-66; or Quin, et. al., *Journal of CO2 Utilization* 2015 (11), 3-9; U.S. Pat. Nos. 7,304,172 and 6,870,004; EP Patent No. EP 2258745B1; PCT Publication Nos. WO 2010/022388, 2008/136591, 2008/150033, 2009/137540, 2010/013948, 2010/147421, 2012/037282, 2013/022932, 2013/012895, 2013/096602, 2014/031811, 2016/012785, 2016/012786, and 2010/028362; and in Chinese Patent Publication Nos. CN 2007/10010706 and 2008/10229276; the entirety of each of which is hereby incorporated herein by reference.

In some embodiments, polymerization catalysts include zinc complexes. In some embodiments, a zinc complex is a dialkylzinc complex (e.g., those described in U.S. Pat. Nos. 3,900,424 and 3,953,383; the entire contents of each of which are incorporated herein by reference). In some embodiments, a zinc complex is a diethylzinc complex. In some embodiments, a zinc complex is a zinc glutarate complex (e.g., those described in U.S. Pat. Nos. 4,783,445, 5,026,676, and 4,943,677; the entire contents of each of which are incorporated herein by reference). In some embodiments, a zinc glutarate complex is prepared from ZnO, Zn(OH)$_2$, or ZnEt$_2$. In some embodiments, a zinc glutarate complex is prepared from glutaric acid, 2-ketoglutaric acid, 2,2-dimethylglutaric acid, 3-ketoglutaric acid, 3,3-dimethylglutaric acid, 3,3-tetramethylglutaric acid, 2-methylglutaric acid, methylglutaric acid, 3-methylglutaric acid, 3,3-tetramethylglutaric acid, or 3-phenylglutaric acid.

In some embodiments, a zinc complex is an bis(phenoxy) zinc complex. For example, in some embodiments, a bis (phenoxy) zinc complex is a mononuclear (2,6-diphenylphenoxide)$_2$Zn(Et$_2$O)$_2$ complex (e.g., as described in Darensbourg, et. al., *Macromolecules* 1995, 28 (22), 7577-7579; the entire contents of which are incorporated herein by reference), or fluorosubstituted complex such as a dimeric [Zn (O-2,6-F$_2$C$_6$H$_3$)$_2$·THF]$_2$ (e.g., as described in Darensbourg, et. al., *J. Am. Chem. Soc.* 2000, 122 (50), 12487-12496; the entire contents of which are incorporated herein by reference).

In some embodiments, a zinc complex is a β-diiminate zinc complex. In some embodiments, β-diiminate zinc complexes include those described in Allen, et al. *J. Am. Chem. Soc.* 2002, 124 (48), 14284-14285, and those described in Ellis et al., *Chem. Sci.* 2104 (5), 4004-4011; the entire contents of each of which are incorporated herein by reference.

In some embodiments, polymerization catalysts include double metal cyanide (DMC) catalyst (e.g., in U.S. Pat. No. 4,500,704; the entire contents of which are incorporated herein by reference). A DMC catalyst may be prepared by the reaction between a metal salt (e.g., zinc chloride) and an alkali metal hexacyanometallate (e.g., potassium hexacyanocobaltate) in aqueous form.

In some embodiments, polymerization catalysts include racemic dinuclear Co(III) complexes. In some embodiments, racemic dinuclear Co(III) complexes include those described in Liu, et al. *Nat. Commun.* 2015 (6), 8594; the entire contents of each of which are incorporated herein by reference.

In some embodiments, polymerization catalysts include binary trivalent salen Ti complexes. In some embodiments, salen Ti complexes include those described in Wang et al. *ACS Catal.* 2015 (5), 393-396; and Wang, et al. *Catal. Sci. Technol.* 2014 (4), 3964-3972; the entire contents of each of which are incorporated herein by reference.

In some embodiments, polymerization catalysts include Al porphyrin complexes. In some embodiments, Al porphyrin complexes include those described in Wu, et al. *J. Polym. Sci. Pol. Chem.* 2014 (52), 2346-2355; Sheng, et al. *Rsc Adv.* 2014 (4), 54043-54050; and Sheng, et al. *Polym. Chem.* 2015 (6), 4719-4724; the entire contents of each of which are incorporated herein by reference.

In some embodiments, polymerization catalysts include heteronuclear Zn—Mg complexes. In some embodiments, heteronuclear Zn—Mg complexes include those described in Saini, et al. *Chem. Commun.* 2014 (50), 4164-4167; the entire contents of which are incorporated herein by reference.

In some embodiments, polymerization catalysts include bimetallic nickel complexes. In some embodiments, bimetallic nickel complexes include those described in PCT Publication No. WO 2016/012786; the entire contents of which are incorporated herein by reference.

In some embodiments, polymerization catalysts include dinuclear Zn catalysts. In some embodiments, dinuclear Zn catalysts include those described in Kissling, et al. *Chem Eurn. J.* 2015 (21), 8148-8157; the entire contents of which are incorporated herein by reference.

In some embodiments, polymerization catalysts include metal complexes denoted $L_p$-M-$(L_I)_{m'}$, where $L_p$ is a permanent ligand set, M is a metal atom, and $L_I$ is a ligand that is a polymerization initiator, and m' is an integer between 0 and 2 inclusive representing the number of initiating ligands present.

In some embodiments, a metal atom, M, is selected from periodic table groups 3-13, inclusive. In certain embodiments, M is a transition metal selected from periodic table groups 5-12, inclusive. In some embodiments, M is a transition metal selected from periodic table groups 4-11, inclusive. In certain embodiments, M is a transition metal selected from periodic table groups 5-10, inclusive. In certain embodiments. M is a transition metal selected from periodic table groups 7-9, inclusive. In some embodiments, M is selected from the group consisting of Cr, Mn, V, Fe, Co, Mo, W, Ru, Al, and Ni. In some embodiments, M is a metal atom selected from the group consisting of: cobalt; chromium; aluminum; titanium; ruthenium, and manganese. In some embodiments, M is cobalt. In some embodiments, M is chromium. In some embodiments, M is aluminum.

In certain embodiments, a metal complex is a zinc, cobalt, chromium, aluminum, titanium, ruthenium, or manganese complex. In certain embodiments, a metal complex is an aluminum complex. In other embodiments, a metal complex is a chromium complex. In yet other embodiments, a metal complex is a zinc complex. In certain other embodiments, a metal complex is a titanium complex. In still other embodiments, a metal complex is a ruthenium complex. In certain embodiments, a metal complex is a manganese complex. In certain embodiments, a metal complex is cobalt complex. In certain embodiments where a metal complex is a cobalt complex, the cobalt metal has an oxidation state of +3 (i.e., Co(III)). In other embodiments, the cobalt metal has an oxidation state of +2 (i.e., Co(II)).

In certain embodiments, a permanent ligand set comprises a single multidentate ligand that remains associated with the metal center during catalysis. In some embodiments, the permanent ligand set includes two or more ligands that remain associated with the metal center during catalysis. In some embodiments, a metal complex comprises a metal atom coordinated to a single tetradentate ligand while in other embodiments, a metal complex comprises a chelate containing a plurality of individual permanent ligands. In certain embodiments, a metal complex contains two bidentate ligands. In some embodiments, a metal complex contains a tridentate ligand.

In various embodiments, tetradentate ligands suitable for metal complexes of the present invention may include, but are not limited to: salen derivatives, derivatives of salen ligands, bis-2-hydroxybenzamido derivatives, derivatives of the Trost ligand, porphyrin derivatives, derivatives of tetrabenzoporphyrin ligands, derivatives of corrole ligands, phthalocyaninate derivatives, and dibenzotetramethyltetraaza[14]annulene (tmtaa) derivatives.

In some embodiments, polymerization systems described above further include at least one co-catalyst. In some embodiments, a co-catalyst is selected from the group consisting of: amines, guanidines, amidines, phosphines, nitrogen-containing heterocycles, ammonium salts, phosphonium salts, arsonium salts, bisphosphine ammonium salts, and a combination of any two or more of the above.

In embodiments where the co-catalyst is an 'onium' salt, there is necessarily an anion present to balance the charge of the salt. In certain embodiments, this is any anion. In certain embodiments, the anion is a nucleophile. In some embodiments, the anion is a nucleophile capable of ring-opening an epoxide. In some embodiments, the anion is selected from the group consisting of: azide, halides, alkyl sulfonates, carboxylates, alkoxides, and phenolates.

In some embodiments, ionic co-catalyst include anions selected from the group consisting of: —OR$^w$, —SR$^w$, —OC(O)R$^w$, —OC(O)OR$^w$, —OC(O)N(R$^w$)$_2$, —NR$^w$C(O)R$^w$, —CN, halo (e.g., —Br, —I, —Cl), —N$_3$, and —OSO$_2$R$^w$ wherein each R$^w$ is, independently, selected from hydrogen, optionally substituted aliphatic, optionally substituted heteroaliphatic, optionally substituted aryl and optionally substituted heteroaryl and where two R$^w$ groups can be taken together to form an optionally substituted ring optionally containing one or more additional heteroatoms.

In some embodiments, polymerization catalysts include metal complexes where a metal atom coordinated to a multidentate ligand and at least one activating moiety tethered to a multidentate ligand. In certain embodiments, such metal complexes have the structure:

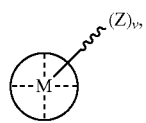

where

represents a metal atom coordinated to a multidentate ligand; and $\sim\sim\sim$(Z)$_v$ represents one or more activating moieties, where "$\sim\sim\sim$" is a covalent linker containing one or more atoms selected from the group consisting of C, O, N, S, and Si; Z is a activating functional group and m is an integer from 1 to 4 indicating the number of individual activating functional groups present in each activating moiety.

In some embodiments, a metal complex

comprises a metal atom coordinated to a single tetradentate ligand and in some embodiments, the metal complex comprises a chelate containing a plurality of individual ligands. In certain embodiments, a metal complex contains two bidentate ligands. In some embodiments, a metal complex contains a tridentate ligand.

In some embodiments, each activating functional group is independently selected from the group consisting of neutral nitrogen-containing moieties, cationic moieties, phosphorous-containing moieties, and combinations of two or more of these.

In various embodiments, tetradentate ligands suitable for metal complexes of the present invention may include, but are not limited to: salen derivatives, derivatives of salan ligands, bis-2-hydroxybenzamido derivatives, derivatives of the Trost ligand, porphyrin derivatives, derivatives of tetrabenzoporphyrin ligands, derivatives of corrole ligands, phthalocyaninate derivatives, and dibenzotetramethyltetraaza[14]annulene (tmtaa) derivatives.

In certain embodiments, a tetradentate ligand is a salen ligand. In certain embodiments, a metal complex is a metallosalenate. In certain embodiments, a metal complex is a cobalt salen complex. In certain embodiments, a metal complex is a chromium salen complex. In some embodiments, a metal complex is an aluminum salen complex.

In certain embodiments, at least one activating moiety is tethered to a carbon atom of a phenyl ring of the salicylaldehyde-derived portions of a salen ligand. In certain embodiments, at least one activating moiety is tethered to a carbon atom of a porphyrin ligand. In certain embodiments, at least one activating moiety is tethered to a pyrrole-carbon atom of a porphyrin ligand. In certain embodiments, at least one activating moiety is tethered to a carbon atom forming the bridge between the pyrrole rings of a porphyrin ligand.

In certain embodiments, at least one activating moiety is tethered to one or more carbon atoms of only one phenyl ring of the salicylaldehyde-derived portions of a salen ligand.

iii. Epoxides

Suitable epoxides include those biobased epoxides described above and herein.

In some embodiments, suitable epoxides include those having a structure:

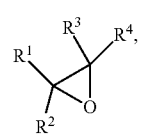

$R^1$, $R^2$, $R^3$, and $R^4$ are as described above and herein.

In certain embodiments, reaction mixtures include one or more epoxides selected from the group consisting of:

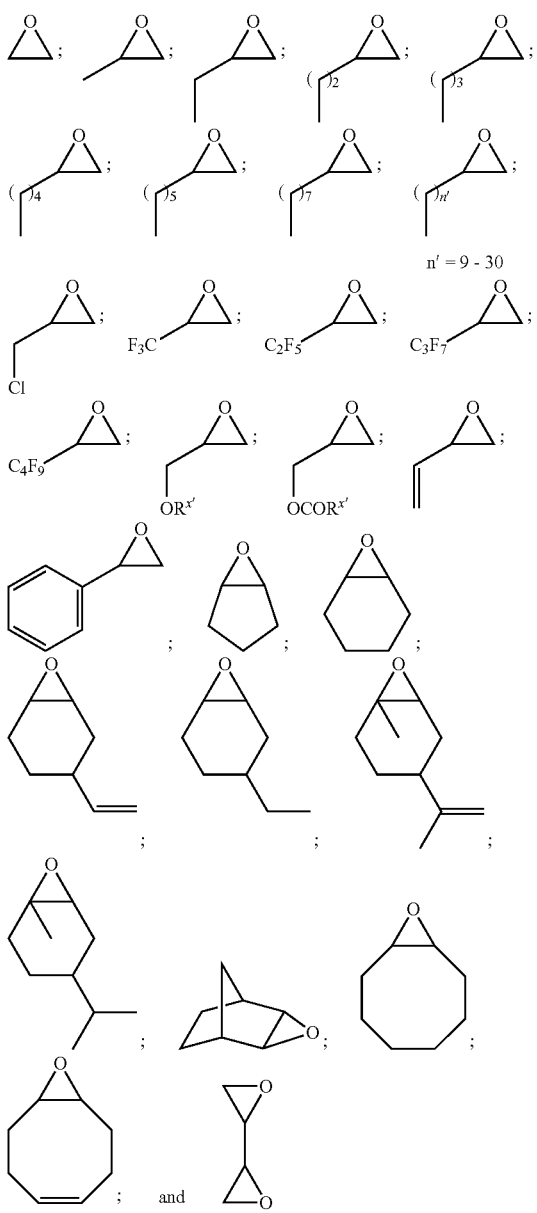

wherein each $R^{x'}$ is, independently, selected from optionally substituted aliphatic, optionally substituted heteroaliphatic, optionally substituted aryl and optionally substituted heteroaryl.

In certain embodiments, reaction mixtures include ethylene oxide. In other embodiments, reaction mixtures include propylene oxide. In other embodiments, reaction mixtures include cyclohexene oxide. In other embodiments, reaction mixtures include epichlorohydrin. In certain embodiments, reaction mixtures include a glycidyl ether or glycidyl ester. In certain embodiments, reaction mixtures include phenyl glycidyl ether. In certain embodiments, reaction mixtures include 1-butyl glycidyl ether.

In certain embodiments, reaction mixtures include ethylene oxide and propylene oxide. In certain embodiments, reaction mixtures include propylene oxide along with from about 0.1 to about 10% of a $C_4$-$C_{30}$ epoxide. In certain embodiments, reaction mixtures include propylene oxide along with from about 0.1 to about 10% of a glycidyl ether. In certain embodiments, reaction mixtures include propylene oxide along with from about 0.1 to about 10% of a glycidyl ester. In certain embodiments, reaction mixtures include ethylene oxide along with from about 0.1 to about 10% of a glycidyl ether. In certain embodiments, reaction mixtures include ethylene oxide along with from about 0.1 to about 10% of a glycidyl ester. In certain embodiments, reaction mixtures include ethylene oxide along with from about 0.1 to about 10% of a $C_4$-$C_{30}$ epoxide.

In certain embodiments, reaction mixtures include epoxides derived from naturally occurring materials such as epoxidized resins or oils. Examples of such epoxides include, but are not limited to: Epoxidized Soybean Oil; Epoxidized Linseed Oil; Epoxidized Octyl Soyate; Epoxidized PGDO; Methyl Epoxy Soyate; Butyl Epoxy Soyate; Epoxidized Octyl Soyate; Methyl Epoxy Linseedate; Butyl Epoxy Linseedate; and Octyl Epoxy Linseedate. These and similar materials are available commercially from Arkema Inc. under the trade name Vikoflex®. Examples of such commerically available Vikoflex® materials include Vikoflex 7170 Epoxidized Soybean Oil. Vikoflex 7190 Epoxidized Linseed, Vikoflex 4050 Epoxidized Octyl Soyate, Vikoflex 5075 Epoxidized PGDO, Vikoflex 7010 Methyl Epoxy Soyate, Vikoflex 7040 Butyl Epoxy Soyate, Vikoflex 7080 Epoxidized Octyl Soyate, Vikoflex 9010 Methyl Epoxy Linseedate, Vikoflex 9040 Butyl Epoxy Linseedate. and Vikoflex 9080 Octyl Epoxy Linseedate. In certain embodiments, the polycarbonate polyols of the present invention incorporate epoxidized fatty acids.

In certain embodiments of the present invention, reaction mixtures include epoxides derived from alpha olefins. Examples of such epoxides include, but are not limited to those derived from $C_{10}$ alpha olefin, $C_{12}$ alpha olefin, $C_{14}$ alpha olefin, $C_{16}$ alpha olefin, Cis alpha olefin, $C_{20}$-$C_{24}$ alpha olefin, $C_{24}$-$C_{28}$ alpha olefin and $C_{30+}$ alpha olefins. These and similar materials are commercially available from Arkema Inc. under the trade name Vikolox®. Commerically available Vikolox®® materials include those depicted in Table 2, below. In certain embodiments, reaction mixtures including alpha olefins also include other simpler epoxide monomers including, but not limited to: ethylene oxide, propylene oxide, butylene oxide, hexene oxide, cyclopentene oxide and cyclohexene oxide.

TABLE 2

| Trade Name | Formula | Minimum Oxirane |
| --- | --- | --- |
| Vikolox 10 | $C_{10}H_{20}O$ | 9.0% |
| Vikolox 12 | $C_{12}H_{24}O$ | 7.8% |
| Vikolox 14 | $C_{14}H_{28}O$ | 6.8% |
| Vikolox 16 | $C_{16}H_{32}O$ | 6.0% |
| Vikolox 18 | $C_{18}H_{36}O$ | 5.4% |
| Vikolox 20-24 | $C_{20-24}H_{40-48}O$ | 4.4% |
| Vikolox 24-28 | $C_{24-28}H_{48-56}O$ | 3.25% |
| Vikolox 30+ | $C_{30+}H_{60}O$ | 2.25% | iv. Stoichiometry of Polymerization System

Having described in detail each of the components of the polymerization system, we turn now to the relative ratios of those components. In certain embodiments, a metal complex and a chain transfer agent $Y'$-A-$(Y')_{n'}$ are present in a defined ratio selected to maximize conversion of the epoxide monomers while achieving the desired molecular weight polycarbonate polyol, where -A- is a covalent bond or a multivalent moiety and each —Y group is independently a functional group capable of initiating chain growth of epoxide $CO_2$ copolymers and each Y group may be the same or different, and n is an integer between 1 and 10 inclusive. In embodiments, where a co-catalyst is present, the ratios between a metal complex, a co-catalyst and a chain transfer agent are selected to maximize conversion of the epoxide monomers while achieving the desired molecular weight polycarbonate polyol.

In some embodiments, a metal complex and a chain transfer agent are present in a molar ratio ranging from about 1:10 to about 1:1000. In certain embodiments, the ratio is between about 1:50 and about 1:500. In certain embodiments, the ratio is between about 1:100 and about 1:500). In certain embodiments, the ratio is between about 1:100 and about 1:1000. In certain embodiments, the ratio is between about 1:500 and about 1:1000. In certain embodiments, the ratio is between about 1:50 and about 1:250. In certain embodiments, the ratio is between about 1:20 and about 1:100. In certain embodiments, the ratio is between about 1:100 and about 1:250. In some embodiments, a metal complex and a chain transfer agent are present in a molar ratio greater than 1:1000. In some embodiments, a metal complex and a chain transfer agent are present in a molar ratio less than 1:1000.

In some embodiments, a metal complex and a chain transfer agent are present in a molar ratio greater than 1:100. In some embodiments, a metal complex and a chain transfer agent are present in a molar ratio greater than 1:250. In some embodiments, a metal complex and a chain transfer agent are present in a molar ratio greater than 1:500. In some embodiments, a metal complex and a chain transfer agent are present in a molar ratio greater than 1:1250. In some embodiments, a metal complex and a chain transfer agent are present in a molar ratio greater than 1:1500. In some embodiments, a metal complex and a chain transfer agent are present in a molar ratio greater than 1:1750. In some embodiments, a metal complex and a chain transfer agent are present in a molar ratio greater than 1:2000.

In some embodiments, a metal complex and a chain transfer agent are present in a molar ratio ranging from about 1:1000 to about 1:2000. In some embodiments, a metal complex and a chain transfer agent are present in a molar ratio ranging from about 1:1000 to about 1:1750. In some embodiments, a metal complex and a chain transfer agent are present in a molar ratio ranging from about 1:1000 to about 1:1500. In some embodiments, a metal complex and a chain transfer agent are present in a molar ratio ranging from about 1:1000 to about 1:1300. In some embodiments, a metal complex and a chain transfer agent are present in a molar ratio ranging from about 1:1100 to about 1:1300. In some embodiments, a metal complex and a chain transfer agent are present in a molar ratio ranging from about 1:1500 to about 1:200). In some embodiments, a metal complex and a chain transfer agent are present in a molar ratio ranging from about 1:1750 to about 1:2000. In some embodiments, a metal complex and a chain transfer agent are present in a molar ratio ranging from about 1:1250 to about 1:1500. In some embodiments, a metal complex and a chain transfer agent are present in a molar ratio ranging from about 1:1250 to about 1:1750.

In some embodiments, a metal complex and a co-catalyst are present in a molar ratio ranging from about 0.1:1 to about 1:10. In certain embodiments, the ratio is from about 0.5:1 to about 5:1. In other embodiments, the ratio is from about 1:1 to about 4:1. In certain embodiments, the ratio between the metal complex and the co-catalyst is about 1:1. In other embodiments, the molar ratio between a metal complex and a co-catalyst is about 1:2.

v. Reaction Conditions.

In certain embodiments, step (c) further comprises one or more solvents. In certain other embodiments, step (c) is performed in neat epoxide without the addition of solvent.

In certain methods, where a polymerization solvent is present, the solvent is an organic solvent. In certain embodiments, the solvent is a hydrocarbon. In certain embodiments, the solvent is an aromatic hydrocarbon. In certain embodiments, the solvent is an aliphatic hydrocarbon. In certain embodiments, the solvent is a halogenated hydrocarbon.

In certain embodiments, the solvent is an ether. In certain embodiments, the solvent is an ester. In certain embodiments, the solvent is a ketone.

In certain embodiments suitable solvents include, but are not limited to: Methylene Chloride, Chloroform, 1,2-Dichloroethane, Propylene Carbonate, Acetonitrile, Dimethylformamide, N-Methyl-2-pyrrolidone, Dimethyl Sulfoxide. Nitromethane, Caprolactone, 1,4-Dioxane, and 1,3-Dioxane.

In certain other embodiments, suitable solvents include, but are not limited to: Methyl Acetate, Ethyl Acetate, Acetone, Methyl Ethyl Ketone, Propylene Oxide, Tetrahydrofuran. Monoglyme Triglyme, Propionitrile, 1-Nitropropane, Cyclohexanone.

In certain embodiments, any of the above methods comprise aliphatic oxide present in amounts between about 0.5 M to about 20 M or the neat concentration of the aliphatic oxide. In certain embodiments, aliphatic oxide is present in amounts between about 0.5 M to about 2 M. In certain embodiments, aliphatic oxide is present in amounts between about 2 M to about 5 M. In certain embodiments, aliphatic oxide is present in amounts between about 5 M to about 20 M. In certain embodiments, aliphatic oxide is present in an amount of about 20 M. In certain embodiments, liquid aliphatic oxide comprises the reaction solvent.

In certain embodiments, $CO_2$ is present at a pressure of between about 30 psi to about 800 psi. In certain embodiments, $CO_2$ is present at a pressure of between about 30 psi to about 500 psi. In certain embodiments, $CO_2$ is present at a pressure of between about 30 psi to about 400 psi. In certain embodiments, $CO_2$ is present at a pressure of between about 30 psi to about 300 psi. In certain embodiments, $CO_2$ is present at a pressure of between about 30 psi to about 200 psi. In certain embodiments, $CO_2$ is present at a pressure of between about 30 psi to about 100 psi. In certain embodiments, $CO_2$ is present at a pressure of between about 30 psi to about 80 psi. In certain embodiments, $CO_2$ is present at a pressure of about 30 psi. In certain embodiments, $CO_2$ is present at a pressure of about 50 psi. In certain embodiments, $CO_2$ is present at a pressure of about 100 psi. In certain embodiments, the $CO_2$ is supercritical.

In certain embodiments of the above methods, the reaction is conducted at a temperature of between about 0° C. to about 150° C. In certain embodiments, the reaction is conducted at a temperature of between about 23° C. to about 100° C. In certain embodiments, the reaction is conducted at a temperature of between about 23° C., and about 80° C. In certain embodiments, the reaction to be conducted at a temperature of between about 23° C. to about 50° C.

In certain embodiments, a polymerization step of any of the above methods produces cyclic carbonate as a by-product in amounts of less than about 20%. In certain embodiments, cyclic carbonate is produced as a by-product in amounts of less than about 15%. In certain embodiments, cyclic carbonate is produced as a by-product in amounts of less than about 10%. In certain embodiments, cyclic carbonate is produced as a by-product in amounts of less than about 5%. In certain embodiments, cyclic carbonate is produced as a by-product in amounts of less than about 1%. In certain embodiments, the reaction does not produce any detectable by-products (e.g., as detectable by $^1$H-NMR and/or liquid chromatography (LC)).

In certain embodiments, a polymerization time is between about 30 minutes and about 48 hours. In some embodiments, the reaction is allowed to process for less than 24 hours. In some embodiments, the reaction is allowed to progress for less than 12 hours. In some embodiments, the reaction is allowed to proceed for between about 4 and about 12 hours.

In certain embodiments, a polymerization reaction is allowed to proceed until the number average molecular weight of the polymers formed is between about 500 and about 400,000 g/mol. In certain embodiments, the number average molecular weight is allowed to reach a value between 500 and 40,000 g/mol. In other embodiments, the number average molecular weight is allowed to reach a value between 500 and 20,000 g/mol. In certain embodiments, the number average molecular weight is allowed to reach a value between 500 and 10,000 g/mol. In other embodiments, the number average molecular weight is allowed to reach a value between 500 and 5,000 g/mol. In other embodiments, the number average molecular weight is allowed to reach a value between 500 and 2,500 g/mol. In other embodiments, the number average molecular weight is allowed to reach a value between 1,000 and 5,000 g/mol.

In certain embodiments, provided methods further include the step of sampling the reaction and determining the molecular weight of the polymer at a given time. In certain embodiments, this sampling and molecular weight determination are performed at two or more time intervals. In certain embodiments a plot of molecular weight gain over time is constructed and the method further includes the step of determining from this plot the time at which a desired molecular weight polymer will be present. In certain embodiments, the time at which the polymerization is ended is determined by this method.

In certain embodiments, a polymerization reaction proceeds until between about 20% and about 100% of the provided epoxide is consumed. In certain embodiments, the conversion is between about 40% and about 90%. In certain embodiments, the conversion is at least 50%. In other embodiments, the conversion is at least 60%, at least 80% or at least 85%. In certain embodiments, at least 80% of the provided epoxide is converted to polymer.

In certain embodiments, a method further includes the step of choosing the ratios at which the catalyst, the chain transfer agent and the epoxide substrate are provided. In certain embodiments, these ratios are selected to provide high epoxide conversion while providing polyol of the desired molecular weight in a selected length of time. In some embodiments, this selection of ratios includes the substeps of: i) selecting a desired length of time for which the reaction is to be run, ii) multiplying the selected length of time for which the polymerization reaction is to run by the turnover frequency of the catalyst under the reaction conditions iii) multiplying this result by the desired mol % conversion of epoxide, and iv) using the inverse of this result as the ratio of catalyst to epoxide used for the reaction. In some embodiments, the ratio of chain transfer agent to catalyst is determined by the additional following steps; v) taking the value from step (iii) above and multiplying this result by the molecular weight of the repeating unit of the polycarbonate; vi) selecting a desired molecular weight for the polyol and dividing the result from step (v) by this number; and vii) subtracting the number of chains produced per catalyst molecule from the result of step (vi) and taking the result as the ratio of chain transfer agent to catalyst used in step (1).

To make the steps of the above-described method clear, the following example is provided: in a copolymerization of propylene oxide and $CO_2$ using a catalyst that has a TOF of 1000 $h^{-1}$ and which produces two polymer chains per catalyst molecule, a polymer with Mn of 2,000 g/mol is to be produced and it is desired that 80% of the provided epoxide is converted during a reaction time of 10 hours, one would perform the following steps to obtain the required ratios:

First, taking 10 hours as the selected time interval and performing step (ii) of multiplying the selected interval of 10 hours, by the TOF of 1000 $hr^{-1}$ gives 10,000 turnovers per catalyst molecule; next multiplying this number by the desired 80% conversion (step (iii)) and then inverting (step (iv)) provides a value of $1.25 \times 10^{-4}$ corresponding to a catalyst to epoxide ratio of 1:8,000.

Moving next to determination of the chain transfer agent loading, at step (iv) one multiplies the result of step (iii) by the molecular weight of the repeating unit of the polycarbonate (in this case $C_4H_6O_3$=102 g/mol) and dividing by the desired Mn of 2,000 to give a value of 408. Subtracting the two chains per catalyst from this result in a chain transfer to catalyst ratio of 406:1. Therefore, for this example the molar ratio of catalyst to epoxide to chain transfer agent should be approximately 1:8,000:406.

It will be appreciated that the method described above is simplified in certain respects. For example, the calculation described assumes that the reaction rate is linear throughout the duration of the polymerization. The calculation described also dismisses the contribution that the mass of the chain initiator adds to the molecular weight of the polymer chains. In certain embodiments, particularly those where a polymeric chain transfer agent such as a polyether is used, or where a very low molecular weight oligomer is produced, the contribution of the mass of the initiator to the Mn of the polymer may be significant. It will be understood by those skilled in the art that additional chain transfer agent can be added to account for this effect, and more specifically, that the calculations described above can be modified to account for this effect. Similarly, more detailed kinetic data could be used to account for changes in the reaction rate over time as the reaction proceeds. For instances where a mixture of epoxides is present, the molecular weight of the repeating unit may be approximated by using a weighted average of the molecular weights of the epoxides present in the mixture. This could be further refined by analyzing copolymer made under similar conditions to determine the mole percent incorporation of the different monomers (for example by using NMR spectroscopy) since all epoxides may not be incorporated into polymer with equal efficiency. These and other modifications will be readily apprehended by the skilled artisan and are specifically encompassed by the methods provided herein.

In certain embodiments, it has been found that the turnover frequency of some catalysts decreases as the ratio of chain transfer agent to catalyst increases. This effect can be particularly noticeable at ratios higher than about 100:1. In these instances, the above-described methods may not produce the expected Mn and monomer conversion in a given time interval. In such cases it may be necessary to measure the TOF of the catalyst at various chain transfer agent ratios prior to performing the calculations described above. In general, such cases require the reaction interval be lengthened by an amount proportional to the falloff in catalyst activity at the catalyst to chain transfer agent ratio used, or in some embodiments the catalyst loading be increased by a compensatory amount.

As noted above, water present in the reaction mixtures of the described methods can also act as a chain transfer agent. In certain embodiments, the calculations described above further include the method of measuring the water content of the reaction (preferably after the reaction vessel has been charged with epoxide, chain transfer agent and any solvent to be used, but prior to addition of the catalyst). The molar equivalents of water relative to catalyst are then calculated and the ratio of chain transfer agent to catalyst can be decreased accordingly. If this is not done and there is significant water present, the Mn will be lower than expected at a given % conversion.

III. Methods of Determining Relative Amount of Biobased Carbon Present in Polycarbonates In one aspect, the present invention provides methods of determining the provenance of particular carbon atoms comprising the polymer compositions described above and herein.

In some embodiments, the present invention provides methods comprising the steps of:

a) treating a polymer composition described above and herein to liberate a cyclic carbonate of formula:

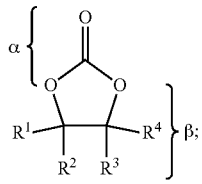

wherein $R^1$, $R^2$, $R^3$, and $R^4$ are as described above and herein;

b) treating the cyclic carbonate to liberate carbon atoms labeled α as $CO_2$, and carbon atoms labeled β as an epoxide of formula:

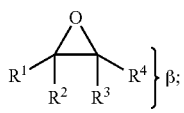

wherein $R^1$, $R^2$, $R^1$, and $R^4$ are as described above and herein; and c) measuring the radiocarbon content of the $CO_2$ comprising carbon atoms labeled α, and the epoxide comprising carbon atoms labeled β.

In some embodiments, the present invention provides methods comprising the steps of:

a) treating a polymer composition described above and herein to liberate a cyclic carbonate of formula:

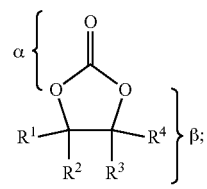

wherein $R^1$, $R^2$, $R^3$, and $R^4$ are as described above and herein;

b) treating the cyclic carbonate to liberate carbon atoms labeled α as $CO_2$, and carbon atoms labeled β as an epoxide of formula:

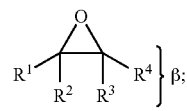

wherein $R^1$, $R^2$, $R^3$, and $R^4$ are as described above and herein;

c) separating the $CO_2$ from the epoxide; and d) measuring the radiocarbon content of the $CO_2$ comprising carbon atoms labeled α, and the epoxide comprising carbon atoms labeled β.

A. Treating a Polymer Composition to Liberate Cyclic Carbonate

In some embodiments, a liberated cyclic carbonate of step (a) corresponds to linkages within polycarbonate chains within a polymer composition. For example, in some embodiments, treating poly(ethylene carbonate) chains liberates a cyclic carbonate having a structure

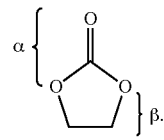

In some embodiments, treating poly(propylene carbonate) chains liberates a cyclic carbonate having a structure:

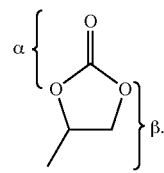

In some embodiments, the step of treating polycarbonate chains to liberate a cyclic carbonate comprises a base. In some embodiments, the step of treating polycarbonate chains to liberate a cyclic carbonate comprises a strong base.

In some embodiments, a liberated cyclic carbonate corresponds to an epoxide used in the copolymerization of polycarbonate chains within a polymer composition.

B. Treating Cyclic Carbonate to Liberate $CO_2$ and an Epoxide

In some embodiments, treating the cyclic carbonate to liberate carbon atoms labeled α as $CO_2$, and carbon atoms labeled β as an epoxide. In some embodiments, a liberated epoxide of step (b) corresponds to the cyclic carbonate of step (a). For example, in some embodiments, treating a cyclic carbonate of formula:

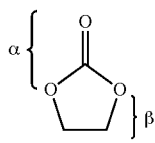

liberates carbon atoms labeled α as CO₂, and carbon atoms labeled β as an epoxide of formula:

In some embodiments, treating a cyclic carbonate of formula:

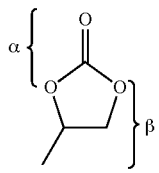

liberates carbon atoms labeled α as CO₂, and carbon atoms labeled β as an epoxide of formula:

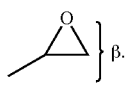

In some embodiments, reaction conditions for treating cyclic carbonate to liberate CO₂ and an epoxide are disclosed in U.S. Pat. No. 4,069,234, the entirety of which is incorporated herein by reference. In some embodiments, the step of treating cyclic carbonate to liberate CO₂ and an epoxide comprises heating to an elevated temperature. In some embodiments, the step of treating cyclic carbonate to liberate CO₂ and an epoxide comprises heating to a temperature between about 25° C., and about 300° C. In some embodiments, the step of treating cyclic carbonate to liberate CO₂ and an epoxide comprises heating to a temperature between about 100° C., and about 250° C. In some embodiments, the step of treating cyclic carbonate to liberate CO₂ and an epoxide comprises holding the reaction at the elevated temperature for between about 0.5 hrs and about 24 hrs. In some embodiments, the step of treating cyclic carbonate to liberate CO₂ and an epoxide comprises holding the reaction at the elevated temperature for between about 1.5 hrs and about 5 hrs.

C. Separating the Epoxide and the CO₂

The epoxide and the CO₂ can be separated according to means well known in the art. Suitable means of separation include condensing the epoxide from a gaseous mixture leaving the CO₂ in the gas phase or chromatographic means such as gas chromatography or gas/liquid chromatography. The separation can also be performed as part of the analysis for example, by separation based on their mass/charge ratio in a mass spectrometer. In certain embodiments, the step of separating may comprise an integral part of the Radiocarbon Content measurement—as for example where gas chromatography or mass spectrometry are part of the measurement process.

D. Measuring the Radiocarbon Content

In some embodiments, radiocarbon content is measured by methods known in the art. In some embodiments, radiocarbon content is measured according to Method B disclosed in ASTM D6866-16.

E. Additional Steps

In some embodiments, methods described above and herein further comprise the step of using the measured radiocarbon content to confirm that the carbon atoms at the positions labeled α are derived from a fossil carbon source by having a pMC of less than about 1, less than about 0.1, or less than about 0.03.

In some embodiments, methods described above and herein further comprise the step of measuring the radiocarbon content of any CTA that comprises part of the polycarbonate chains. In certain embodiments, the CTA is liberated from the polymer chain during the step of treating the polymer composition to liberate cyclic carbonate. During or after this step, the CTA (or one or more molecules arising from the CTA) can be isolated and the pMC and % biobased carbon of the CTA or its residues can be measured, e.g., according to ASTM D6866-16 (Method B). These data combined with the biocontent of the other polymer constituents permits determination of the overall % biobased carbon of the polymer composition.

In some embodiments, methods described above and herein further comprise the step of using the measured radiocarbon content to confirm that the carbon atoms at the positions labeled β are derived from a biobased feedstock by having a pMC of at least about 95, at least about 99, or at least about 100.

EXAMPLES

Example 1

This example demonstrates a method of the present invention with a chain transfer agent and a catalyst $L_p$-M-$(L_I)_m$ utilizing a co-catalyst PPN+Cl—, where the chain transfer agent is 1,4-cyclohexanedimethanol;

-$L_p$ is a salcy ligand

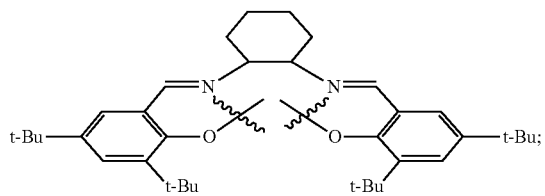 [SMILES: *Oc1c(/C=N/C2CCCCC2/N=C/c2cc(C(C)(C)C)cc(C(C)(C)C)c2O*)cc(C(C)(C)C)cc1C(C)(C)C]

-M- is Co(III); and

-$L_I$ is

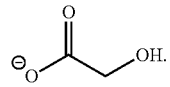

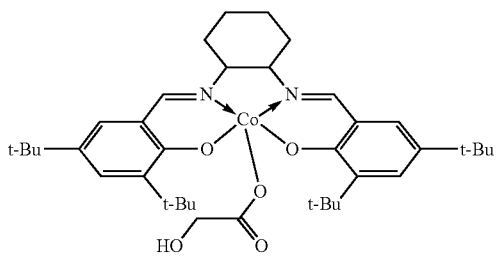

E-1

24 mg of catalyst E1 (0.04 mmol), 0.45 g (3.1 mmol) 1,4-cyclohexanedimethanol and 20 mg (0.04 mmol) PPN$^+$Cl$^-$ are held under vacuum in a Fisher-Potter bottle. The bottle is filled with nitrogen and 20 ml of biobased propylene oxide is added. The bottle is pressurized with 100 psi CO$_2$ that is derived from the combustion of fossil fuel. After 41 h at 30° C. the bottle is opened and the polymer is isolated by pouring into methanol.

The polycarbonate polyol composition thus obtained consists predominantly of polymer chains having the formula:

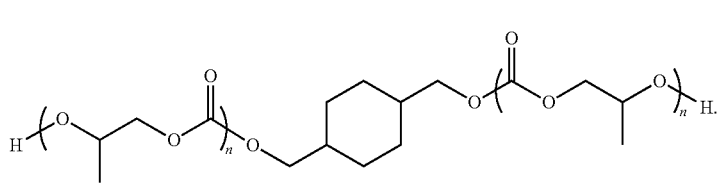

P-1

Example 2

This example demonstrates a method of the present invention with a chain transfer agent and a catalyst L$_p$-M-(L$_I$)$_m$ utilizing a co-catalyst PPN+Cl—, where the chain transfer agent is propoxylated pentaerythritol;

-L$_p$ is a salcy ligand

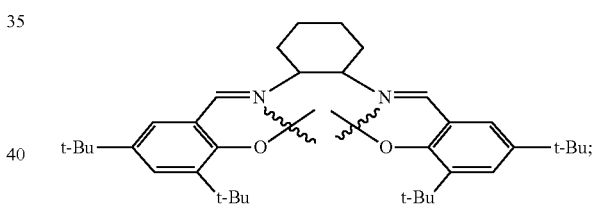

-M- is Co(III); and

-L$_I$ is trifluoroacetate.

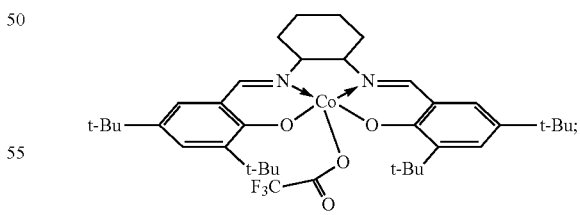

E-2

51 mg of catalyst E2 (0.07 mmol), 0.5 g (1.4 mmol) of propoxylated pentaerythritol and 41 mg (0.08 mmol), PPN$^+$Cl$^-$ are held under vacuum in a Fisher-Potter bottle. The bottle is filled with nitrogen and 20 ml of biobased propylene oxide is added. The bottle is pressurized with 100 psi CO$_2$ that is derived from the combustion of fossil fuel. After 22 h at 30° C. the bottle is opened and the polymer is isolated by pouring into methanol.-

The polycarbonate polyol composition thus obtained consists predominantly of polymer chains having a formula:

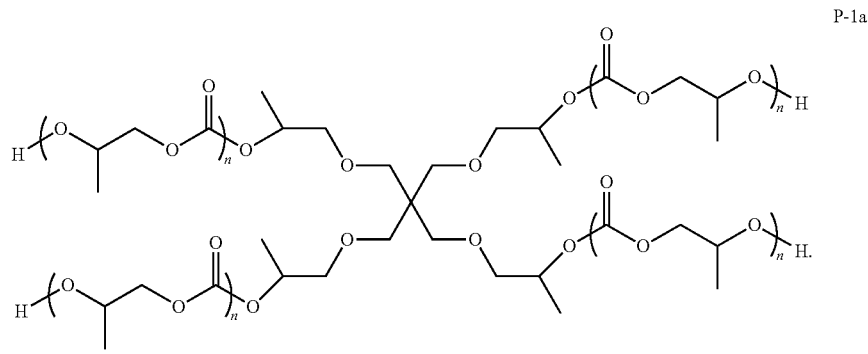

P-1a

Example 3

Example 3 was conducted using conditions similar to Example 2, except Poly(caprolactone) diol having an Mn of 530 g/mol is used as the chain transfer agent.

Example 4

Example 4 was conducted using conditions similar to Example 2, except Poly(ethylene glycol) having an Mn of 400 g/mol is used as the chain transfer agent.

Example 5

Example 5 was conducted using conditions similar to Example 2, except Poly(propylene glycol) having an Mn of 760 g/mol is used as the chain transfer agent.

Example 6

Example 6 was conducted using conditions similar to Example 2, except 1,2-cyclohexane diol is used as the chain transfer agent.

Example 7

This example demonstrates a method of the present invention with a chain transfer agent and a catalyst $L_p$-M-$(L_I)_m$ utilizing a co-catalyst PPN+Cl—, where the chain transfer agent is 1,4 butane diol;

-$L_p$ is a salcy ligand

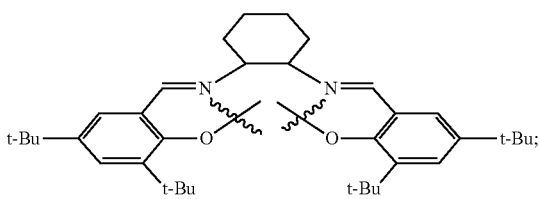 [SMILES: *Oc1c(/C=N/C2CCCCC2/N=C/c2cc(C(C)(C)C)cc(C(C)(C)C)c2O*)cc(C(C)(C)C)cc1C(C)(C)C]

-M- is Co(III); and

-$L_I$ is trifluoroacetate.

An oven dried glass vessel is charged with 11.5 mg of catalyst E2 (0.016 mmol) and 9.2 mg of PPN+Cl— (0.016 mmol). The vessel is purged with nitrogen and 1.4 butane diol (0.073 g, 0.8 mmol) is added as a solution in dry THF (0.5 mL). Biobased propylene oxide (4.5 mL, 64 mmol) is then added. The reaction vessel is pressurized with 300 psig dry carbon dioxide gas that is derived from the combustion of fossil fuel and stirred at 30° C. for 3 hours. The reaction is quenched with acid, diluted with 25 mL acetone and concentrated to afford crude polymer.

The polycarbonate polyol composition thus obtained consists predominantly of polymer chains having a formula:

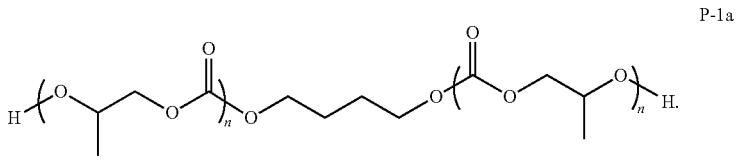

P-1a

Example 8

This example demonstrates a method of the present invention with a chain transfer agent and a catalyst $L_p$-M-$(L_I)_m$ utilizing a co-catalyst PPN+Cl—, where the chain transfer agent is 1,3 propane diol;

-$L_p$ is a salcy ligand

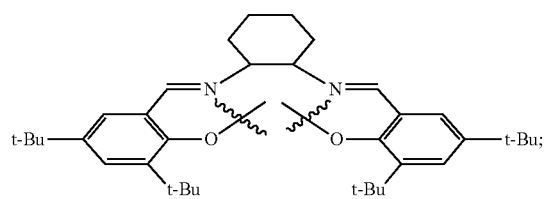 [SMILES: *Oc1c(/C=N/C2CCCCC2/N=C/c2cc(C(C)(C)C)cc(C(C)(C)C)c2O*)cc(C(C)(C)C)cc1C(C)(C)C]

-M- is Co(III); and
-$L_I$ is trifluoroacetate.

An oven dried glass vessel is charged with 11.5 mg of catalyst E2 (0.016 mmol) and 9.2 mg of PPN$^+$Cl$^-$ (0.016 mmol). The vessel is purged with nitrogen and 1,4 propane diol (0.061 g, 0.8 mmol) is added as a solution in dry THF (0.5 mL). Biobased propylene oxide (4.5 mL, 64 mmol) is then added. The reaction vessel is pressurized with 300 psig dry carbon dioxide gas that is derived from the combustion of fossil fuel and stirred at 30° C. for 3× hours. The reaction is quenched with acid, diluted with 25 mL acetone and concentrated to afford crude polymer.

The polycarbonate polyol composition thus obtained consists predominantly of polymer chains having a formula:

P-1a

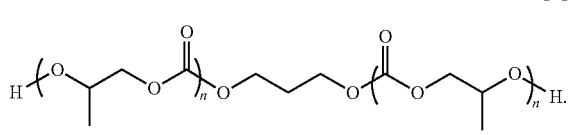

Example 9

This example demonstrates a method of the present invention with a chain transfer agent and a catalyst $L_p$-M-$(L_I)_m$ utilizing a co-catalyst PPN+Cl—, where the chain transfer agent is 1,4 butene diol;

-$L_p$ is a salcy ligand

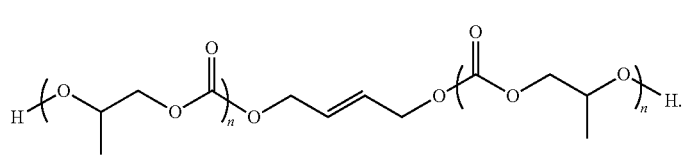

-M- is Co(III); and
-$L_I$ is trifluoroacetate.

An oven dried glass vessel is charged with 11.5 mg of catalyst E2 (0.016 mmol) and 9.2 mg of PPN+Cl— (0.016 mmol). The vessel is purged with nitrogen and 1,4 butene diol (0.079 g, 0.8 mmol) is added as a solution in dry THF (0.5 mL). Biobased propylene oxide (4.5 mL, 64 mmol) is then added. The reaction vessel is pressurized with 300 psig dry carbon dioxide gas that is derived from the combustion of fossil fuel and stirred at 30° C. for 3 hours. The reaction is quenched with acid, diluted with 25 mL acetone and concentrated to yield 1.5 g of crude polymer.

The polycarbonate polyol composition thus obtained consists predominantly of polymer chains having a formula:

P-1a

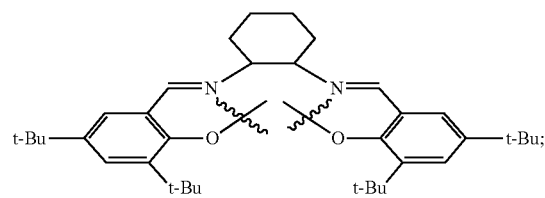 [SMILES: *Oc1c(/C=N/C2CCCCC2/N=C/c2cc(C(C)(C)C)cc(C(C)(C)C)c2O*)cc(C(C)(C)C)cc1C(C)(C)C]

Example 10

This example demonstrates a method of the present invention with a chain transfer agent and a catalyst $L_p$-M-$(L_I)_m$ utilizing a co-catalyst PPN+Cl—, where the chain transfer agent is succinic acid;

-$L_p$ is a salcy ligand

-M- is Co(III); and
-$L_I$ is trifluoroacetate.

An oven dried glass vessel is charged with 11.5 mg of catalyst E2 (0.016 mmol); 9.2 mg of PPN+Cl− (0.016 mmol); succinic acid (0.095 g, 0.8 mmol) and 0.5 mL THF. Biobased propylene oxide (4.5 mL, 64 mmol) is then added. The reaction vessel is pressurized with 300 psig dry carbon dioxide gas that is derived from the combustion of fossil fuel and stirred at 30° C. for 3 hours. The reaction is quenched with acid, diluted with 25 mL acetone and concentrated to afford the crude polymer.

The polycarbonate polyol composition thus obtained consists predominantly of polymer chains having a formula:

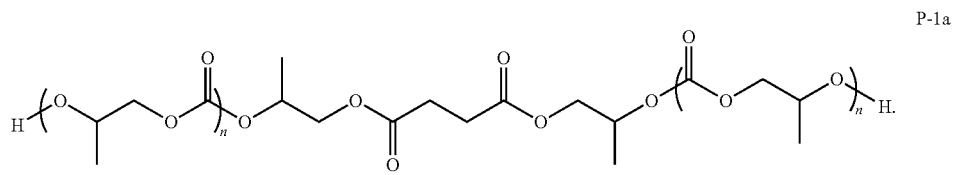

P-1a

Example 11

This example demonstrates a method of the present invention with a chain transfer agent Y-A-(Y)$_n$ and a catalyst L$_p$-M-(L$_I$)$_m$ utilizing a co-catalyst PPN+Cl—, where
the chain transfer agent is adipic acid;
-L$_p$ is a salcy ligand

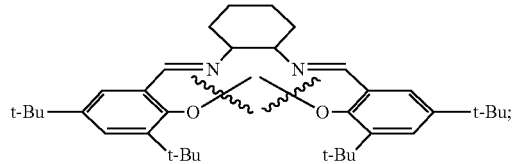 [SMILES: *Oc1c(/C=N/C2CCCCC2/N=C/c2cc(C(C)(C)C)cc(C(C)(C)C)c2O*)cc(C(C)(C)C)cc1C(C)(C)C]

-M- is Co(III); and
-L$_I$ is trifluoroacetate.

An oven dried glass vessel is charged with 11.5 mg of catalyst E2 (0.016 mmol); 9.2 mg of PPN+Cl− (0.016 mmol); adipic acid (0.12 g, 0.8 mmol) and 0.5 mL THF. Biobased propylene oxide (4.5 mL, 64 mmol) is then added. The reaction vessel is pressurized with 300 psig dry carbon dioxide gas that is derived from the combustion of fossil fuel and stirred at 30° C. for 3 hours. The reaction is quenched with acid, diluted with 25 mL acetone and concentrated to afford the crude polymer.

The polycarbonate polyol composition thus obtained consists predominantly of polymer chains having a formula:

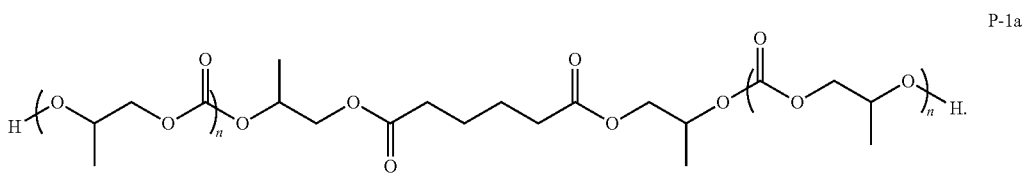

P-1a

Example 12

This example demonstrates a method of the present invention with a diacid chain transfer agent and a catalyst $L_p$-M-$(L_I)_m$ utilizing a co-catalyst PPN+Cl—, where
the chain transfer agent is maleic acid;
-$L_p$ is a salcy ligand

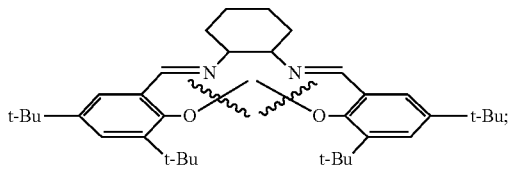 [SMILES: *Oc1c(/C=N/C2CCCCC2/N=C/c2cc(C(C)(C)C)cc(C(C)(C)C)c2O*)cc(C(C)(C)C)cc1C(C)(C)C]

-M- is Co(III); and
-$L_I$ is trifluoroacetate.

An oven dried glass vessel is charged with 11.5 mg of catalyst E2 (0.016 mmol); 9.2 mg of PPN$^+$Cl$^-$ (0.016 mmol); maleic acid (0.095 g, 0.8 mmol) and 0.5 mL THF. Biobased propylene oxide (4.5 mL, 64 mmol) is then added. The reaction vessel is pressurized with 300 psig dry carbon dioxide gas that is derived from the combustion of fossil fuel and stirred at 30° C. for 3 hours. The reaction is quenched with acid, diluted with 25 mL acetone and concentrated to afford the crude polymer.

The polycarbonate polyol composition thus obtained consists predominantly of polymer chains having a formula:

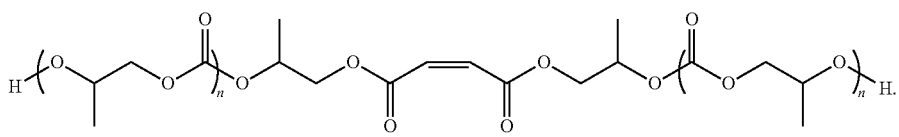

Example 13

This example demonstrates a method of the present invention with a biobased chain transfer agent and a catalyst $L_p$-M-$(L_I)_m$ utilizing a co-catalyst PPN+Cl—, where
the chain transfer agent is biobased isosorbide;
-$L_p$ is a salcy ligand

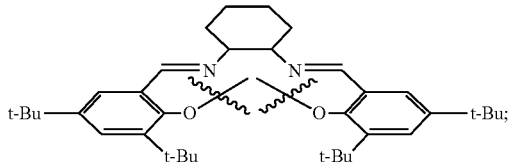 [SMILES: *Oc1c(/C=N/C2CCCCC2/N=C/c2cc(C(C)(C)C)cc(C(C)(C)C)c2O*)cc(C(C)(C)C)cc1C(C)(C)C]

-M- is Co(III); and
-$L_I$ is trifluoroacetate.

An oven dried glass vessel is charged with 11.5 mg of catalyst E2 (0.016 mmol) and 9.2 mg of PPN$^+$Cl$^-$ (0.016 mmol). The vessel is purged with nitrogen and isosorbide (0.12 g, 0.8 mmol) is added as a solution in dry THF (0.5 mL). Biobased propylene oxide (4.5 mL, 64 mmol) is then added. The reaction vessel is pressurized with 300 psig dry carbon dioxide gas that is derived from the combustion of fossil fuel and stirred at 30° C. for 3 hours. The reaction is quenched with acid, diluted with 25 mL acetone and concentrated to afford the crude polymer.

The polycarbonate polyol composition thus obtained consists predominantly of polymer chains having a formula:

P-1a

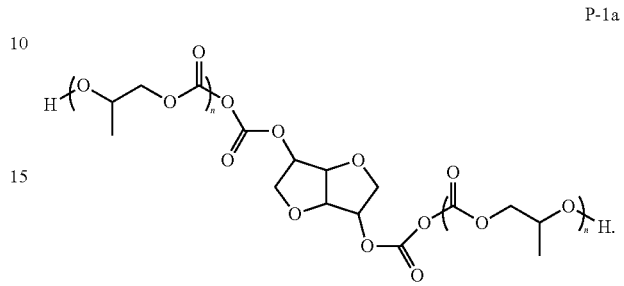

Example 14

This example demonstrates a method of the present invention with a chain transfer agent and a catalyst $L_p$-M-$(L_I)_m$ utilizing a co-catalyst PPN+Cl—, where
the chain transfer agent is paraformaldehyde with the avg. MW is 600 g/mol;
-$L_p$ is a salcy ligand -M- is Co(III); and
-$L_I$ is trifluoroacetate.

An oven dried glass vessel is charged with 11.5 mg of catalyst E2 (0.016 mmol); 9.2 mg of PPN$^+$Cl$^-$ (0.016 mmol); paraformaldehyde (24 mg, 0.04 mmol); and dry THF (0.5 mL). Biobased propylene oxide (4.5 mL, 64 mmol) is then added. The reaction vessel is pressurized with 300 psig dry carbon dioxide gas that is derived from the combustion of fossil fuel and stirred at 30° C. for 3 hours. The reaction is quenched with acid, diluted with 25 mL acetone and concentrated to afford the crude polymer.

The polycarbonate polyol composition thus obtained consists predominantly of polymer chains having a formula:

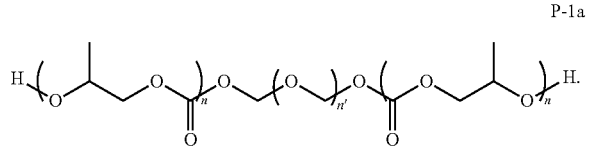

P-1a

Example 15

This example demonstrates a method of the present invention with a chain transfer agent and a catalyst $L_p$-M-$(L_I)_m$, where, the chain transfer agent is dipropylene glycol:
-$L_p$ is

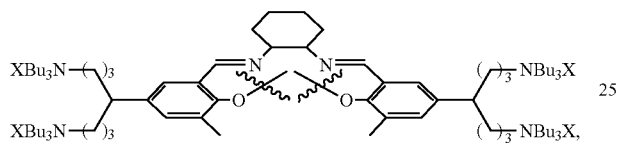

where each X is trifluoroacetate:
-M- is Co(III); and
-$L_I$ is trifluoroacetate.

In a glovebox, catalyst (5.4 mg, 1.0 equiv) is charged to an oven-dried 20 mL glass liner. The liner is inserted into a stainless steel high pressure reactor. The system is purged with $N_2$ five times and purged with $CO_2$ twice. While under the positive flow of $CO_2$ that is derived from the combustion of fossil fuel, a solution of dipropylene glycol (75 μL) in biobased propylene oxide (5 mL, 25,000 equiv) is charged to the reaction vessel. The reaction is heated to 50° C., then pressurized with carbon dioxide (300 psi) and stirred.

After 6 h the reaction is vented and quenched with acidic methanol (0.2 mL). The reaction is cooled to room temperature, and the resulting polymer is diluted with acetone (5 mL) and transferred to a foil pan. The unreacted propylene oxide and acetone is removed by evaporation.

The polycarbonate polyol composition thus obtained consists predominantly of polymer chains having a formula:

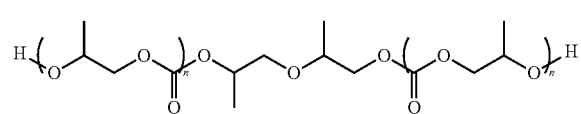

P-1

EQUIVALENTS

All material cited in this application, including, but not limited to, patents and patent applications, regardless of the format of such literature and similar materials, are expressly incorporated herein by reference in their entirety. In the event that one or more of the incorporated literature and similar materials differs from or contradicts this application, including but not limited to defined terms, term usage, described techniques, or the like, this application controls.

What is claimed is:

1. A polymer composition comprising aliphatic polycarbonate polyols having a structure P1:

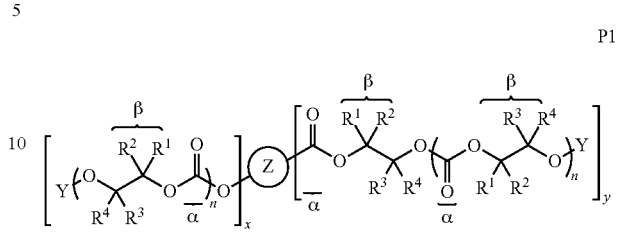

P1 wherein:

$R^1$, $R^2$, $R^3$, and $R^4$ are, independently at each occurrence in the polymer chain, selected from the group consisting of: —H; and an optionally substituted group selected from $C_{1-30}$ aliphatic, and $C_{6-14}$ aryl; 3- to 12-membered heterocycle, and 5- to 12-membered heteroaryl, where two or more of $R^1$, $R^2$, $R^3$, and $R^4$ can be taken together with intervening atoms to form one or more optionally substituted 3- to 12-membered rings, optionally containing one or more heteroatoms;

the radiocarbon content of carbon atoms at positions labeled α is lower than the radiocarbon content of carbon atoms at positions labeled β;

Y is, at each occurrence, independently —H, a reactive group, or a site of attachment to chain-extending moieties or isocyanates;

n is, at each occurrence, independently an integer from about 2 to about 50;

Z is a covalent bond or a multivalent moiety; and x and y are each independently an integer from 0 to 6, where the sum of x and y is between 2 and 6.

2. The polymer composition according to claim 1, comprising polymer chains characterized in that the carbon atoms at positions labeled α have a percent Modern Carbon (pMC) value measured according to ASTM D6866-16 (Method B) that is lower than a pMC value of the carbon atoms at positions labeled β.

3. The polymer composition according to claim 2, wherein the carbon atoms at positions labeled α have a pMC value measured according to ASTM D6866-16 (Method B) of less than about 50, less than about 20, less than about 10, less than about 5, or less than about 1.

4. The polymer composition according to claim 3, wherein the carbon atoms at positions labeled α have a pMC value measured according to ASTM D6866-16 (Method B) of 0.

5. The polymer composition according to claim 2, wherein the carbon atoms at positions labeled β have a pMC value measured according to ASTM D6866-16 (Method B) of greater than about 75, greater than about 80, greater than about 85, greater than about 90, greater than about 95, greater than about 100, or greater than about 105.

6. The polymer composition according to claim 5, wherein the carbon atoms at positions labeled β have a pMC value measured according to ASTM D6866-16 (Method B) of about 100.

7. The polymer composition according to claim 1, wherein the % biobased carbon is greater than about 40%, 50%, 60%, 70%, 80%, or 90%.

8. The polymer composition according to claim 1, wherein the % biobased carbon is less than about 80%, 70%, 60%, 50%, 40%, 30%, 20%, or 10%.

9. The polymer composition according to claim 1, wherein the % biobased carbon is between about 40% and about 80%, between about 40% and about 60%, or between about 60% and about 80%.

10. The polymer composition according to claim 1, derived from biobased epoxides selected from the group consisting of ethylene oxide, propylene oxide, epoxides derived from natural oils, epoxides derived from fatty acids, epoxides derived from fatty alcohols, and mixtures of any two or more of these.

11. The polymer composition according to claim 1, derived from biobased epoxides selected from the group consisting of ethylene oxide and propylene oxide.

12. The polymer composition according to claim 1, comprising aliphatic polycarbonates, wherein the aliphatic polycarbonates are characterized in that, on average in the composition, the percentage of carbonate linkages is 90% or greater.

13. The polymer composition according to claim 1, wherein the polymer composition has a number average molecular weight (Mn) of greater than about 20,000 g/mol.

14. The polymer composition according to claim 1, wherein the polymer composition has a number average molecular weight (Mn) of less than about 20,000 g/mol.

15. A method comprising steps of:
   a) fermenting carbohydrate derived from biomass to produce biobased ethanol;
   b) converting the biobased ethanol to a biobased epoxide; and
   c) copolymerizing carbon dioxide sequestered from a fossil carbon source with the biobased epoxide to produce a polymer composition of claim 1.

16. A method comprising steps of:
   a) treating a polymer composition of claim 1 to liberate a cyclic carbonate of formula:

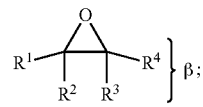

b) treating the cyclic carbonate to liberate carbon atoms labeled α as $CO_2$, and carbon atoms labeled β as an epoxide of formula:

and c) measuring the radiocarbon content of the $CO_2$ comprising carbon atoms labeled α, and the epoxide comprising carbon atoms labeled β.

17. The method according to claim 16, further comprising the step of separating the $CO_2$ from the epoxide.

18. The method according to claim 16, wherein the radiocarbon content is measured according to ASTM D6866-16 (Method B).

19. The method according to claim 16, further comprising the steps of:
   e) using the measured radiocarbon content to confirm that the carbon atoms at the positions labeled α are derived from a fossil carbon source by having a pMC value measured according to ASTM D6866-16 (Method B) of less than about 1, less than about 0.1, or less than about 0.03; and
   f) using the measured radiocarbon content to confirm that the carbon atoms at the positions labeled β are derived from a biobased feedstock by having a pMC value measured according to ASTM D6866-16 (Method B) of at least about 95, at least about 99, or at least about 100.

20. The polymer composition of claim 1, comprising aliphatic polycarbonate polyols having a structure P2b:

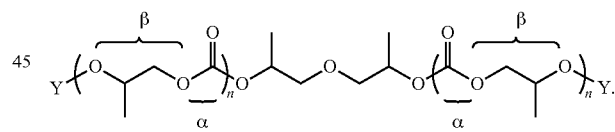

21. The polymer composition of claim 1, comprising aliphatic polycarbonate polyols having a structure Q7a':

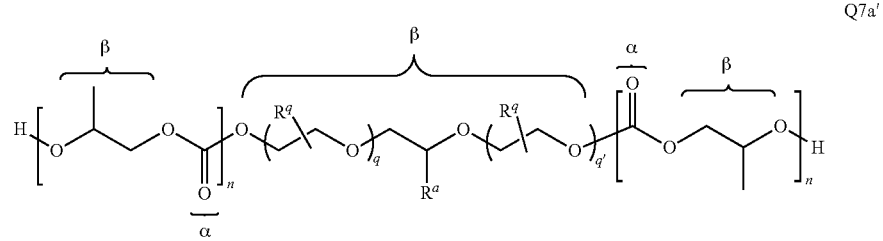

wherein

R$^q$ is at each occurrence in the polymer chain independently —H or —CH$_3$;

R$^a$ is —H, or —CH$_3$; and q and q' are independently an integer from about 0 to about 40.

22. The polymer composition according to claim 1, wherein the polymer composition has an number average molecular weight (Mn) between about 500 and about 5,000 g/mol.

* * * * *